US012714746B2

(12) United States Patent
Graham et al.

(10) Patent No.: US 12,714,746 B2

(45) **Date of Patent: *Aug. 25, 2026**

(54) METHOD FOR PREVENTION AND TREATMENT OF VIRAL DISEASE

(71) Applicant: MOREHOUSE SCHOOL OF MEDICINE, Atlanta, GA (US)

(72) Inventors: Barney S. Graham, Smyrna, GA (US); Erica L. Johnson, Tyrone, GA (US); James W. Lillard, Smyrna, GA (US)

(73) Assignee: MOREHOUSE SCHOOL OF MEDICINE, Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/320,827

(22) Filed: Sep. 5, 2025

(65) Prior Publication Data

US 2026/0061045 A1 Mar. 5, 2026

Related U.S. Application Data

(63) Continuation-in-part of application No. 19/282,277, filed on Jul. 28, 2025.

(60) Provisional application No. 63/691,575, filed on Sep. 6, 2024, provisional application No. 63/676,744, filed on Jul. 29, 2024.

(51) Int. Cl.

| | |
|---|---|
| ***A61K 39/145*** | (2006.01) |
| ***A61K 39/00*** | (2006.01) |
| ***A61P 37/04*** | (2006.01) |
| ***C07K 14/005*** | (2006.01) |
| ***C12N 9/24*** | (2006.01) |

(52) U.S. Cl.

CPC ............ *A61K 39/145* (2013.01); *A61P 37/04* (2018.01); *C07K 14/005* (2013.01); *C12N 9/2402* (2013.01); *C12Y 302/01018* (2013.01); *A61K 2039/53* (2013.01); *A61K 2039/6031* (2013.01); *A61K 2039/70* (2013.01); *C07K 2319/00* (2013.01); *C12N 2760/16122* (2013.01); *C12N 2760/16134* (2013.01); *C12N 2760/16171* (2013.01)

(58) Field of Classification Search

CPC .............. A61K 39/145; A61K 2039/53; A61K 2039/6031; A61K 2039/70; A61P 37/04; C07K 14/005; C07K 2319/00; C12N 9/2402; C12N 2760/16122; C12N 2760/16134; C12N 2760/16171; C12Y 302/01018

See application file for complete search history.

(56) References Cited

U.S. PATENT DOCUMENTS

| | | | |
|---|---|---|---|
| 4,373,071 A | 2/1983 | Itakura | |
| 4,401,796 A | 8/1983 | Itakura | |
| 4,415,732 A | 11/1983 | Caruthers et al. | |
| 4,458,066 A | 7/1984 | Caruthers et al. | |
| 4,500,707 A | 2/1985 | Caruthers et al. | |
| 4,668,777 A | 5/1987 | Caruthers et al. | |
| 4,868,116 A | 9/1989 | Morgan et al. | |
| 4,973,679 A | 11/1990 | Caruthers et al. | |
| 4,980,286 A | 12/1990 | Morgan et al. | |
| 5,047,524 A | 9/1991 | Monforte et al. | |
| 5,132,418 A | 7/1992 | Caruthers et al. | |
| 5,153,319 A | 10/1992 | Caruthers et al. | |
| 5,262,530 A | 11/1993 | Andrus et al. | |
| 5,700,642 A | 12/1997 | Monforte et al. | |
| 2017/0029488 A1 | 2/2017 | Gurnett-Bander et al. | |
| 2019/0224305 A1 * | 7/2019 | Heaton | C12N 7/00 |
| 2020/0268873 A1 * | 8/2020 | Polacek | A61K 39/145 |
| 2021/0023205 A1 | 1/2021 | D'Aoust et al. | |

FOREIGN PATENT DOCUMENTS

| | | |
|---|---|---|
| WO | 90/02806 | 8/1989 |
| WO | 89/07136 | 3/1990 |
| WO | 2008157419 | 12/2008 |

OTHER PUBLICATIONS

Kielian M, Rey FA. Virus membrane-fusion proteins: more than one way to make a hairpin. Nat Rev Microbiol. Jan. 2006;4(1):67-76. (Year: 2006).*

Böttcher-Friebertshäuser E, Klenk HD, Garten W. Activation of influenza viruses by proteases from host cells and bacteria in the human airway epithelium. Pathog Dis. Nov. 2013;69(2):87-100. Epub Jul. 2, 2013. (Year: 2013).*

Hendin HE, Lavoie PO, Gravett JM, Pillet S, Saxena P, Landry N, D'Aoust MA, Ward BJ. Elimination of receptor binding by influenza hemagglutinin improves vaccine-induced immunity. NPJ Vaccines. Apr. 11, 2022;7(1):42. (Year: 2022).*

Mittal N, Sengupta N, Malladi SK, Reddy P, Bhat M, Rajmani RS, Sedeyn K, Saelens X, Dutta S, Varadarajan R. Protective Efficacy of Recombinant Influenza Hemagglutinin Ectodomain Fusions. Viruses. Aug. 27, 2021;13(9):1710. (Year: 2021).*

Banerjee K, Weliky DP. Folded monomers and hexamers of the ectodomain of the HIV gp41 membrane fusion protein: potential roles in fusion and synergy between the fusion peptide, hairpin, and membrane-proximal external region. Biochemistry. Nov. 25, 2014;53(46):7184-98. Epub Nov. 14, 2014. (Year: 2014).*

(Continued)

*Primary Examiner* — Rachel B Gill

(74) *Attorney, Agent, or Firm* — Ping Wang; Michael Ye; Kalos Athena Wang PLLC

(57) ABSTRACT

A method for reducing mortality resulting from viral infection, reducing viral load resulting from viral infection, or increasing immunity to viral infection in a subject is described. The method comprises administering a hybrid protein comprises a first domain comprising a sequence encoding a surface protein of an enveloped RNA virus and a second domain comprising a sequence encoding an ectodomain of a type 2 transmembrane domain protein, wherein the second domain is located at the C-terminal of the first domain. The hybrid protein or an mRNA encoding such protein can be used as a vaccine against the infection of the enveloped RNA virus.

24 Claims, 14 Drawing Sheets

Specification includes a Sequence Listing.

(56) References Cited

OTHER PUBLICATIONS

Lee YN, Kim MC, Lee YT, Kim YJ, Kang SM. Mechanisms of Cross-protection by Influenza Virus M2-based Vaccines. Immune Netw. Oct. 2015;15(5):213-21. doi: 10.4110/in.2015.15.5.213. Epub Oct. 26, 2015. (Year: 2015).*

Shi L, Long Y, Zhu Y, Dong J, Chen Y, Feng H, Sun X. VLPs containing stalk domain and ectodomain of matrix protein 2 of influenza induce protection in mice. Virol J. Feb. 27, 2023;20(1):38. (Year: 2023).*

Kielian M. Class II virus membrane fusion proteins. Virology. Jan. 5, 2006;344(1):38-47. (Year: 2006).*

Sodhi PV, Sidime F, Tarazona DD, Valdivia F, Levano KS. A Closer Look at ACE2 Signaling Pathway and Processing during COVID-19 Infection: Identifying Possible Targets. Vaccines (Basel). Dec. 21, 2022;11(1):13. (Year: 2022).*

Gao L, Aizaki H, He JW, Lai MM. Interactions between viral nonstructural proteins and host protein hVAP-33 mediate the formation of hepatitis C virus RNA replication complex on lipid raft. J Virol. Apr. 2004;78(7):3480-8. (Year: 2004).*

Villanueva RA, Rouillé Y, Dubuisson J. Interactions between virus proteins and host cell membranes during the viral life cycle. Int Rev Cytol. 2005;245:171-244. (Year: 2005).*

Guo Q, Qian C, Wang X, Qian ZM. Transferrin receptors. Exp Mol Med. Apr. 2025;57(4):724-732. Epub Apr. 22, 2025. (Year: 2025).*

Batzer MA, Carlton JE, Deininger PL. Enhanced evolutionary PCR using oligonucleotides with inosine at the 3'-terminus. Nucleic Acids Res. Sep. 25, 1991;19(18):5081.

Ohtsuka E, Matsuki S, Ikehara M, Takahashi Y, Matsubara K. An alternative approach to deoxyoligonucleotides as hybridization probes by insertion of deoxyinosine at ambiguous codon positions. J Biol Chem. Mar. 10, 1985;260(5):2605-8.

Berndt Oberhauser, Ernst Wagner, Effective incorporation of 2'-O-methyl-oligoribonuclectides into liposomes and enhanced cell association through modification with thiocholesterol, Nucleic Acids Research, vol. 20, Issue 3, Feb. 11, 1992, pp. 533-538.

Saison-Behmoaras T, Tocque B, Rey I, Chassignol M, Thuong NT, Hélène C. Short modified antisense oligonucleotides directed against Ha-ras point mutation induce selective cleavage of the mRNA and inhibit T24 cells proliferation. EMBO J. May 1991;10(5):1111-8.

Kabanov AV, Vinogradov SV, Ovcharenko AV, Krivonos AV, Melik-Nubarov NS, Kiselev VI, Severin ES. A new class of antivirals: antisense oligonucleotides combined with a hydrophobic substituent effectively inhibit influenza virus reproduction and synthesis of virus-specific proteins in MDCK cells. FEBS Lett. Jan. 1, 1990;259(2):327-30.

Regan G. Shea, James C. Marsters, Norbert Bischofberger, Synthesis, hybridization properties and antiviral activity of lipid-oligodeoxynucleotide conjugates, Nucleic Acids Research, vol. 18, Issue 13, Jul. 11, 1990, pp. 3777-3783.

Teng MN, Collins PL. The central conserved cystine noose of the attachment G protein of human respiratory syncytial virus is not required for efficient viral infection in vitro or in vivo. J Virol. Jun. 2002;76(12):6164-71.

International Search Report of the International Searching Authority issued on Jan. 30, 2026 in PCT Application No. PCT/US25/45185.

Written Opinion of the International Searching Authority issued on Jan. 30, 2026 in PCT Application No. PCT/US25/45185.

* cited by examiner

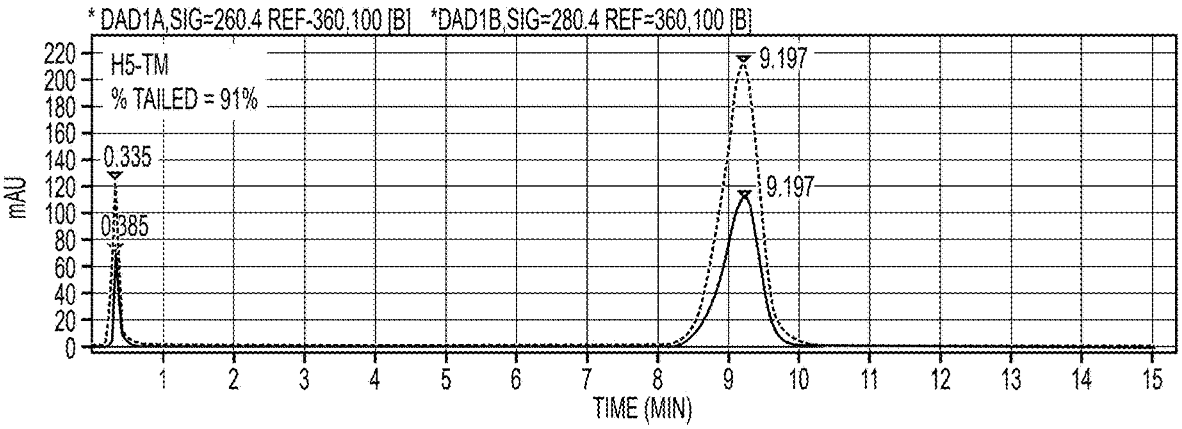
FIG. 6B
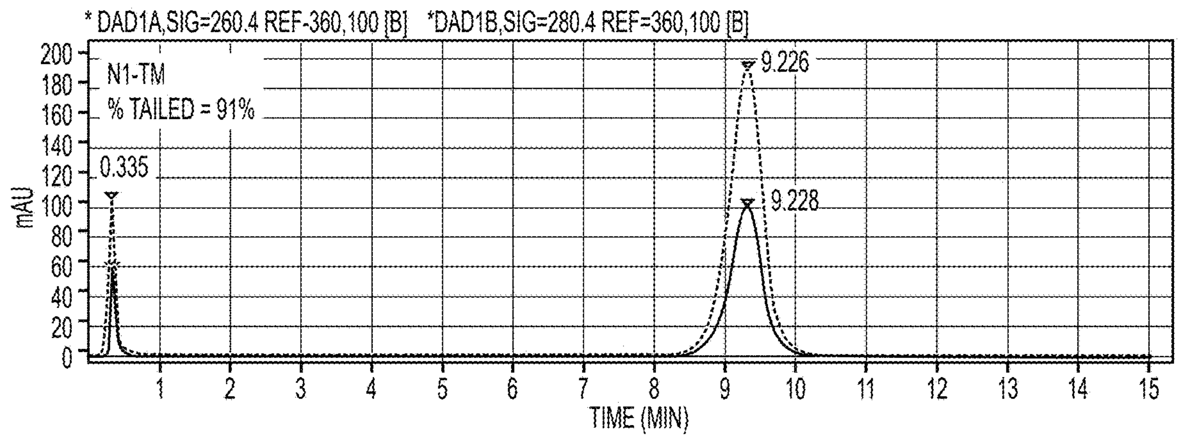
FIG. 6C
| mRNA CONSTRUCT | DISTRIBUTION (#As) | MAIN PEAK LENGTH (#As) |
|---|---|---|
| HYBRID-S | 83-90 | 86 |
| H5-TM | 93-97 | 94 |
| N1-TM | 85-95 | 94 |
| FLU 1014 | 85-91 | 88 |
FIG. 6D

SEQUENCE LISTING

```
Sequence total quantity: 28
SEQ ID NO: 1           moltype = AA  length = 998
FEATURE                Location/Qualifiers
source                 1..998
                       mol_type = protein
                       organism = synthetic construct
SEQUENCE: 1
MENIVLLLAI VSLVKSDQIC IGYHANNSTE QVDTIMEKNV TVTHAQDILE KTHNGKLCDL  60
NGVKPLILKD CSVAGWLLGN PMCDEFIRVP EWSYIVERAN PANDLCFPGS LNDYEELKHM  120
LSRINHFEKI QIIPKSSWPN HETSLGVSAA CPYQGAPSFF RNVVWLIKKN DAYPTIKISY  180
NNTNREDLLI LWGIHHSNNA EEQTNLYKNP ITYISVGTST LNQRLAPKIA TRSQVNGQRG  240
RMDFFWTILK PDDAIHFESN GNFIAPEYAY KIVKKGDSTI MKSGVEYGHC NTKCQTPVGA  300
INSSMPFHNI PLTIGECPKY VKSNKLVLAT GLRNSPLREK RRKRGLFGAX AGFIEGGWQG  360
MVDGWYGYHH SNEQGSGYAA DKESTQKAID GVTNKVNSII DKMNTQFEAV GREFNNLERR  420
IENLNKKMED GFLDVWTYNA ELLVLMENER TLDFHDSNVK NLYDKVRLQL RDNAKELGNG  480
CFEFYHKCDN ECMESVRNGT YDYPQYSEEA RLKREEISGV KLESVGTYQI LSAIGGYIPE  540
APRDGQAYVR KDGEWVLLST FLGGHSIQTG NQYQPEPCNQ SIITYENNTW VNQTYINISN  600
TNFLAEQAVT SVTLAGNSSL CPISGWAIYS KDNGIRIGSK GDVFVIREPF ISCSHLECRT  660
FFLTQGALLN DKHSNGTVKD RSPYRTLMSC PVGEAPSPYN SRFESVAWSA SACHDGISWL  720
TIGISGPDNG AVAVLKYNGI ITDTIKSWRN NILRTQESEC ACVNGSCFTV MTDGPSNGQA  780
SYKIFKIEKG KVVKSVEMNA PNYHYEECSC YPDAGDIMCV CRDNWHGSNR PWVSFNQNLE  840
YQIGYICSGI FGDNPRPNDG TGSCSPMPSN GAYGVKGFSF KYGNGVWIGR TKSTSSRSGF  900
EMIWDPNGWT ETDSSFSVKQ DIVEITDWSG YSGSFVQHPE LTGLDCMRPC FWVELIRGRP  960
KENTIWTSGS SISFCGVNSD TVGWSWPDGA ELPFTIDK                         998
```

```
SEQ ID NO: 2            moltype = AA  length = 16
FEATURE                 Location/Qualifiers
source                  1..16
                        mol_type = protein
                        organism = synthetic construct
SEQUENCE: 2
MENIVLLLAI VSLVKS                                                   16

SEQ ID NO: 3            moltype = AA  length = 328
FEATURE                 Location/Qualifiers
source                  1..328
                        mol_type = protein
                        organism = synthetic construct
SEQUENCE: 3
DQICIGYHAN NSTEQVDTIM EKNVTVTHAQ DILEKTHNGK LCDLNGVKPL ILKDCSVAGW  60
LLGNPMCDEF IRVPEWSYIV ERANPANDLC FPGSLNDYEE LKHMLSRINH FEKIQIIPKS  120
SWPNHETSLG VSAACPYQGA PSFFRNVVWL IKKNDAYPTI KISYNNTNRE DLLILWGIHH  180
SNNAEEQTNL YKNPITYISV GTSTLNQRLA PKIATRSQVN GQRGRMDFFW TILKDDAIHF  240
ESNGNFIAPE YAYKIVKKGD STIMKSGVEY GHCNTKCQTP VGAINSSMPF HNIHPLTIGE  300
CPKYVKSNKL VLATGLRNSP LREKRRKR                                      328

SEQ ID NO: 4            moltype = AA  length = 187
FEATURE                 Location/Qualifiers
source                  1..187
                        mol_type = protein
                        organism = synthetic construct
SEQUENCE: 4
GLFGAXAGFI EGGWQGMVDG WYGYHHSNEQ GSGYAADKES TQKAIDGVTN KVNSIIDKMN  60
TQFEAVGREF NNLERRIENL NKKMEDGFLD VWTYNAELLV LMENERTLDF HDSNVKNLYD  120
KVRLQLRDNA KELGNGCFEF YHKCDNECME SVRNGTYDYP QYSEEARLKR EEISGVKLES  180
VGTYQIL                                                             187

SEQ ID NO: 5            moltype = AA  length = 33
FEATURE                 Location/Qualifiers
source                  1..33
                        mol_type = protein
                        organism = synthetic construct
SEQUENCE: 5
SAIGGYIPEA PRDGQAYVRK DGEWVLLSTF LGG                                33

SEQ ID NO: 6            moltype = AA  length = 434
FEATURE                 Location/Qualifiers
REGION                  1..434
                        note = ectodomain of the wild-type NA of H5N1 strain
                         A/Texas/37/2024
source                  1..434
                        mol_type = protein
                        organism = unidentified
SEQUENCE: 6
HSIQTGNQYQ PEPCNQSIIT YENNTWVNQT YINISNTNFL AEQAVTSVTL AGNSSLCPIS  60
GWAIYSKDNG IRIGSKGDVF VIREPFISCS HLECRTFFLT QGALLNDKHS NGTVKDRSPY  120
RTLMSCPVGE APSPYNSRFE SVAWSASACH DGISWLTIGI SGPDNGAVAV LKYNGIITDT  180
IKSWRNNILR TQESECACVN GSCFTVMTDG PSNGQASYKI FKIEKGKVVK SVEMNAPNYH  240
YEECSCYPDA GDIMCVCRDN WHGSNRPWVS FNQNLEYQIG YICSGIFGDN PRPNDGTGSC  300
SPMPSNGAYG VKGFSFKYGN GVWIGRTKST SSRSGFEMIW DPNGWTETDS SFSVKQDIVE  360
ITDWSGYSGS FVQHPELTGL DCMRPCFWVE LIRGRPKENT IWTSGSSISF CGVNSDTVGW  420
SWPDGAELPF TIDK                                                     434

SEQ ID NO: 7            moltype = AA  length = 567
FEATURE                 Location/Qualifiers
REGION                  1..567
                        note = complete amino acid sequence of wild-type HA of H5N1
                         strain A/Texas/37/2024
source                  1..567
                        mol_type = protein
                        organism = unidentified
SEQUENCE: 7
MENIVLLLAI VSLVKSDQIC IGYHANNSTE QVDTIMEKNV TVTHAQDILE KTHNGKLCDL  60
NGVKPLILKD CSVAGWLLGN PMCDEFIRVP EWSYIVERAN PANDLCYPGS LNDYEELKHM  120
LSRINHFEKI QIIPKSSWPN HETSLGVSAA CPYQGAPSFF RNVVWLIKKN DAYPTIKISY  180
NNTNREDLLI LWGIHHSNNA EEQTNLYKNP ITYISVGTST LNQRLAPKIA TRSQVNGQRG  240
RMDFFWTILK PDDAIHFESN GNFIAPEYAY KIVKKGDSTI MKSGVEYGHC NTKCQTPVGA  300
INSSMPFHNI HPLTIGECPK YVKSNKLVLA TGLRNSPLRE KRRKRGLFGA XAGFIEGGWQ  360
GMVDGWYGYH HSNEQGSGYA ADKESTQKAI DGVTNKVNSI IDKMNTQFEA VGREFNNLER  420
RIENLNKKME DGFLDVWTYN AELLVLMENE RTLDFHDSNV KNLYDKVRLQ LRDNAKELGN  480
GCFEFYHKCD NECMESVRNG TYDYPQYSEE ARLKREEISG VKLESVGTYQ ILSIYSTAAS  540
SLALAIMMAG LSLWMCSNGS LQCRICI                                       567
```

-continued

```
SEQ ID NO: 8            moltype = DNA  length = 1751
FEATURE                 Location/Qualifiers
misc_feature            1..1751
                        note = complete nucleotide sequence of wild-type HA of H5N1
                         strain A/Texas/37/2024
source                  1..1751
                        mol_type = genomic DNA
                        organism = unidentified
SEQUENCE: 8
ggttcactct gtcaaaatgg agaacatagt actacttctt gcaatagtta gccttgttaa  60
aagtgatcag atttgcattg gttaccatgc aaacaattcg acagagcaag ttgacacgat  120
aatggaaaag aacgtcactg ttacacatgc ccaagacata ctggaaaaaa cacacaacgg  180
gaagctatgc gacctaaatg gggtgaagcc actgatttta aaggactgca gtgtagctgg  240
atggctcctc ggaaacccaa tgtgcgacga attcatcaga gtgccggaat ggtcttacat  300
agtggagcgg gctaacccag ctaatgacct ctgttaccca gggagcctca atgactatga  360
agaactgaaa cacatgttga gcagaataaa tcattttgag aagattcaga tcattcccaa  420
gagttcctgg ccaaatcatg aaacatcact aggggtgagc gcagcttgtc cataccaggg  480
agcaccctcc tttttcagaa atgtggtgtg gcttatcaaa aagaacgatg catacccaac  540
aataaagata agctacaata atactaatcg ggaagatctc ttgatactgt gggggattca  600
tcattccaac aatgcagaag agcagacaaa tctctacaaa aacccaatca cctacatttc  660
agttggaaca tcaactttaa accagaggtt ggcaccaaaa atagctacta gatcccaagt  720
aaacgggcaa cgtggaagaa tggacttctt ctggacaatc ttaaaaccag atgatgcaat  780
ccatttcgag agtaacggaa atttcattgc tccagagtat gcatacaaaa ttgttaagaa  840
aggggactcg acaattatga aaagtggagt ggaatatggc cactgcaaca ccaaatgtca  900
aaccccagta ggtgcgataa attctagtat gccatttcac aacatacatc ctctcaccat  960
tggggaatgc cccaaatacg tgaaatcaaa caagttggtc cttgcgactg ggctcagaaa  1020
tagtcctcta agagaaaaga gaagaaaaag aggtctgttt ggggcgawag cagggtttat  1080
agagggagga tggcagggaa tggttgatgg ttggtatggg taccatcata gcaatgagca  1140
ggggagtggg tacgctgcgg acaaagaatc cacccaaaag gcaatagatg gagttaccaa  1200
taaggtcaac tcaatcattg acaaaatgaa cactcaattt gaggcagttg gaagggagtt  1260
taataactta gaaaggagga tagagaattt gaacaagaaa atggaagacg gattcctaga  1320
tgtctggacc tataatgctg aacttctagt tctcatggaa aacgagagga ctctagattt  1380
ccatgattca aatgtcaaga acctttacga caaagtcaga ttacagctta gggataatgc  1440
aaaggagctg ggtaacggct gtttcgaatt ctatcacaaa tgtgataatg aatgtatgga  1500
aagtgtgaga aatgggacgt atgactaccc tcagtattca gaagaagcaa gattaaaaag  1560
agaagaaata agcggagtga aattagaatc agtaggaact taccagatac tgtcaattta  1620
ttcaacagcg gcaagttccc tagcactggc aatcatgatg gctggtctat ctttatggat  1680
gtgctccaat gggtcgttac aatgcagaat ttgcatttag atttatgagc tcagattgta  1740
gttaaaaaca c                                                       1751

SEQ ID NO: 9            moltype = AA  length = 469
FEATURE                 Location/Qualifiers
REGION                  1..469
                        note = complete amino acid sequence of wild-type NA of H5N1
                         strain A/Texas/37/2024
source                  1..469
                        mol_type = protein
                        organism = unidentified
SEQUENCE: 9
MNPNQKITTI GSICMVIGIV SLMLQIGNII SIWVSHSIQT GNQYQPEPCN QSIITYENNT  60
WVNQTYINIS NTNFLAEQAV TSVTLAGNSS LCPISGWAIY SKDNGIRIGS KGDVFVIREP  120
FISCSHLECR TFFLTQGALL NDKHSNGTVK DRSPYRTLMS CPVGEAPSPY NSRFESVAWS  180
ASACHDGISW LTIGISGPDN GAVAVLKYNG IITDTIKSWR NNILRTQESE CACVNGSCFT  240
VMTDGPSNGQ ASYKIFKIEK GKVVKSVEMN APNYHYEECS CYPDAGDIMC VCRDNWHGSN  300
RPWVSFNQNL EYQIGYICSG IFGDNPRPND GTGSCSPMPS NGAYGVKGFS FKYGNGVWIG  360
RTKSTSSRSG FEMIWDPNGW TETDSSFSVK QDIVEITDWS GYSGSFVQHP ELTGLDCMRP  420
CFWVELIRGR PKENTIWTSG SSISFCGVNS DTVGWSWPDG AELPFTIDK             469

SEQ ID NO: 10           moltype = DNA  length = 1433
FEATURE                 Location/Qualifiers
misc_feature            1..1433
                        note = complete nucleotide sequence of wild-type NA of H5N1
                         strain A/Texas/37/2024
source                  1..1433
                        mol_type = genomic DNA
                        organism = unidentified
SEQUENCE: 10
agttcaaaat gaatccaaat caaaagataa caaccattgg atcaatctgt atggtaattg  60
ggatagtcag cttgatgctg caaattggga acataatctc aatatgggtt agccattcaa  120
tccaaacagg gaatcaatac cagcctgaac catgcaatca aagcatcatt acctatgaga  180
acaacacctg ggtaaatcag acgtatatca acatcagcaa taccaatttt cttgctgagc  240
aggctgttac ttcggtaaca ttagcgggca attcatctct ttgccctatt agtgggtggg  300
caatatacag taaggacaac ggtataagaa ttgggtctaa gggggatgtg tttgttataa  360
gagaaccatt catctcatgc tcccacttgg aatgcagaac ctttttcctg acccagggag  420
ctctgctgaa tgacaaacat tctaatggga cagttaagga tagaagccct tatagaactt  480
tgatgagttg tcccgtgggt gaggctcctt ccccgtacaa ttcaagattt gagtctgttg  540
cttggtcggc aagtgcttgt catgatggca tcagttggtt gacaatcggt atttctggtc  600
cagacaatgg agctgtggct gtattgaagt acaatggcat aataacggat actatcaaga  660
gttggagaaa caacattttg agaactcaag aatctgaatg tgcttgcgta aatggctcct  720
```

-continued

```
gcttcaccgt aatgactgat ggaccaagca atgggcaggc ctcatataaa atcttcaaga  780
tagagaaagg gaaagttgtc aaatcagttg aaatgaatgc ccctaattac cactacgagg  840
aatgctcctg ttatcctgat gcgggtgata ttatgtgtgt gtgcagggac aattggcatg  900
gctcgaaccg gccgtgggta tcttttaatc aaaatctgga gtatcaaata ggatatatat  960
gcagtgggat tttcggggac aatccccgcc ccaatgatgg aacaggcagt tgcagtccaa  1020
tgccctctaa tggggcatat ggggtgaaag ggttttcatt taagtacggt aatggggttt  1080
ggatcggaag aacaaaaagc actagttcca gaagcggctt tgagatgatt tgggatccga  1140
atgggtggac tgagacagac agtagtttct cagtgaagca agacattgta gaaataactg  1200
actggtcagg atatagtggg agttttgtcc agcatccaga actgacagga ttagattgca  1260
tgaggccttg tttctgggtt gagctaatta gagggaggcc caaagagaat acaatttgga  1320
ctagcgggag cagcatatcc ttttgtggtg taaatagtga cactgtgggt tggtcttggc  1380
cagacggtgc tgagttgcca ttcaccattg acaagtagtt tgttcaaaaa act        1433

SEQ ID NO: 11          moltype = AA  length = 24
FEATURE                Location/Qualifiers
source                 1..24
                       mol_type = protein
                       organism = synthetic construct
SEQUENCE: 11
GGLVPRGSHH HHHHSAWSHP QFEK                                         24

SEQ ID NO: 12          moltype = AA  length = 5
FEATURE                Location/Qualifiers
source                 1..5
                       mol_type = protein
                       organism = synthetic construct
SEQUENCE: 12
KRRKR                                                              5

SEQ ID NO: 13          moltype = AA  length = 983
FEATURE                Location/Qualifiers
source                 1..983
                       mol_type = protein
                       organism = synthetic construct
SEQUENCE: 13
DQICIGYHAN NSTEQVDTIM EKNVTVTHAQ DILEKTHNGK LCDLNGVKPL ILKDCSVAGW  60
LLGNPMCDEF IRVPEWSYIV ERANPANDLC FPGSLNDYEE LKHMLSRINH FEKIQIIPKS  120
SWPNHETSLG VSAACPYQGA PSFFRNVVWL IKKNDAYPTI KISYNNTNRE DLLILWGIHH  180
SNNAEEQTNL YKNPITYISV GTSTLNQRLA PKIATRSQVN GQRGRMDFFW TILKPDDAIH  240
FESNGNFIAP EYAYKIVKKG DSTIMKSGVE YGHCNTKCQT PVGAINSSMP FHNIHPLTIG  300
ECPKYVKSNK LVLATGLRNS PLREKRRKRG LFGAXAGFIE GGWQGMVDGW YGYHHSNEQG  360
SGYAADKEST QKAIDGVTNK VNSIIDKMNT QFEAVGREFN NLERRIENLN KKMEDGFLDV  420
WTYNAELLVL MENERTLDFH DSNVKNLYDK VRLQLRDNAK ELGNGCFEFY HKCDNECMES  480
VRNGTYDYPQ YSEEARLKRE EISGVKLESV GTYQILSAIG GYIPEAPRDG QAYVRKDGEW  540
VLLSTFLGGH SIQTGNQYQP EPCNQSIITY ENNTWVNQTY INISNTNFLA EQAVTSVTLA  600
GNSSLCPISG WAIYSKDNGI RIGSKGDVFV IREPFISCSH LECRTFFLTQ GALLNDKHSN  660
GTVKDRSPYR TLMSCPVGEA PSPYNSRFES VAWSASACHD GISWLTIGIS GPDNGAVAVL  720
KYNGIITDTI KSWRNNILRT QESECACVNG SCFTVMTDGP SNGQASYKIF KIEKGKVVKS  780
VEMNAPNYHY EECSCYPDAG DIMCVCRDNW HGSNRPWVSF NQNLEYQIGY ICSGIFGDNP  840
RPNDGTGSCS PMPSNGAYGV KGFSFKYGNG VWIGRTKSTS SRSGFEMIWD PNGWTETDSS  900
FSVKQDIVEI TDWSGYSGSF VQHPELTGLD CMRPCFWVEL IRGRPKENTI WTSGSSISFC  960
GVNSDTVGWS WPDGAELPFT IDK                                          983

SEQ ID NO: 14          moltype = AA  length = 5
FEATURE                Location/Qualifiers
source                 1..5
                       mol_type = protein
                       organism = synthetic construct
SEQUENCE: 14
GGGGS                                                              5

SEQ ID NO: 15          moltype = AA  length = 4
FEATURE                Location/Qualifiers
source                 1..4
                       mol_type = protein
                       organism = synthetic construct
SEQUENCE: 15
GSGS                                                               4

SEQ ID NO: 16          moltype = AA  length = 999
FEATURE                Location/Qualifiers
source                 1..999
                       mol_type = protein
                       organism = synthetic construct
SEQUENCE: 16
MENIVLLLAI VSLVKSDQIC IGYHANNSTE QVDTIMEKNV TVTHAQDILE KTHNGKLCDL  60
NGVKPLILKD CSVAGWLLGN PMCDEFIRVP EWSYIVERAN PANDLCFPGS LNDYEELKHM  120
LSRINHFEKI QIIPKSSWPN HETSLGVSAA CPYQGAPSFF RNVVWLIKKN DAYPTIKISY  180
NNTNREDLLI LWGIHHSNNA EEQTNLYKNP ITYISVGTST LNQRLAPKIA TRSQVNGQRG  240
```

-continued

```
RMDFFWTILK PDDAIHFESN GNFIAPEYAY KIVKKGDSTI MKSGVEYGHC NTKCQTPVGA  300
INSSMPFHNI HPLTIGECPK YVKSNKLVLA TGLRNSPLRE KRRKRGLFGA IAGFIEGGWQ  360
GMVDGWYGYH HSNEQGSGYA ADKESTQKAI DGVTNKVNSI IDKMNTQFEA VGREFNNLER  420
RIENLNKKME DGFLDVWTYN AELLVLMENE RTLDFHDSNV KNLYDKVRLQ LRDNAKELGN  480
GCFEFYHKCD NECMESVRNG TYDYPQYSEE ARLKREEISG VKLESVGTYQ ILSAIGGYIP  540
EAPRDGQAYV RKDGEWVLLS TFLGGHSIQT GNQYQPEPCN QSIITYENNT WVNQTYINIS  600
NTNFLAEQAV TSVTLAGNSS LCPISGWAIY SKDNGIRIGS KGDVFVIREP FISCSHLECR  660
TFFLTQGALL NDKHSNGTVK DRSPYRTLMS CPVGEAPSPY NSRFESVAWS ASACHDGISW  720
LTIGISGPDN GAVAVLKYNG IITDTIKSWR NNILRTQESE CACVNGSCFT VMTDGPSNGQ  780
ASYKIFKIEK GKVVKSVEMN APNYHYEECS CYPDAGDIMC VCRDNWHGSN RPWVSFNQNL  840
EYQIGYICSG IFGDNPRPND GTGSCSPMPS NGAYGVKGFS FKYGNGVWIG RTKSTSSRSG  900
FEMIWDPNGW TETDSSFSVK QDIVEITDWS GYSGSFVQHP ELTGLDCMRP CFWVELIRGR  960
PKENTIWTSG SSISFCGVNS DTVGWSWPDG AELPFTIDK                         999

SEQ ID NO: 17          moltype = AA  length = 567
FEATURE                Location/Qualifiers
source                 1..567
                       mol_type = protein
                       organism = synthetic construct
SEQUENCE: 17
MENIVLLLAI VSLVKSDQIC IGYHANNSTE QVDTIMEKNV TVTHAQDILE KTHNGKLCDL  60
NGVKPLILKD CSVAGWLLGN PMCDEFIRVP EWSYIVERAN PANDLCFPGS LNDYEELKHM  120
LSRINHFEKI QIIPKSSWPN HETSLGVSAA CPYQGAPSFF RNVVWLIKKN DAYPTIKISY  180
NNTNREDLLI LWGIHHSNNA EEQTNLYKNP ITYISVGTST LNQRLAPKIA TRSQVNGQRG  240
RMDFFWTILK PDDAIHFESN GNFIAPEYAY KIVKKGDSTI MKSGVEYGHC NTKCQTPVGA  300
INSSMPFHNI HPLTIGECPK YVKSNKLVLA TGLRNSPLRE KRRKRGLFGA IAGFIEGGWQ  360
GMVDGWYGYH HSNEQGSGYA ADKESTQKAI DGVTNKVNSI IDKMNTQFEA VGREFNNLER  420
RIENLNKKME DGFLDVWTYN AELLVLMENE RTLDFHDSNV KNLYDKVRLQ LRDNAKELGN  480
GCFEFYHKCD NECMESVRNG TYDYPQYSEE ARLKREEISG VKLESVGTYQ ILSIYSTAAS  540
SLALAIMMAG LSLWMCSNGS LQCRICI                                     567

SEQ ID NO: 18          moltype = AA  length = 469
FEATURE                Location/Qualifiers
source                 1..469
                       mol_type = protein
                       organism = synthetic construct
SEQUENCE: 18
MNPNQKITTI GSICMVIGIV SLMLQIGNII SIWVSHSIQT GNQYQPEPCN QSIITYENNT  60
WVNQTYINIS NTNFLAEQAV TSVTLAGNSS LCPISGWAIY SKDNGIRIGS KGDVFVIREP  120
FISCSHLECR TFFLTQGALL NDKHSNGTVK DRSPYRTLMS CPVGEAPSPY NSRFESVAWS  180
ASACHDGISW LTIGISGPDN GAVAVLKYNG IITDTIKSWR NNILRTQESE CACVNGSCFT  240
VMTDGPSNGQ ASYKIFKIEK GKVVKSVEMN APNYHYEECS CYPDAGDIMC VCRDNWHGSN  300
RPWVSFNQNL EYQIGYICSG IFGDNPRPND GTGSCSPMPS NGAYGVKGFS FKYGNGVWIG  360
RTKSTSSRSG FEMIWDPNGW TETDSSFSVK QDIVEITDWS GYSGSFVQHP ELTGLDCMRP  420
CFWVELIRGR PKENTIWTSG SSISFCGVNS DTVGWSWPDG AELPFTIDK             469

SEQ ID NO: 19          moltype = AA  length = 1051
FEATURE                Location/Qualifiers
source                 1..1051
                       mol_type = protein
                       organism = synthetic construct
SEQUENCE: 19
MENIVLLLAI VSLVKSDQIC IGYHANNSTE QVDTIMEKNV TVTHAQDILE KTHNGKLCDL  60
NGVKPLILKD CSVAGWLLGN PMCDEFIRVP EWSYIVERAN PANDLCFPGS LNDYEELKHM  120
LSRINHFEKI QIIPKSSWPN HETSLGVSAA CPYQGAPSFF RNVVWLIKKN DAYPTIKISY  180
NNTNREDLLI LWGIHHSNNA EEQTNLYKNP ITYISVGTST LNQRLAPKIA TRSQVNGQRG  240
RMDFFWTILK PDDAIHFESN GNFIAPEYAY KIVKKGDSTI MKSGVEYGHC NTKCQTPVGA  300
INSSMPFHNI HPLTIGECPK YVKSNKLVLA TGLRNSPLRE KRRKRGLFGA IAGFIEGGWQ  360
GMVDGWYGYH HSNEQGSGYA ADKESTQKAI DGVTNKVNSI IDKMNTQFEA VGREFNNLER  420
RIENLNKKME DGFLDVWTYN AELLVLMENE RTLDFHDSNV KNLYDKVRLQ LRDNAKELGN  480
GCFEFYHKCD NECMESVRNG TYDYPQYSEE ARLKREEISG VKLESVGTYQ ILSIYSTAAS  540
SLALAIMMAG LSLWMCSNGS LQCRICIGGS GGSGGSGGSG SGMNPNQKIT TIGSICMVIG  600
IVSLMLQIGN IISIWVSHSI QTGNQYQPEP CNQSIITYEN NTWVNQTYIN ISNTNFLAEQ  660
AVTSVTLAGN SSLCPISGWA IYSKDNGIRI GSKGDVFVIR EPFISCSHLE CRTFFLTQGA  720
LLNDKHSNGT VKDRSPYRTL MSCPVGEAPS PYNSRFESVA WSASACHDGI SWLTIGISGP  780
DNGAVAVLKY NGIITDTIKS WRNNILRTQE SECACVNGSC FTVMTDGPSN GQASYKIFKI  840
EKGKVVKSVE MNAPNYHYEE CSCYPDAGDI MCVCRDNWHG SNRPWVSFNQ NLEYQIGYIC  900
SGIFGDNPRP NDGTGSCSPM PSNGAYGVKG FSFKYGNGVW IGRTKSTSSR SGFEMIWDPN  960
GWTETDSSFS VKQDIVEITD WSGYSGSFVQ HPELTGLDCM RPCFWVELIR GRPKENTIWT  1020
SGSSISFCGV NSDTVGWSWP DGAELPFTID K                                1051

SEQ ID NO: 20          moltype = AA  length = 1071
FEATURE                Location/Qualifiers
source                 1..1071
                       mol_type = protein
                       organism = synthetic construct
SEQUENCE: 20
MENIVLLLAI VSLVKSDQIC IGYHANNSTE QVDTIMEKNV TVTHAQDILE KTHNGKLCDL  60
NGVKPLILKD CSVAGWLLGN PMCDEFIRVP EWSYIVERAN PANDLCFPGS LNDYEELKHM  120
```

-continued

```
LSRINHFEKI QIIPKSSWPN HETSLGVSAA CPYQGAPSFF RNVVWLIKKN DAYPTIKISY  180
NNTNREDLLI LWGIHHSNNA EEQTNLYKNP ITYISVGTST LNQRLAPKIA TRSQVNGQRG  240
RMDFFWTILK PDDAIHFESN GNFIAPEYAY KIVKKGDSTI MKSGVEYGHC NTKCQTPVGA  300
INSSMPFHNI HPLTIGECPK YVKSNKLVLA TGLRNSPLRE KRRKRGLFGA IAGFIEGGWQ  360
GMVDGWYGYH HSNEQGSGYA ADKESTQKAI DGVTNKVNSI IDKMNTQFEA VGREFNNLER  420
RIENLNKKME DGFLDVWTYN AELLVLMENE RTLDFHDSNV KNLYDKVRLQ LRDNAKELGN  480
GCFEFYHKCD NECMESVRNG TYDYPQYSEE ARLKREEISG VKLESVGTYQ ILSIYSTAAS  540
SLALAIMMAG LSLWMCSNGS LQCRICIGSG SAIGGYIPEA PRDGQAYVRK DGEWVLLSTF  600
LGMNPNQKIT TIGSICMVIG IVSLMLQIGN IISIWVSHSI QTGNQYQPEP CNQSIITYEN  660
NTWVNQTYIN ISNTNFLAEQ AVTSVTLAGN SSLCPISGWA IYSKDNGIRI GSKGDVFVIR  720
EPFISCSHLE CRTFFLTQGA LLNDKHSNGT VKDRSPYRTL MSCPVGEAPS PYNSRFESVA  780
WSASACHDGI SWLTIGISGP DNGAVAVLKY NGIITDTIKS WRNNILRTQE SECACVNGSC  840
FTVMTDGPSN GQASYKIFKI EKGKVVKSVE MNAPNYHYEE CSCYPDAGDI MCVCRDNWHG  900
SNRPWVSFNQ NLEYQIGYIC SGIFGDNPRP NDGTGSCSPM PSNGAYGVKG FSFKYGNGVW  960
IGRTKSTSSR SGFEMIWDPN GWTETDSSFS VKQDIVEITD WSGYSGSFVQ HPELTGLDCM  1020
RPCFWVELIR GRPKENTIWT SGSSISFCGV NSDTVGWSWP DGAELPFTID K           1071

SEQ ID NO: 21          moltype = AA  length = 24
FEATURE                Location/Qualifiers
source                 1..24
                       mol_type = protein
                       organism = synthetic construct
SEQUENCE: 21
GGLVPRGSHH HHHHSAWSHP QFEK                                          24

SEQ ID NO: 22          moltype = AA  length = 1023
FEATURE                Location/Qualifiers
source                 1..1023
                       mol_type = protein
                       organism = synthetic construct
SEQUENCE: 22
MENIVLLLAI VSLVKSDQIC IGYHANNSTE QVDTIMEKNV TVTHAQDILE KTHNGKLCDL  60
NGVKPLILKD CSVAGWLLGN PMCDEFIRVP EWSYIVERAN PANDLCFPGS LNDYEELKHM  120
LSRINHFEKI QIIPKSSWPN HETSLGVSAA CPYQGAPSFF RNVVWLIKKN DAYPTIKISY  180
NNTNREDLLI LWGIHHSNNA EEQTNLYKNP ITYISVGTST LNQRLAPKIA TRSQVNGQRG  240
RMDFFWTILK PDDAIHFESN GNFIAPEYAY KIVKKGDSTI MKSGVEYGHC NTKCQTPVGA  300
INSSMPFHNI HPLTIGECPK YVKSNKLVLA TGLRNSPLRE KRRKRGLFGA IAGFIEGGWQ  360
GMVDGWYGYH HSNEQGSGYA ADKESTQKAI DGVTNKVNSI IDKMNTQFEA VGREFNNLER  420
RIENLNKKME DGFLDVWTYN AELLVLMENE RTLDFHDSNV KNLYDKVRLQ LRDNAKELGN  480
GCFEFYHKCD NECMESVRNG TYDYPQYSEE ARLKREEISG VKLESVGTYQ ILSAIGGYIP  540
EAPRDGQAYV RKDGEWVLLS TFLGGHSIQT GNQYQPEPCN QSIITYENNT WVNQTYINIS  600
NTNFLAEQAV TSVTLAGNSS LCPISGWAIY SKDNGIRIGS KGDVFVIREP FISCSHLECR  660
TFFLTQGALL NDKHSNGTVK DRSPYRTLMS CPVGEAPSPY NSRFESVAWS ASACHDGISW  720
LTIGISGPDN GAVAVLKYNG IITDTIKSWR NNILRTQESE CACVNGSCFT VMTDGPSNGQ  780
ASYKIFKIEK GKVVKSVEMN APNYHYEECS CYPDAGDIMC VCRDNWHGSN RPWVSFNQNL  840
EYQIGYICSG IFGDNPRPND GTGSCSPMPS NGAYGVKGFS FKYGNGVWIG RTKSTSSRSG  900
FEMIWDPNGW TETDSSFSVK QDIVEITDWS GYSGSFVQHP ELTGLDCMRP CFWVELIRGR  960
PKENTIWTSG SSISFCGVNS DTVGWSWPDG AELPFTIDKG GLVPRGSHHH HHHSAWSHPQ  1020
FEK                                                                 1023

SEQ ID NO: 23          moltype = AA  length = 999
FEATURE                Location/Qualifiers
source                 1..999
                       mol_type = protein
                       organism = synthetic construct
SEQUENCE: 23
MENIVLLLAI VSLVKSDQIC IGYHANNSTE QVDTIMEKNV TVTHAQDILE KTHNGKLCDL  60
NGVKPLILKD CSVAGWLLGN PMCDEFIRVP EWSYIVERAN PANDLCFPGS LNDYEELKHM  120
LSRINHFEKI QIIPKSSWPN HETSLGVSAA CPYQGAPSFF RNVVWLIKKN DAYPTIKISY  180
NNTNREDLLI LWGIHHSNNA EDQTDLYKNP ITYISVGTST LNQRLAPKIA TRSQVNGLRG  240
RMDFFWTILK PDDAIHFESN GNFIAPEYAY KIVKKGDSTI MKSGVEYGHC NTKCQTPVGA  300
INSSMPFHNI HPLTIGECPK YVKSNKLVLA TGLRNSPLRE KRRKRGLFGA IAGFIEGGWQ  360
GMVDGWYGYH HSNEQGSGYA ADKESTQKAI DGVTNKVNSI IDKMNTQFEA VGREFNNLER  420
RIENLNKKME DGFLDVWTYN AELLVLMENE RTLDFHDSNV KNLYDKVRLQ LRDNAKELGN  480
GCFEFYHKCD NECMESVRNG TYDYPQYSEE ARLKREEISG VKLESVGTYQ ILSAIGGYIP  540
EAPRDGQAYV RKDGEWVLLS TFLGGHSIQT GNQYQPEPCN QSIITYENNT WVNQTYINIS  600
NTNFLAEQAV TSVTLAGNSS LCPISGWAIY SKDNGIRIGS KGDVFVIREP FISCSHLECR  660
TFFLTQGALL NDKHSNGTVK DRSPYRTLMS CPVGEAPSPY NSRFESVAWS ASACHDGISW  720
LTIGISGPDN GAVAVLKYNG IITDTIKSWR NNILRTQESE CACVNGSCFT VMTDGPSNGQ  780
ASYKIFKIEK GKVVKSVEMN APNYHYEECS CYPDAGDIMC VCRDNWHGSN RPWVSFNQNL  840
EYQIGYICFG IFGDNPRPND GTGSCSPMPS NGAYGVKGFS FKYGNGVWIG RTKSTSSRSG  900
FEMIWDPNGW TETDSSFSVK QDIVEITDWS GYSGSFVQHP ELTGLDCMRP CFWVELIRGR  960
PKENTIWTSG SSISFCGVNS DTVGWSWPDG AELPFTIDK                          999

SEQ ID NO: 24          moltype = AA  length = 983
FEATURE                Location/Qualifiers
source                 1..983
                       mol_type = protein
                       organism = synthetic construct
```

-continued

SEQUENCE: 24
DQICIGYHAN NSTEQVDTIM EKNVTVTHAQ DILEKTHNGK LCDLNGVKPL ILKDCSVAGW 60
LLGNPMCDEF IRVPEWSYIV ERANPANDLC FPGSLNDYEE LKHMLSRINH FEKIQIIPKS 120
SWPNHETSLG VSAACPYQGA PSFFRNVVWL IKKNDAYPTI KISYNNTNRE DLLILWGIHH 180
SNNAEEQTNL YKNPITYISV GTSTLNQRLA PKIATRSQVN GQRGRMDFFW TILKPDDAIH 240
FESNGNFIAP EYAYKIVKKG DSTIMKSGVE YGHCNTKCQT PVGAINSSMP FHNIHPLTIG 300
ECPKYVKSNK LVLATGLRNS PLREKRRKRG LFGAIAGFIE GGWQGMVDGW YGYHHSNEQG 360
SGYAADKEST QKAIDGVTNK VNSIIDKMNT QFEAVGREFN NLERRIENLN KKMEDGFLDV 420
WTYNAELLVL MENERTLDFH DSNVKNLYDK VRLQLRDNAK ELGNGCFEFY HKCDNECMES 480
VRNGTYDYPQ YSEEARLKRE EISGVKLESV GTYQILSAIG GYIPEAPRDG QAYVRKDGEW 540
VLLSTFLGGH SIQTGNQYQP EPCNQSIITY ENNTWVNQTY INISNTNFLA EQAVTSVTLA 600
GNSSLCPISG WAIYSKDNGI RIGSKGDVFV IREPFISCSH LECRTFFLTQ GALLNDKHSN 660
GTVKDRSPYR TLMSCPVGEA PSPYNSRFES VAWSASACHD GISWLTIGIS GPDNGAVAVL 720
KYNGIITDTI KSWRNNILRT QESECACVNG SCFTVMTDGP SNGQASYKIF KIEKGKVVKS 780
VEMNAPNYHY EECSCYPDAG DIMCVCRDNW HGSNRPWVSF NQNLEYQIGY ICSGIFGDNP 840
RPNDGTGSCS PMPSNGAYGV KGFSFKYGNG VWIGRTKSTS SRSGFEMIWD PNGWTETDSS 900
FSVKQDIVEI TDWSGYSGSF VQHPELTGLD CMRPCFWVEL IRGRPKENTI WTSGSSISFC 960
GVNSDTVGWS WPDGAELPFT IDK 983

SEQ ID NO: 25 moltype = AA length = 1035
FEATURE Location/Qualifiers
source 1..1035
mol_type = protein
organism = synthetic construct
SEQUENCE: 25
DQICIGYHAN NSTEQVDTIM EKNVTVTHAQ DILEKTHNGK LCDLNGVKPL ILKDCSVAGW 60
LLGNPMCDEF IRVPEWSYIV ERANPANDLC FPGSLNDYEE LKHMLSRINH FEKIQIIPKS 120
SWPNHETSLG VSAACPYQGA PSFFRNVVWL IKKNDAYPTI KISYNNTNRE DLLILWGIHH 180
SNNAEEQTNL YKNPITYISV GTSTLNQRLA PKIATRSQVN GQRGRMDFFW TILKPDDAIH 240
FESNGNFIAP EYAYKIVKKG DSTIMKSGVE YGHCNTKCQT PVGAINSSMP FHNIHPLTIG 300
ECPKYVKSNK LVLATGLRNS PLREKRRKRG LFGAIAGFIE GGWQGMVDGW YGYHHSNEQG 360
SGYAADKEST QKAIDGVTNK VNSIIDKMNT QFEAVGREFN NLERRIENLN KKMEDGFLDV 420
WTYNAELLVL MENERTLDFH DSNVKNLYDK VRLQLRDNAK ELGNGCFEFY HKCDNECMES 480
VRNGTYDYPQ YSEEARLKRE EISGVKLESV GTYQILSIYS TAASSLALAI MMAGLSLWMC 540
SNGSLQCRIC IGGSGGSGGS GGSGSGMNPN QKITTIGSIC MVIGIVSLML QIGNIISIWV 600
SHSIQTGNQY QPEPCNQSII TYENNTWVNQ TYINISNTNF LAEQAVTSVT LAGNSSLCPI 660
SGWAIYSKDN GIRIGSKGDV FVIREPFISC SHLECRTFFL TQGALLNDKH SNGTVKDRSP 720
YRTLMSCPVG EAPSPYNSRF ESVAWSASAC HDGISWLTIG ISGPDNGAVA VLKYNGIITD 780
TIKSWRNNIL RTQESECACV NGSCFTVMTD GPSNGQASYK IFKIEKGKVV KSVEMNAPNY 840
HYEECSCYPD AGDIMCVCRD NWHGSNRPWV SFNQNLEYQI GYICSGIFGD NPRPNDGTGS 900
CSPMPSNGAY GVKGFSFKYG NGVWIGRTKS TSSRSGFEMI WDPNGWTETD SSFSVKQDIV 960
EITDWSGYSG SFVQHPELTG LDCMRPCFWV ELIRGRPKEN TIWTSGSSIS FCGVNSDTVG 1020
WSWPDGAELP FTIDK 1035

SEQ ID NO: 26 moltype = AA length = 1055
FEATURE Location/Qualifiers
source 1..1055
mol_type = protein
organism = synthetic construct
SEQUENCE: 26
DQICIGYHAN NSTEQVDTIM EKNVTVTHAQ DILEKTHNGK LCDLNGVKPL ILKDCSVAGW 60
LLGNPMCDEF IRVPEWSYIV ERANPANDLC FPGSLNDYEE LKHMLSRINH FEKIQIIPKS 120
SWPNHETSLG VSAACPYQGA PSFFRNVVWL IKKNDAYPTI KISYNNTNRE DLLILWGIHH 180
SNNAEEQTNL YKNPITYISV GTSTLNQRLA PKIATRSQVN GQRGRMDFFW TILKPDDAIH 240
FESNGNFIAP EYAYKIVKKG DSTIMKSGVE YGHCNTKCQT PVGAINSSMP FHNIHPLTIG 300
ECPKYVKSNK LVLATGLRNS PLREKRRKRG LFGAIAGFIE GGWQGMVDGW YGYHHSNEQG 360
SGYAADKEST QKAIDGVTNK VNSIIDKMNT QFEAVGREFN NLERRIENLN KKMEDGFLDV 420
WTYNAELLVL MENERTLDFH DSNVKNLYDK VRLQLRDNAK ELGNGCFEFY HKCDNECMES 480
VRNGTYDYPQ YSEEARLKRE EISGVKLESV GTYQILSIYS TAASSLALAI MMAGLSLWMC 540
SNGSLQCRIC IGSGSAIGGY IPEAPRDGQA YVRKDGEWVL LSTFLGMNPN QKITTIGSIC 600
MVIGIVSLML QIGNIISIWV SHSIQTGNQY QPEPCNQSII TYENNTWVNQ TYINISNTNF 660
LAEQAVTSVT LAGNSSLCPI SGWAIYSKDN GIRIGSKGDV FVIREPFISC SHLECRTFFL 720
TQGALLNDKH SNGTVKDRSP YRTLMSCPVG EAPSPYNSRF ESVAWSASAC HDGISWLTIG 780
ISGPDNGAVA VLKYNGIITD TIKSWRNNIL RTQESECACV NGSCFTVMTD GPSNGQASYK 840
IFKIEKGKVV KSVEMNAPNY HYEECSCYPD AGDIMCVCRD NWHGSNRPWV SFNQNLEYQI 900
GYICSGIFGD NPRPNDGTGS CSPMPSNGAY GVKGFSFKYG NGVWIGRTKS TSSRSGFEMI 960
WDPNGWTETD SSFSVKQDIV EITDWSGYSG SFVQHPELTG LDCMRPCFWV ELIRGRPKEN 1020
TIWTSGSSIS FCGVNSDTVG WSWPDGAELP FTIDK 1055

SEQ ID NO: 27 moltype = AA length = 1007
FEATURE Location/Qualifiers
source 1..1007
mol_type = protein
organism = synthetic construct
SEQUENCE: 27
DQICIGYHAN NSTEQVDTIM EKNVTVTHAQ DILEKTHNGK LCDLNGVKPL ILKDCSVAGW 60
LLGNPMCDEF IRVPEWSYIV ERANPANDLC FPGSLNDYEE LKHMLSRINH FEKIQIIPKS 120
SWPNHETSLG VSAACPYQGA PSFFRNVVWL IKKNDAYPTI KISYNNTNRE DLLILWGIHH 180
SNNAEEQTNL YKNPITYISV GTSTLNQRLA PKIATRSQVN GQRGRMDFFW TILKPDDAIH 240

-continued

```
FESNGNFIAP EYAYKIVKKG DSTIMKSGVE YGHCNTKCQT PVGAINSSMP FHNIHPLTIG  300
ECPKYVKSNK LVLATGLRNS PLREKRRKRG LFGAIAGFIE GGWQGMVDGW YGYHHSNEQG  360
SGYAADKEST QKAIDGVTNK VNSIIDKMNT QFEAVGREFN NLERRIENLN KKMEDGFLDV  420
WTYNAELLVL MENERTLDFH DSNVKNLYDK VRLQLRDNAK ELGNGCFEFY HKCDNECMES  480
VRNGTYDYPQ YSEEARLKRE EISGVKLESV GTYQILSAIG GYIPEAPRDG QAYVRKDGEW  540
VLLSTFLGGH SIQTGNQYQP EPCNQSIITY ENNTWVNQTY INISNTNFLA EQAVTSVTLA  600
GNSSLCPISG WAIYSKDNGI RIGSKGDVFV IREPFISCSH LECRTFFLTQ GALLNDKHSN  660
GTVKDRSPYR TLMSCPVGEA PSPYNSRFES VAWSASACHD GISWLTIGIS GPDNGAVAVL  720
KYNGIITDTI KSWRNNILRT QESECACVNG SCFTVMTDGP SNGQASYKIF KIEKGKVVKS  780
VEMNAPNYHY EECSCYPDAG DIMCVCRDNW HGSNRPWVSF NQNLEYQIGY ICSGIFGDNP  840
RPNDGTGSCS PMPSNGAYGV KGFSFKYGNG VWIGRTKSTS SRSGFEMIWD PNGWTETDSS  900
FSVKQDIVEI TDWSGYSGSF VQHPELTGLD CMRPCFWVEL IRGRPKENTI WTSGSSISFC  960
GVNSDTVGWS WPDGAELPFT IDKGGLVPRG SHHHHHHSAW SHPQFEK                1007

SEQ ID NO: 28          moltype = AA  length = 983
FEATURE                Location/Qualifiers
source                 1..983
                       mol_type = protein
                       organism = synthetic construct
SEQUENCE: 28
DQICIGYHAN NSTEQVDTIM EKNVTVTHAQ DILEKTHNGK LCDLNGVKPL ILKDCSVAGW  60
LLGNPMCDEF IRVPEWSYIV ERANPANDLC FPGSLNDYEE LKHMLSRINH FEKIQIIPKS  120
SWPNHETSLG VSAACPYQGA PSFFRNVVWL IKKNDAYPTI KISYNNTNRE DLLILWGIHH  180
SNNAEDQTDL YKNPITYISV GTSTLNQRLA PKIATRSQVN GLRGRMDFFW TILKPDDAIH  240
FESNGNFIAP EYAYKIVKKG DSTIMKSGVE YGHCNTKCQT PVGAINSSMP FHNIHPLTIG  300
ECPKYVKSNK LVLATGLRNS PLREKRRKRG LFGAIAGFIE GGWQGMVDGW YGYHHSNEQG  360
SGYAADKEST QKAIDGVTNK VNSIIDKMNT QFEAVGREFN NLERRIENLN KKMEDGFLDV  420
WTYNAELLVL MENERTLDFH DSNVKNLYDK VRLQLRDNAK ELGNGCFEFY HKCDNECMES  480
VRNGTYDYPQ YSEEARLKRE EISGVKLESV GTYQILSAIG GYIPEAPRDG QAYVRKDGEW  540
VLLSTFLGGH SIQTGNQYQP EPCNQSIITY ENNTWVNQTY INISNTNFLA EQAVTSVTLA  600
GNSSLCPISG WAIYSKDNGI RIGSKGDVFV IREPFISCSH LECRTFFLTQ GALLNDKHSN  660
GTVKDRSPYR TLMSCPVGEA PSPYNSRFES VAWSASACHD GISWLTIGIS GPDNGAVAVL  720
KYNGIITDTI KSWRNNILRT QESECACVNG SCFTVMTDGP SNGQASYKIF KIEKGKVVKS  780
VEMNAPNYHY EECSCYPDAG DIMCVCRDNW HGSNRPWVSF NQNLEYQIGY ICFGIFGDNP  840
RPNDGTGSCS PMPSNGAYGV KGFSFKYGNG VWIGRTKSTS SRSGFEMIWD PNGWTETDSS  900
FSVKQDIVEI TDWSGYSGSF VQHPELTGLD CMRPCFWVEL IRGRPKENTI WTSGSSISFC  960
GVNSDTVGWS WPDGAELPFT IDK                                          983
```

METHOD FOR PREVENTION AND TREATMENT OF VIRAL DISEASE

This application is a Continuation-in-Part of U.S. patent application Ser. No. 19/282,277, filed on Jul. 28, 2025, which claims priority of U.S. Provisional Application No. 63/676,744, filed on Jul. 29, 2024, and U.S. Provisional Application No. 63/691,575, filed on Sep. 6, 2024, all of which are incorporated by reference in their entirety.

The application contains a Sequence Listing which has been submitted electronically in .XML format and is hereby incorporated by reference in its entirety. Said .XML copy, created on Sep. 5, 2025, is named "1013-831 CIP.xml" and is 45,511 bytes in size. The sequence listing contained in this .XML file is part of the specification and is hereby incorporated by reference herein in its entirety.

FIELD

The present application relates generally to vaccines and, in particular, to vaccines for influenza, amongst other diseases.

BACKGROUND

Currently licensed vaccines are made by inactivating influenza virus grown in eggs or cell culture, subunit hemagglutinin (HA) protein, or live virus grown in eggs. These manufacturing approaches require at least 4-5 months before deployment and are not easily scaled to the level needed for a global vaccine campaign. There are experimental mRNA vaccines expressing full-length membrane-anchored HA sometimes combined with membrane anchored neuraminidase (NA). These vaccines can be sufficient for protection, but do not guarantee equimolar expression of HA and NA. Immunogenicity has been shown in humans, but efficacy testing in large populations has not been done. The disclosed concept expresses an HA/NA chimeric protein that would be secreted from the transduced cell and express only the ectodomain of HA and NA. Delivery as mRNA would make it amenable to scale-up enough for several billion doses if needed.

SUMMARY

An aspect of the present application is directed to a method for reducing mortality resulting from viral infection comprising administering to a subject in need thereof an effective amount of a composition comprising a hybrid protein comprising a first domain comprising a sequence encoding an ectodomain of a trimeric surface protein of an enveloped RNA virus and a second domain comprising a sequence encoding an ectodomain of a type 2 transmembrane domain protein, wherein the second domain is located at the C-terminal of the first domain; and a pharmaceutically acceptable carrier.

An aspect of the present application is directed to a method for reducing viral load resulting from a viral infection in a subject in need thereof, comprising administering to the subject in need thereof an effective amount of a pharmaceutical composition comprising a hybrid protein comprising a first domain comprising a sequence encoding an ectodomain of a trimeric surface protein of an enveloped RNA virus and a second domain comprising a sequence encoding an ectodomain of a type 2 transmembrane domain protein, wherein the second domain is located at the C-terminal of the first domain; and a pharmaceutically acceptable carrier.

An aspect of the present application is directed to a method for increasing immunity to viral infection in a subject in need thereof, comprising administering to the subject in need thereof an effective amount of a pharmaceutical composition comprising a hybrid protein comprising a first domain comprising a sequence encoding an ectodomain of a trimeric surface protein of an enveloped RNA virus and a second domain comprising a sequence encoding an ectodomain of a type 2 transmembrane domain protein, wherein the second domain is located at the C-terminal of the first domain; and a pharmaceutically acceptable carrier.

An aspect of the present application relates to a hybrid protein comprising a first domain comprising a sequence encoding an ectodomain of a trimeric surface protein of an enveloped RNA virus and a second domain comprising a sequence encoding an ectodomain of a type 2 transmembrane domain protein, wherein the second domain is located at the C-terminal of the first domain. In some embodiments, the hybrid protein further comprises a transmembrane domain of the trimeric surface protein and/or a transmembrane domain of the type 2 transmembrane domain protein. In some embodiments, the hybrid protein further comprises a cytoplasmic tail of the trimeric surface protein and/or a cytoplasmic tail of the type 2 transmembrane domain protein. In some embodiments, the hybrid protein further comprises an intracytoplasmic linker.

An aspect of the present application relates to a hybrid protein comprising a first domain comprising a sequence encoding an immunogen of a virus; and a second domain comprising a sequence encoding an ectodomain of a type 2 transmembrane domain protein, wherein the second domain is located at the C-terminal of the first domain and wherein the second domain serves as an adjuvant to augment immune responses to the immunogen.

An aspect of the present application relates to a hybrid protein comprising a first domain comprising a sequence encoding an immunogen from a first virus, and a second domain comprising a sequence from a type 2 transmembrane domain protein of a second virus. In some embodiments, the second domain is located at the C-terminal of the first domain. In some embodiments, the first virus and the second virus are the same virus. In some embodiments, the first virus and the second virus are different viruses. In some embodiments, the immunogen is an F protein of an RSV or human metapneumovirus and the type 2 transmembrane domain protein is a glycoprotein of an RSV or human metapneumovirus.

An aspect of the present application relates to a polynucleotide comprising a sequence encoding the hybrid protein of the present application. In some embodiments, the polynucleotide is a DNA molecule. In some embodiments, the polynucleotide is an RNA molecule. In some embodiments, the polynucleotide is a mRNA molecule.

An aspect of the present application relates to an expression vector that comprises the polynucleotide of the present application. In some embodiments, the expression vector is a non-viral vector, such as a plasmid. In some embodiments, the expression vector is a viral vector.

An aspect of the present application relates to a flu vaccine. In some embodiments, the vaccine comprises a hybrid protein the present application. In some embodiments, the vaccine comprises a polynucleotide of the present application. In some embodiments, the vaccine comprises an expression vector of the present application. In some embodiments, the vaccine comprises a mRNA of the present application encapsulated in lipid nanoparticles.

An aspect of the present application relates to a method for immunizing a subject against a flu virus. The method comprises the step of administering to the subject an effective amount of the vaccine composition of the present application.

An aspect of the present application relates to a method for introducing an immune response to a virus in a subject. The method comprises the step of administering to the subject an effective amount of the vaccine composition of the present application.

These and other aspects, objects, features, and advantages of the example embodiments will become apparent to those having ordinary skill in the art upon consideration of the following detailed description of example embodiments.

BRIEF DESCRIPTION OF DRAWINGS

An understanding of the features and advantages of the present application may be obtained by reference to the accompanying figures that sets forth illustrative embodiments, in which the principles of the application may be utilized. The figures herein are for illustrative purposes only and are not necessarily drawn to scale.

FIGS. 6A-6C show the percentage of mRNA tailing by analytical HPLC and tail length by LC/MS. mRNA % tailing was determined on the basis of binding to an oligo dT column by analytical HPLC for constructs Hybrid-S (FIG. 6A), H5-TM (FIG. 6B), and N1-TM (FIG. 6C). FIG. 6D shows the distribution and main peak length tor the constructs depicted in FIGS. 6A-6C and for Flu 1014.

FIG. 12A shows survival of female BALB/c Mice following H5N1 challenge. FIG. 12B depicts the percent body weight change following intranasal challenge with H5N1. FIG. 12C depicts the Kaplan-Meier survival analysis over 7 days post-challenge.

FIG. 14A shows the response in pre-bleed mice at Day −1.

FIG. 14B shows the response at Day 20 in mice that were primed only. FIG. 14C shows the response at Day 28 in mice that were both primed and boosted.

DETAILED DESCRIPTION

Figure 1:
FIG. 1 is a schematic representation of the general design of the hybrid protein of the present application.

Reference will be made in detail to certain aspects and exemplary embodiments of the application, illustrating examples in the accompanying structures and figures. The aspects of the application will be described in conjunction with the exemplary embodiments, including methods, materials and examples. Such description is non-limiting and the scope of the application is intended to encompass all equivalents, alternatives, and modifications, either generally known, or incorporated here. Unless otherwise defined, all technical and scientific terms used herein have the same meaning as commonly understood by one of ordinary skill in the art to which this application belongs. One of skill in the art will recognize many techniques and materials similar or equivalent to those described here, which could be used in the practice of the aspects and embodiments of the present application. The described aspects and embodiments of the application are not limited to the methods and materials described.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible unless otherwise specified.

I. Definitions

All definitions, as defined and used herein, should be understood to control over dictionary definitions, definitions in documents incorporated by reference, and/or ordinary meanings of the defined terms.

The terms “a”, “an,” or “the” as used in the specification and claims, unless clearly indicated to the contrary, should be understood to mean “at least one” or “one or more,” unless the content clearly dictates otherwise.

The phrase "and/or," as used herein in the specification and claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

As used herein, the term "adjuvant" refers to a compound or mixture that enhances an immune response. The term "adjuvant" refers to an agent that when administered concurrently with the vaccine composition of the present application, accelerates, prolongs, enhances and/or boosts the immune response thereto. Adjuvants can enhance an immune response by several mechanisms including, e.g., lymphocyte recruitment, stimulation of B and/or T cells, stimulation of dendritic cells and/or stimulation of macrophages.

As used herein, the terms "codon optimized" and "codon optimization" refer to a process for modifying a nucleic acid sequence according to one or more of the following: (1) to match codon usage in a host target; (2) to promote increased expression; (3) to ensure proper folding; (4) to provide a GC content suitable for increasing mRNA stability or reducing secondary structures; (5) to minimize tandem repeat codons or base runs that may impair gene construction or expression; (6) to customize transcriptional and translational control regions; (7) to insert or remove protein trafficking sequences; (8) to remove/add post translation modification sites in an encoded protein (e.g. glycosylation sites); (9) to add, remove or shuffle protein domains; (10) to insert or delete restriction sites; (11) modify ribosome binding sites and mRNA degradation sites; (12) to adjust translational rates to allow the various domains of the protein to fold properly; and (13) to reduce or eliminate problem secondary structures within the polynucleotide. Codon optimization tools, algorithms and services are known in the art-non-limiting examples include services from GeneArt (Life Technologies), DNA2.0 (Menlo Park Calif.) and/or proprietary methods.

The term "effective amount" or "therapeutically effective amount" are used interchangeably herein, and refer to an amount of a compound, formulation, material, or composition, as described herein effective to achieve a particular biological result, or to elicit a desired therapeutic response in at least a sub-population of subjects, for example, ameliorate the symptoms, alleviate conditions, slow or delay disease progression, or prevent a disease, at a reasonable benefit/risk ratio applicable to any medical treatment. In the context of administering a vaccine composition, an effective amount refers to an amount sufficient to induce an immune response or provide immunity against influenza virus, as compared to responses (or lack thereof) obtained without administration of the agent.

As used herein, the term "encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein, the term "epitope" or "antigenic epitope" includes any molecule, structure, amino acid sequence, or protein determinant that is recognized and specifically bound by a cognate binding molecule, such as an immunoglobulin, or other binding molecule, domain, or protein. Epitopic determinants generally contain chemically active surface groupings of molecules, such as amino acids or sugar side chains, and can have specific three-dimensional structural characteristics, as well as specific charge characteristics. Where an immunogen is or comprises a peptide or protein, the epitope can be comprised of consecutive amino acids (e.g., a linear epitope), or can be comprised of amino acids from different parts or regions of the protein that are brought into proximity by protein folding (e.g., a discontinuous or conformational epitope), or non-contiguous amino acids that are in close proximity irrespective of protein folding.

As used herein, the term "expression" is defined as the transcription and/or translation of a particular nucleotide sequence driven by a regulatory sequence such as a promoter and/or an enhancer.

The term "expression cassette" is a distinct component of vector DNA consisting of a gene and regulatory sequence to be expressed by a transfected cell. In each successful transformation, the expression cassette directs the cell's machinery to make RNA and protein(s). Some expression cassettes are designed for modular cloning of protein-encoding sequences so that the same cassette can easily be altered to make different proteins.

As used herein, the term "expression vector" refers to a composition of matter which comprises a nucleotide sequence encoding a protein and/or an RNA and which can be used to deliver the nucleic acid sequence to the interior of a cell and express the encoded protein and/or RNA inside the cell. An expression vector typically comprises a regulatory sequence for expression of the protein or RNA encoded by the nucleotide sequence, wherein the regulatory sequence is operably linked to the nucleotide sequence. Expression vectors include non-viral vectors, such as plasmids, phagemids, and cosmids, and viral vectors, such as adenovirus vectors, adeno-associated virus (AAV) vectors, and retrovirus vectors.

The term "functional variant" refers to a polypeptide or a polynucleotide that maintains one or more of the biological functions of an original polypeptide or a polynucleotide (also referred to as wild-type polypeptide or a polynucleotide). A functional variant is structurally similar or substantially structurally similar to a parent or reference compound of the present application, but differs, in some contexts slightly, in composition (e.g., one base, atom or functional group is different, added, or removed; or one or more amino acids are mutated, inserted, or deleted), such that the polypeptide or encoded polypeptide is capable of performing at least one function of the encoded parent polypeptide with at least 50% efficiency, preferably at least 55%, at least 60%, at least 70%, at least 75%, at least 80%, at least 85%, at least 90%, at least 95%, at least 96%, at least 97%, at least 98%, at least 99%, at least 99.9%, or at least 100% level of activity of the parent polypeptide. In some embodiments, a functional variant of an original polypeptide or polynucleotide maintains at least 20%, 30%, 40%, 50%, 60%, 70%, 80%, 90% or 95% of at least one biological function of the original polypeptide or polynucleotide.

The term a "functional portion" or "functional fragment" refers to a polypeptide or polynucleotide that comprises only a domain, motif, portion or fragment of a parent or reference compound, and the polypeptide or encoded polypeptide retains at least 50% activity associated with the domain, portion or fragment of the parent or reference compound, preferably at least 55%, at least 60%, at least 70%, at least 75%, at least 80%, at least 85%, at least 90%, at least 95%, at least 96%, at least 97%, at least 98%, at least 99%, at least 99.9%, or at least 100% level of activity of the parent polypeptide, or provides a biological benefit (e.g., effector function).

As used herein, the term "homology" refers to the overall relatedness between polymeric molecules, e.g. between nucleic acid molecules (e.g. DNA molecules and/or mRNA molecules) and/or between polypeptide molecules. In some embodiments, polymeric molecules are considered to be "homologous" to one another if their sequences are at least about 80%, 85%, 90%, 95%, 96%, 97%, 98%, 99%, 99.5% identical or similar. The term "homologous" necessarily refers to a comparison between at least two sequences (polynucleotide or polypeptide sequences). In accordance with the present invention, two polynucleotide sequences are considered to be homologous if the polypeptides they encode are at least about 80%, 90%, 95%, or even 99% to one another. In some embodiments, homologous polynucleotide sequences are characterized by the ability to encode a stretch of at least 4-5 uniquely specified amino acids.

As used herein, the term "identity" refers to the overall relatedness between polymeric molecules, e.g., between oligonucleotide molecules (e.g. DNA molecules and/or mRNA molecules) and/or between polypeptide molecules. Calculation of the percent identity of two polynucleotide/polypeptide sequences, for example, can be performed by aligning the two sequences for optimal comparison purposes (e.g., gaps can be introduced in one or both of a first and a second nucleic acid/amino acid sequences for optimal alignment and non-identical sequences can be disregarded for comparison purposes). In certain embodiments, the length of a sequence aligned for comparison purposes is at least about 80%, 90%, 95%, 96%, 97%, 98%, 99% or 100% identical to a reference sequence. The nucleotides at corresponding nucleotide/amino acid positions are then compared. When a position in the first sequence is occupied by the same nucleotide/amino acid as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. The percent identity between two nucleotide/amino acid sequences can be determined using conventional methods known in the art at the time the present invention was made.

As used herein, the term "immunogen" refers to a substance or molecule capable of eliciting an immune response and generating specific antibodies (humoral response) or cell-mediated response against the substance or molecule. As such, the immunogen is capable of being recognized by components of the immune system, such as lymphocytes. An immunogen can be as small as a single epitope, or larger, and can include multiple epitopes. As such, the size of an immunogen can be as small as about 5-12 amino acids (e.g., a peptide) and as large as a partial protein, a full-length protein, including a multimer and hybrid protein, or a chimeric protein. In addition, immunogens can be polynucleotides, such as mRNAs and DNAs, or carbohydrates or attenuated/killed pathogen. An immunogen may be from a bacterium, virus, protozoan or fungus. As used herein, the term a "variant" of an immunogen is a modified form of the original immunogen but maintains the immunogenicity of the original immunogen. For example, a variant of an HA or NA of a flu virus may have a protein sequence that differs from the original HA or NA, but is still capable of eliciting an immune response and generating specific antibodies (humoral response) or cell-mediated response against the original HA or NA.

The term "moiety", as used herein, relates to a part of a molecule that may include either whole functional groups or parts of functional groups as substructures. The term "moiety" further means part of a molecule that exhibits a particular set of chemical and/or pharmacologic characteristics which are similar to the corresponding molecule.

As used herein, the term "mRNA vaccine" or "mRNA vaccine construct" refers to a type of nucleic acid vaccines that uses messenger RNA (mRNA) to produce an immunogen specific immune response. The vaccine delivers molecules of immunogen-encoding mRNA into host cells, which use the designed mRNA as a blueprint to build foreign protein that would normally be produced by a pathogen (such as a virus).

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

The term "nucleotide sequence" or interchangeably "nucleic acid sequence" refers to a single- or double-stranded nucleic acid. It can be DNA or RNA. It can also be single-stranded or double-stranded DNA. It also includes all nucleotide sequences that are degenerate versions of each other and that encode the same amino acid sequence. Nucleotide sequences that encode proteins and RNA may include introns.

The terms "nucleobase complementarity" and "complementarity" refer to a nucleobase that is capable of base pairing with another nucleobase. For example, in DNA, adenine (A) is complementary to thymine (T). For example, in RNA, adenine (A) is complementary to uracil (U). When used in reference to an oligonucleotide or portion thereof, the term "fully complementary" means that each nucleobase of the oligonucleotide or portion thereof is capable of pairing with a nucleobase of a complementary nucleic acid or contiguous portion thereof. Thus, a fully complementary region comprises no mismatches or unhybridized nucleobases in either strand. The term "partially complementary" means that one or more nucleobase of the oligonucleotide or portion thereof is not capable of pairing with the nucleobase(s) at the corresponding position(s) of a complementary nucleic acid or contiguous portion thereof.

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

As used herein, the term "regulatory sequence" means a nucleic acid sequence which is required for expression of a coding sequence (either for protein or RNA) operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

The term "promoter" as used herein is defined as a DNA sequence recognized by the synthetic machinery of the cell, or introduced synthetic machinery, required to initiate the specific transcription of a polynucleotide sequence. A "constitutive" promoter is a nucleotide sequence which, when operably linked with a polynucleotide which encodes or specifies a gene product, causes the gene product to be produced in a cell under most or all physiological conditions of the cell. An "inducible" promoter is a nucleotide sequence which, when operably linked with a polynucleotide which encodes or specifies a gene product, causes the gene product to be produced in a cell substantially only when an inducer which corresponds to the promoter is present in the cell. A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

The terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, hybrid proteins, among others. A polypeptide includes a natural peptide, a recombinant peptide, or a combination thereof.

As used herein, the term "pharmaceutically acceptable carrier" refers to those compounds, materials, compositions that are, within the scope of sound medical judgment, suitable for use in contact with the tissues of human beings and animals without excessive toxicity, irritation, allergic response, or other problem or complication, commensurate with a reasonable benefit/risk ratio. Examples of pharmaceutically acceptable carrier include, but are not limited to, solvents, solubilizers, fillers, diluents, stabilizers, surfactants, binders, absorbents, bases, buffering agents, excipients, emulsifying agents, encapsulating materials, humectants, lubricants, gels, dispersion media, coatings, isotonic and absorption delaying agents. The use of such carriers and agents for pharmaceutically active substances is well-known in the art.

The phrase "pharmaceutically acceptable", as used in connection with compositions described herein, refers to molecular entities and other ingredients of such compositions that are physiologically tolerable and do not typically produce untoward reactions when administered to a mammal (e.g., a human). Preferably, the term "pharmaceutically acceptable" means approved by a regulatory agency of the Federal or a state government or listed in the U.S. Pharmacopeia or other generally recognized pharmacopeia for use in mammals, and more particularly in humans.

The term "pharmaceutically acceptable carrier or excipient" refers to a vehicle that does not produce a severe adverse, allergic or other untoward reaction when administered to a subject, especially a human, as appropriate. A pharmaceutically acceptable carrier or excipient refers to a non-toxic solid, semi-solid or liquid filler, diluent, encapsulating material or formulation auxiliary of any type.

The term "subject" or "patient" as used herein is intended to include animals including humans, apes, monkeys, dogs, cows, horses, pigs, sheep, goats, cats, mice, rabbits, rats, other mammals, poultry, fish, reptiles, and transgenic non-human animals.

As used herein, the term "substantially" refers to the qualitative condition of exhibiting total or near-total extent or degree of a characteristic or property of interest. In certain embodiments, the phrase "substantially full length" refers to a nucleic acid or protein that is at least about 80%, 85%, 90%, 91%, 92%, 93%, 94%, 95%, 96%, 97%, 98%, 99%, or 99.5% in length relative to a reference nucleic acid encoding an open reading frame or a reference protein. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

The terms "treat" or "treatment" of a state, disorder, disease, or condition include: (1) preventing, delaying, or reducing the incidence and/or likelihood of the appearance of at least one clinical or sub-clinical symptom of the state, disorder, disease, or condition developing in a subject that may be afflicted with or predisposed to the state, disorder, disease, or condition, but does not yet experience or display clinical or subclinical symptoms of the state, disorder, disease, or condition; or (2) inhibiting the state, disorder, disease, or condition, i.e., arresting, reducing or delaying the development of the disease or a relapse thereof or at least one clinical or sub-clinical symptom thereof; or (3) relieving the state, disorder, disease, or condition, i.e., causing regression of the state, disorder, disease, or condition or at least one of the clinical or sub-clinical symptoms of the state, disorder, disease, or condition. The benefit to a subject to be treated is either statistically significant or at least perceptible to the patient or to the physician.

Prevention and/or treatment of viral disease of the present application is applicable to a variety of viruses, viral immunogens, and viral diseases including, but not limited to, influenza viruses (including H1N1, H1N3, H3N2, H3N8, H5N1, H5N6, H7N9, influenza A, and influenza B), measles virus, rubella virus, meningitis B virus, Bunyavirales, Phenuiviridae, Peribunyaviridae, Bunyamwera virus, Hantaviridae, Nairoviridae, Hendra virus, Nipah virus, Pneumoviridae, Respiratory syncytial virus (RSV), and Orthopneumovirus.

As used herein, the term "vaccine" refers to a composition that induces an immune response in the recipient or host of the vaccine. A vaccine may induce a humoral (e.g., antibody, neutralizing antibody, other functional antibodies etc.) immune response to one or more immunogens, cell-mediated immune response (e.g., helper T lymphocyte, or cytotoxic T lymphocyte (CTL)) response against one or more immunogens, or both in a recipient so as to provide partial or complete protection against a current or subsequent pathogen infection or disease condition.

As used herein, the term "vaccination" refers to the administration of a vaccine to stimulate an individual's immune system to develop adaptive immunity to a pathogen.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. Further, if the disclosure describes "a composition comprising A and B", the disclosure also contemplates the alternative embodiments "a composition consisting of A and B" and "a composition consisting essentially of A and B".

Where ranges are given, endpoints are included. Further, it is to be understood that unless otherwise indicated or otherwise evident from the context and understanding of one of ordinary skill in the art, values that are expressed as ranges can assume any specific subrange within the stated ranges in different embodiments of the invention, or any subrange defined by any pair of integers within a stated range, unless the context clearly dictates otherwise.

It should also be understood that, unless clearly indicated to the contrary, in any methods claimed herein that include more than one step or act, the order of the steps or acts of the method is not necessarily limited to the order in which the steps or acts of the method are recited.

II. Polypeptides, Polynucleotides and Vaccine Composition of the Present Application

Hybrid Protein Comprising a NA and a Mutated HA

One aspect of the present application relates to a hybrid protein comprising a first domain and a second domain, wherein the second domain is located at the C-terminal of the first domain. In some embodiments, the hybrid protein further comprises a linker and/or foldon region that connects the first domain to the second domain. FIG. 1 shows a schematic of the general design of the hybrid protein of the present application.

In some embodiments, the first domain comprises a sequence encoding an ectodomain of a trimeric surface protein of an enveloped RNA virus. In some embodiments, the second domain comprises a sequence encoding an ectodomain of a type 2 transmembrane domain protein. In some embodiments, the hybrid protein further comprises a transmembrane domain of the trimeric surface protein and/or a transmembrane domain of the type 2 transmembrane domain protein. In some embodiments, the hybrid protein further comprises a cytoplasmic tail of the trimeric surface protein and/or a cytoplasmic tail of the type 2 transmembrane domain protein. In some embodiments, the hybrid protein further comprises an intracytoplasmic linker.

In some embodiments, the hybrid protein comprises a first domain comprising an ectodomain of a neuraminidase (NA) of a first virus, and second domain comprising a sequence encoding a mutated hemagglutinin (HA) of a second virus, wherein the mutated HA comprises a mutation that reduces aggregation and non-specific binding to sialic acid. In some embodiments, the first virus is the same as the second virus. In some embodiments, the first virus is different from the second virus. In some embodiments, the hybrid protein further comprises a linker and/or foldon sequence. In some embodiments, the hybrid protein further comprises a tag sequence. In some embodiments, the second domain is located at the C-terminal of the first domain.

Neuraminidase is an enzyme found on the surface of certain viruses, such as influenza viruses, that plays a crucial role in the virus's ability to infect cells and spread. It helps the virus detach from and move away from infected cells, allowing it to infect other cells and propagate the infection. Neuraminidase also assists the virus in penetrating the mucus layer in the respiratory tract, facilitating its attachment to host cells.

Hemagglutinin (HA) is a protein found on the surface of certain viruses that plays a crucial role in viral entry and infection. It's responsible for binding the virus to host cells and mediating the fusion of viral and cellular membranes, allowing the virus to release its genetic material into the host cell. HA is also a key immunogen for vaccine development. Hemagglutinin vaccine, specifically for influenza, utilizes the HA protein of the influenza virus to stimulate an immune response and to produce neutralizing antibodies that can block the virus from infecting cells, thus preventing or lessening the severity of influenza infection.

The present application presents an unexpected effect that expression of the ectodomain of NA, or an equivalent thereof, provides an adjuvant effect to expand the immunogenicity of the HA and hence introduces a more effective immune response against the HA. In some embodiments, the NA and HA are from the same virus. In some embodiments, the NA and HA are from different viruses.

In some embodiments, the NA is from a virus of orthomyxoviridae. In some embodiments, the NA is from a H5N1 virus, H3N2 virus, H1N1 virus, influenza A virus or influenza B subtype virus. In some embodiments, the neuraminidase is a N1 neuraminidase.

In some embodiments, the NA, or equivalent thereof, is from a virus of paramyxoviridae. In some embodiments, the paramyxoviridae NA equivalent is a G protein (G), paramyxovirus hemagglutinin (H), or hemagglutinin-neuraminidase (HN). In some embodiments, the NA is from a mumps virus.

In some embodiments, the HA is from a virus of orthomyxoviridae. In some embodiments, the HA is from H5N1 virus, H3N2 virus, H1N1 virus, influenza A virus or influenza B subtype virus. In some embodiments, the HA is from a virus of paramyxoviridae. In some embodiments, the HA is from a rubella virus.

In some embodiments, the mutated HA is a mutated HA of H5N1 and wherein the mutation is a modification of the tyrosine (Y) at position 107 to phenylalanine (F) (i.e., position 91 of the mature H5N1 HA protein). In some embodiments, the hybrid protein comprises SEQ ID NO:1. In some embodiments, the hybrid protein comprises SEQ ID NO:13.

In some embodiments, hybrid protein of the present application comprises an amino acid sequence having at least at least 75%, 80%, at least 85%, at least 90%, at least 95%, at least 96%, at least 97%, at least 98%, or at least 99%, but less than 100% sequence identity to SEQ ID NO:1.

In a specific embodiment, the hybrid protein of the present application is a protein sequence encoding the ectodomain of H5 2.2.3.4b influenza virus A stabilized with a C-terminal trimerization domain and leading downstream to 3 monomers of the N1 neuraminidase (NA) ectodomain connected to the trimerization domain at the N-terminus. The HA (hemagglutinin) includes a modification of the tyrosine at position 91 of the mature protein (without the 16 aa signal peptide) to phenylalanine to reduce aggregation and non-specific binding to sialic acid.

The sequence is based on the H5N1 virus isolated from a subject infected through exposure to infected dairy cattle.

In some embodiments, the mutated HA comprises the polybasic furin cleavage site between HA1 and HA2. In some other embodiments, the polybasic furin cleavage site between HA1 and HA2 in the mutated HA is replaced with a linker/tag sequence to prevent cleavage between HA1 and HA2. The trimerization domain can be a foldon domain (i.e., the 27-residue β-propeller-like trimeric structure found at the C terminus of bacteriophage T4 fibritin) or GCN4 leucine-zipper domain or other trimerization domain variant. The mutated HA may or may not contain the furin cleavage site. In some embodiments, the mutated HA contains the furin cleavage site. In some embodiments, the furin cleavage site of mutated HA is replaced with a linker sequence. In some embodiments, the linker sequence has a length of 4-12 amino acids. Examples of the linker sequences include, but are not limited to, repeats of gly and ser, such as GGGGS (SEQ ID NO: 14), or repeats of gly-ser (GS), such as GSGS (SEQ ID NO: 15).

The protein sequence of a proposed H5N1 vaccine antigen is shown in SEQ ID NO:1, which contains a signal peptide (SEQ ID NO:2, aa 1-16 of the HA of the H5N1 strain A/Texas/37/2024) a mutated HA1 domain (SEQ ID NO:3, aa 17-345 of the HA of the H5N1 strain A/Texas/37/2024, with a Y to F substitution at position 107 (Y107F), which corresponds to position 91 in the mature HA protein), a HA2 domain (SEQ ID NO:4, aa 346-532 of the HA of the H5N1 strain A/Texas/37/2024, a foldon/linker region of 33 amino acid residues (SEQ ID NO:5) and the ectodomain of a NA (SEQ ID NO:6, aa 36-469 of the NA of the H5N1 strain A/Texas/37/2024). Selected regions are highlighted including the signal peptide (MENIVLLLAIVSLVKS, SEQ ID NO:2), Y107F, polybasic cleavage site (KRRKR, SEQ ID NO:12), and trimerization domain between HA and NA (SAIGGYIPEAPRDGQAYVRKDGEWVLLSTF, SEQ ID NO:5). In some embodiments, the vaccine antigen further comprises a linker/thrombin/his tag/strep tag sequence of GGLVPRGSHHHHHHSAWSHPQFEK (SEQ ID NO:11).

The complete protein sequence of the HA protein of the wild-type H5N1 strain A/Texas/37/2024 is shown in SEQ ID NO:7. The complete nucleotide sequence encoding the HA protein of the wild-type H5N1 strain A/Texas/37/2024 is shown in SEQ ID NO:8.

The complete protein sequence of the NA protein of the wild-type H5N1 strain A/Texas/37/2024 is shown in SEQ ID NO:9. The complete nucleotide sequence encoding the NA protein of the wild-type H5N1 strain A/Texas/37/2024 is shown in SEQ ID NO:10.

In some embodiments, the hybrid protein further comprises a tag sequence, such as thrombin tag, his tag or strep tag. An example of a linker/thrombin/his tag/strep tag sequence is shown in SEQ ID NO:11.

In some embodiments, the hybrid protein of the present application comprises a first domain comprising an amino acid sequence having at least 80%, at least 85%, at least 90%, at least 95%, at least 96%, at least 97%, at least 98%, or at least 99% sequence identity to SEQ ID NO:7 and/or a second domain comprising an amino acid sequence having at least 80%, at least 85%, at least 90%, at least 95%, at least 96%, at least 97%, at least 98%, or at least 99% sequence identity to SEQ ID NO:6.

In some embodiments, the hybrid protein of the present application comprises a second domain that has neuraminidase activity. In some embodiments, the second domain is derived from the NA protein of the wild-type H5N1 strain A/Texas/37/2024 and forms an NA enzymatic site surrounded by protein loops and the residues Arg118, Asp151, Arg152, Arg224, Glu276, Arg292, Arg371 and Tyr406 of the wild-type H5N1 strain A/Texas/37/2024 NA protein. In some embodiments, the second domain is derived from the NA protein of the wild-type H5N1 strain A/Texas/37/2024 and forms a sialic acid binding site with residues Ser367, Ser370, Ser372, Asn400, Trp403 and Lys432 of the wild-type H5N1 strain A/Texas/37/2024 NA protein.

This general design shown in FIG. 1 could be used for any influenza A or influenza B virus and could produce a vaccine antigen that could be delivered by mRNA or as a protein. It could be used as a vaccine for humans or animals. In addition to an approach for immediate pandemic response with a sequence matching the outbreak strain, it may also be an effective approach for producing improved seasonal influenza vaccines by combining appropriate H1N1, H3N2, and B sequences.

Hybrid Protein Comprising an Immunogen and an NA

Another aspect of the present application relates to a hybrid protein comprising a first domain comprising a sequence encoding an immunogen from a first virus, and a second domain comprising a sequence encoding an ectodomain of a NA of a second virus. In some embodiments, the second domain is located at the C-terminal of the first domain.

In some embodiments, the first virus and the second virus are the same virus, such as an influenza virus. In some embodiments, the first virus and the second virus are different viruses. In some embodiments, the ectodomain of the NA is derived from a protein with neuraminidase activity from any enveloped virus that has a neuraminidase that is a type 2 transmembrane protein.

The inventors unexpectedly found that the covalently attached NA has adjuvant or targeting effects that may improve adaptive immune responses to the immunogen encoded by the second domain.

In some embodiments, the first virus is selected from the group consisting of orthomyxoviruses (such as influenza viruses), paramyxoviruses, pneumoviruses, retroviruses (such as HIV), filoviruses (such as Ebola), coronaviruses, and arenaviruses (such as Lassa) and the second virus is an orthomyxovirus (such as an influenza virus). In some embodiments, the immunogen is selected from the group consisting of an HA from an orthomyxovirus, an F protein from a paramyxovirus, an F protein from a pneumovirus, an Env protein from a retrovirus, a GP from a filovirus, a spike protein from a coronavirus, and a spike complex of an arenavirus. In some embodiments, the immunogen is a surface protein from a measles virus, a mumps virus or a rubella virus.

Hybrid Protein Comprising an Immunogen and a Type 2 Transmembrane Domain

Another aspect of the present application relates to a hybrid protein comprising a first domain comprising a sequence encoding an immunogen from a first virus, and a second domain comprising a sequence from a type 2 transmembrane domain protein of a second virus. In some embodiments, the second domain is located at the C-terminal of the first domain. In some embodiments, the first virus and the second virus are the same virus. In some embodiments, the first virus and the second virus are different viruses. In some embodiments, the immunogen is an F protein of an RSV or human metapneumovirus and the type 2 transmembrane domain protein is a G protein of an RSV or human metapneumovirus.

The present application provides an approach for rapid and scalable vaccine development in response to pandemic influenza. Currently licensed vaccines are made by inactivating influenza virus grown in eggs or cell culture, subunit HA protein, or live virus grown in eggs. These manufacturing approaches require at least 4-5 months before deployment and are not easily scaled to the level needed for a global vaccine campaign. It may also provide an approach to improving seasonal influenza vaccines which is a national priority described in Presidential proclamations specific for influenza vaccine development and documents outlining pandemic preparedness plans.

Polynucleotide Encoding the Hybrid Protein of the Present Application

Another aspect of the present application relates to a polynucleotide comprising a sequence encoding the hybrid protein of the present application. In some embodiments, the polynucleotide is a DNA molecule. In some embodiments, the polynucleotide is an RNA molecule. In some embodiments, the polynucleotide is a mRNA molecule. In some embodiments, the polynucleotide comprises an expression cassette that comprises (1) a nucleotide sequence encoding the hybrid protein of the present application and (2) a regulatory element operably linked to the nucleotide sequence encoding the hybrid protein of the present application.

Expression Vectors

Another aspect of the present application relates to an expression vector that comprises the polynucleotide of the present application. In some embodiments, the expression vector is a non-viral vector, such as a plasmid. In some embodiments, the expression vector is a viral vector.

Any suitable expression vector may be used to introduce and express the hybrid proteins of the present application in a host cell. As used herein, the term "expression vector" includes any nucleic acid capable of expressing the hybrid protein in vivo. Expression vectors may be delivered to cells using two primary delivery schemes: viral-based delivery systems using viral vectors and non-viral based delivery systems using, for example, plasmid vectors. Such methods are well known in the art and readily adaptable for use with the compositions and methods described herein. In certain cases, these methods can be used to target certain diseases and cell populations by using the targeting characteristics inherent to the carrier or engineered into the carrier.

Regulatory Elements

The expression vector contains one or more transcriptional regulatory elements, including promoters and/or enhancers, for directing the expression of hybrid proteins. A promoter comprises a DNA sequence that functions to initiate transcription from a relatively fixed location in regard to the transcription start site. A promoter contains core elements required for basic interaction of RNA polymerase and transcription factors and may operate in conjunction with other upstream elements and response elements.

As used herein, the term "promoter" is to be taken in its broadest context and includes transcriptional regulatory elements (TREs) from genomic genes or chimeric TREs therefrom, including the TATA box or initiator element for accurate transcription initiation, with or without additional TREs (i.e., upstream activating sequences, transcription factor binding sites, enhancers, and silencers) which regulate activation or repression of genes operably linked thereto in response to developmental and/or external stimuli, and trans-acting regulatory proteins or nucleic acids. The promoter may be constitutively active, or it may be active in one or more tissues or cell types in a developmentally regulated manner. A promoter may contain a genomic fragment, or it may contain a chimera of one or more TREs combined together.

Preferred promoters are those capable of directing expression in a target cell of interest. The promoters may include constitutive promoters (e.g., HCMV, SV40, elongation factor-1$\alpha$ (EF-1$\alpha$)) or those exhibiting preferential expression in a particular cell type of interest.

Enhancers generally refer to DNA sequences that function away from the transcription start site and can be either 5' or 3' to the transcription unit. Furthermore, enhancers can be within an intron as well as within the coding sequence. They are usually between 10 and 300 bp in length, and they function in cis. Enhancers function to increase and/or regulate transcription from nearby promoters. Preferred enhancers are those directing high-level expression in the virus expressing cell.

The promoter and/or enhancer may be specifically activated either by light or specific chemical inducing agents. In some embodiments, inducible expression systems regulated by administration of tetracycline or dexamethasone, for example, may be used. In other embodiments, gene expression may be enhanced by exposure to radiation, including gamma irradiation and external beam radiotherapy (EBRT), or alkylating chemotherapeutic drugs. Cell or tissue-specific transcriptional regulatory elements (TREs) can be incorporated into expression vectors to allow for transcriptional targeting of expression to desired cell types.

Other Elements

Expression vectors generally contain sequences, such as the poly(A) sequences, for transcriptional termination, and may additionally contain one or more elements positively affecting mRNA stability. An expression vector may further include an internal ribosome entry site (IRES) between adjacent protein coding regions to facilitate expression two or more proteins from a common mRNA in an infected or transfected cell. Additionally, the expression vectors may further include nucleic acid sequence encoding a marker product. This marker product is used to determine if the gene has been delivered to the cell and once delivered is being expressed. Preferred marker genes are the *E. coli* lacZ gene, which encodes ß-galactosidase, and green fluorescent protein.

The expression vector can be introduced into the viral vector-producing cells by any conventional method, such as by naked DNA technique, cationic lipid-mediated transfection, polymer-mediated transfection, peptide-mediated transfection, virus-mediated infection, physical or chemical agents or treatments, electroporation, etc. In one embodiment, cells transfected with the vector may be used directly as a source of viral vectors (transient transfection). Alternatively, cells may be transfected with a vector expressing a hybrid protein along with a selectable marker facilitating selection of stably transformed clones expressing the hybrid protein. The viral vectors produced by such cells may be collected and/or purified according to techniques known in the art, such as by centrifugation, chromatography, etc. as further described in the cited references and Examples herein.

The expression vector can also include additional expression elements, for example, to improve the efficiency of translation. These signals can include, e.g., an ATG initiation codon and adjacent sequences. In some cases, for example, a translation initiation codon and associated sequence elements are inserted into the appropriate expression vector simultaneously with the polynucleotide sequence of interest (e.g., a native start codon). In such cases, additional translational control signals are not required. However, in cases where only a polypeptide coding sequence, or a portion thereof, is inserted, exogenous translational control signals, including an ATG initiation codon is provided. The initiation codon is placed in the correct reading frame to ensure translation of the polynucleotide sequence of interest. Exogenous transcriptional elements and initiation codons can be of various origins, both natural and synthetic.

Viral Vectors

In some embodiments, a hybrid protein or hybrid proteins of the present application are delivered from viral-derived expression vectors. Exemplary viral vectors may include or be derived from adenoviruses, adeno-associated viruses, herpesviruses, vaccinia virus (or other poxviruses), polioviruses, poxviruses, HIV virus, lentiviruses, retroviruses, Sindbis and other RNA viruses, and the like. Also preferred are any viral families which share the properties of these viruses which make them suitable for use as vectors. Retroviruses include Murine Moloney Leukemia virus (MMLV), HIV and other lentivirus vectors. Adenovirus vectors are relatively stable and easy to work with, have high titers, and can be delivered in aerosol formulation, and can transfect non-dividing cells. Poxviral vectors are large and have several sites for inserting genes, they are thermostable and can be stored at room temperature. Viral delivery systems typically utilize viral vectors having one or more genes removed and with an exogenous gene and/or gene/promoter cassette being inserted into the viral genome in place of the removed viral DNA. The necessary functions of the removed gene(s) may be supplied by cell lines which have been engineered to express the gene products of the early genes in trans.

Retroviral Vectors

A retrovirus is an animal virus belonging to the virus family of Retroviridae, including any types, subfamilies, genus, or tropisms. Examples of methods for using retroviral vectors for gene therapy are described in U.S. Pat. Nos. 4,868,116 and 4,980,286; PCT applications WO 90/02806 and WO 89/07136; and Mulligan, (Science 260:926-932 (1993)); the teachings of which are incorporated herein by reference.

Adenoviral Vectors

Recombinant adenoviruses have been shown to achieve high efficiency gene transfer after direct, in vivo delivery to airway epithelium, hepatocytes, vascular endothelium, CNS parenchyma and a number of other tissue sites. Recombinant adenoviruses achieve gene transduction by binding to specific cell surface receptors, after which the virus is internalized by receptor-mediated endocytosis, in the same manner as wild type or replication-defective adenovirus.

A viral vector can be one based on an adenovirus which has had one or more viral genes removed and these virions are generated in a complement cell line, such as the human 293 cell line. In one embodiment, the E1 gene is removed from the adenoviral vector. In another embodiment, both the E1 and E3 genes are removed from the adenoviral vector. In another embodiment, both the E1 and E4 genes are removed from the adenoviral vector. In another embodiment, the adenovirus vector is a gutless adenovirus vector.

Adeno-Associated Viral Vectors

Another type of viral vector is based on an adeno-associated virus (AAV). This defective parvovirus is a preferred vector because it can infect many cell types and is nonpathogenic to humans. AAV type vectors can transport about 4 to 5 kb and wild type AAV is known to stably insert into chromosome 19. Vectors which contain this site specific integration property are preferred. An especially preferred embodiment of this type of vector is the P4.1 C vector produced by Avigen, San Francisco, Calif., which can contain the herpes simplex virus thymidine kinase gene, HSV-tk, and/or a marker gene, such as the gene encoding the green fluorescent protein, GFP.

In another type of AAV virus, the AAV contains a pair of inverted terminal repeats (ITRs) which flank at least one cassette containing a promoter which directs cell-specific expression operably linked to a heterologous gene. Heterologous in this context refers to any nucleotide sequence or gene which is not native to the AAV or B19 parvovirus.

Typically, the AAV and B19 coding regions have been deleted, resulting in a safe, noncytotoxic vector. The AAV ITRs, or modifications thereof, confer infectivity and site-specific integration, but not cytotoxicity, and the promoter directs cell-specific expression. U.S. Pat. No. 6,261,834 is herein incorporated by reference for material related to the AAV vector.

Large Payload Viral Vectors

Molecular genetic experiments with large human herpes viruses have provided a means whereby large heterologous DNA fragments can be cloned, propagated and established in cells permissive for infection with herpes viruses (Sun et al., Nature genetics 8: 33-41, 1994; Cotter and Robertson, Curr Opin Mol Ther 5: 633-644, 1999). These large DNA viruses (herpes simplex virus (HSV) and Epstein-Barr virus (EBV), have the potential to deliver fragments of human heterologous DNA>150 kb to specific cells. EBV recombinants can maintain large pieces of DNA in the infected B-cells as episomal DNA. Individual clones carried human genomic inserts up to 330 kb appeared genetically stable. The maintenance of these episomes requires a specific EBV nuclear protein, EBNA1, constitutively expressed during infection with EBV. Additionally, these vectors can be used for transfection, where large amounts of protein can be generated transiently in vitro. Herpesvirus amplicon systems are also being used to package pieces of DNA>220 kb and to infect cells that can stably maintain DNA as episomes. Other useful systems include, for example, replicating and host-restricted non-replicating vaccinia virus vectors.

Non-Viral Vectors

Non-Viral vectors include DNA expression vectors and mRNA expression vectors. DNA expression vectors are typically plasmid vectors that include a circular double-stranded DNA loop into which additional DNA segments encoding the hybrid protein of the present application can be inserted.

mRNA Vectors

In some embodiments, a hybrid protein of the present application is administered in the form of a mRNA or a modified mRNA, wherein the modification preferably leads to a stabilized mRNA construct. In some embodiments, the stabilized mRNA is resistant to in vivo degradation (e.g. by an exo- or endo-nuclease). Such stabilization can be effected, for example, by a modified phosphate backbone of the mRNA of the present application. A backbone modification in connection with the present application is a modification in which phosphates of the backbone of the nucleotides contained in the mRNA are chemically modified. Nucleotides that may be preferably used in this connection contain e.g. a phosphorothioate-modified phosphate backbone, preferably at least one of the phosphate oxygens contained in the phosphate backbone being replaced by a sulfur atom. Stabilized mRNAs may further include, for example: non-ionic phosphate analogues, such as, for example, alkyl and aryl phosphonates, in which the charged phosphonate oxygen is replaced by an alkyl or aryl group, or phosphodiesters and alkylphosphotriesters, in which the charged oxygen residue is present in alkylated form. Such backbone modifications typically include, without implying any limitation, modifications from the group consisting of methylphosphonates, phosphoramidates and phosphorothioates (e.g. cytidine-5'-0-(1-thiophosphate)). In some embodiments, the RNA sequence is modified to maintain the encoded amino acid sequence, but has a secondary structure that results in a more stable RNA molecule or one that is more easily packaged or transcribed.

In some embodiments, the mRNA encoding the hybrid protein of the present application is stabilized against degradation by RNases by the addition of a so-called "5' cap" structure. Particular preference is given in this connection to an m7G(5')ppp (5'(A,G(5')ppp(5')A or G(5')ppp(5')G as the 5' cap" structure. However, such a modification is introduced only if a modification, for example a lipid modification, has not already been introduced at the 5' end of the mRNA of the inventive composition or if the modification does not interfere with the immunogenic properties of the (unmodified or chemically modified) mRNA In some embodiments, the mRNA encoding the hybrid protein of the present application contains sugar modifications. A sugar modification in connection with the present application is a chemical modification of the sugar of the nucleotides of the at least one mRNA and typically includes, without implying any limitation, sugar modifications selected from the group consisting of 2'-deoxy-2'-fluoro-oligoribonucleotide (2'-fluoro-2'-deoxycytidine-5'-triphosphate, 2'-fluoro-2'-deoxyuridine-5'-triphosphate), 2'-deoxy-2'-deamine oligoribonucleotide (2'-amino-2'-deoxycytidine-5'-triphosphate, 2'-amino-2'-deoxyuridine-5'-triphosphate), 2'-0-alkyl oligoribonucleotide, 2'-deoxy-2'-C-alkyl oligoribonucleotide (2'-0-methylcytidine-5'-triphosphate, 2'-methyluridine-5'-triphosphate), 2'-C-alkyl oligoribonucleotide, and isomers thereof (2'-aracytidine-5'-triphosphate, 2'-arauridine-5'-triphosphate), or azidotriphosphate (2'-azido-2'-deoxycytidine-5'-triphosphate, 2'-azido-2'-deoxyuridine-5'-triphosphate).

In some embodiments, the mRNA encoding the hybrid protein of the present application additionally or alternatively also contains at least one base modification, which is preferably suitable for increasing the expression of the at least one protein coded for by the at least one mRNA sequence significantly as compared with the unaltered, i.e. natural (=native), mRNA sequence. Significant in this case means an increase in the expression of the protein compared with the expression of the native mRNA sequence by at least 20%, preferably at least 30%, 40%, 50% or 60%, more preferably by at least 70%, 80%, 90% or even 1 00% and most preferably by at least 150%, 200% or even 300% or more. In connection with the present application, a nucleotide having such a base modification is preferably selected from the group of the base-modified nucleotides consisting of 2-amino-6-chloropurineriboside-5'-triphosphate, 2-aminoadenosine-5'-triphosphate, 2-thiocytidine-5'-triphosphate, 2-thiouridine-5'-triphosphate, 4-thiouridine-5'-triphosphate, 5-aminoallylcytidine-5'-triphosphate, 5-aminoallyluridine-5'-triphosphate, 5-bromocytidine-5'-triphosphate, 5-bromouridine-5'-triphosphate, 5-iodocytidine-5'-triphosphate, 5-iodouridine-5'-triphosphate, 5-methylcytidine-5'-triphosphate, 5-methyluridine-5'-triphosphate, 6-azacytidine-5'-triphosphate, 6-azauridine-5'-triphosphate, 6-chloropurineriboside-5'-triphosphate, 7-deazaadenosine-5'-triphosphate, 7-deazaguanosine-5'-triphosphate, 8-azaadenosine-5'-triphosphate, 8-azidoadenosine-5'-triphosphate, benzimidazole-riboside-5'-triphosphate, N1-methyladenosine-5'-triphosphate, N1-methylguanosine-5'-triphosphate, N6-methyladenosine-5'-triphosphate, 06-methylguanosine-5'-triphosphate, pseudouridine-5'-triphosphate, or puromycin-5'-triphosphate, xanthosine-5'-triphosphate. Particular preference is given to nucleotides for base modifications selected from the group of base-modified nucleotides consisting of 5-methylcytidine-5'-triphosphate, 7-deazaguanosine-5'-triphosphate, 5-bromocytidine-5'-triphosphate, and pseudouridine-5'-triphosphate.

In some embodiments, the mRNA encoding the hybrid protein of the present application is modified (and preferably stabilized) by introducing further modified nucleotides containing modifications of their ribose or base moieties. Generally, the at least one mRNA of the composition of the present application may contain any native (=naturally occurring) nucleotide, e.g. guanosine, uracil, adenosine, and/or cytosine or an analogue thereof. In this connection, nucleotide analogues are defined as non-natively occurring variants of naturally occurring nucleotides. Accordingly, analogues are chemically derivatized nucleotides with non-natively occurring functional groups, which are preferably added to or deleted from the naturally occurring nucleotide or which substitute the naturally occurring functional groups of a nucleotide. Accordingly, each component of the naturally occurring nucleotide may be modified, namely the base component, the sugar (ribose) component and/or the phosphate component forming the backbone (see above) of the mRNA sequence. Analogues of guanosine, uracil, adenosine, and cytosine include, without implying any limitation, any naturally occurring or non-naturally occurring guanosine, uracil, adenosine, thymidine or cytosine that has been altered chemically, for example by acetylation, methylation, hydroxylation, etc., including 1-methyl-adenosine, 1-methyl-guanosine, 1-methyl-inosine, 2,2-dimethyl-guanosine, 2,6-diaminopurine, 2'-Amino-2'-deoxyadenosine, 2'-Amino-2'-deoxycytidine, 2'-Amino-2'-deoxyguanosine, 2'-Amino-2'-deoxyuridine, 2-Amino-6-chloropurineriboside, 2-Aminopurine-riboside, 2'-Araadenosine, 2'-Aracytidine, 2'-Arauridine, 2'-Azido-2'-deoxyadenosine, 2'-Azido-2'-deoxycytidine, 2'-Azido-2'-deoxyguanosine, 2'-Azido-2'-deoxyuridine, 2-Chloroadenosine, 2'-Fluoro-2'-deoxyadenosine, 2'-Fluoro-2'-deoxycytidine, 2'-Fluoro-2'-deoxyguanosine, 2'-Fluoro-2'-deoxyuridine, 2'-Fluorothymidine, 2-methyl-adenosine, 2-methyl-guanosine, 2-methyl-thio-N6-isopenenyl-adenosine, 2'-O-Methyl-2-aminoadenosine, 2'-O-Methyl-2'-deoxyadenosine, 2'-O-Methyl-2'-deoxycytidine, 2'-O-Methyl-2'-deoxyguanosine, 2'-O-Methyl-2'-deoxyuridine, 2'-0-Methyl-5-methyluridine, 2'-O-Methylinosine, 2'-O-Methylpseudouridine, 2-Thiocytidine, 2-thio-cytosine, 3-methyl-cytosine, 4-acetyl-cytosine, 4-Thiouridine, 5-(carboxyhydroxymethyl)-uracil, 5,6-Dihydrouridine, 5-Aminoallylcytidine, 5-Aminoallyl-deoxy-uridine, 5-Bromouridine, 5-carboxymehtylaminomethyl-2-thio-uracil, 5-carboxymethylaminomethyl-uracil, 5-Chloro-Ara-cytosine, 5-Fluorouridine, 5-lodouridine, 5-methoxycarbonylmethyl-uridine, 5-methoxy-uridine, 5-methyl-2-thio-uridine, 6-Azacytidine, 6-Azauridine, 6-Chloro-7-deaza-guanosine, 6-Chloropurineriboside, 6-Mercapto-guanosine, 6-Methyl-mercaptopurine-riboside, 7-Deaza-2'-deoxy-guanosine, 7-Deazaadenosine, 7-methyl-guanosine, 8-Azaadenosine, 8-Bromo-adenosine, 8-Bromo-guanosine, 8-Mercapto-guanosine, 8-Oxoguanosine, Benzimidazole-riboside, Beta-D-mannosyl-queosine, Dihydro-uracil, Inosine, N1-Methyladenosine, N6-([6-Aminohexyl]carbamoylmethyl)-adenosine, N6-isopentenyl-adenosine, N6-methyl-adenosine, N7-Methyl-xanthosine, N-uracil-5-oxyacetic acid methyl ester, Puromycin, Queosine, Uracil-5-oxyacetic acid, Uracil-5-oxyacetic acid methyl ester, Wybutoxosine, Xanthosine, and Xylo-adenosine. The preparation of such analogues is known to a person skilled in the art, for example from U.S. Pat. No. 4,373,071, 4,401,796, 4,415,732, 4,458,066, 4,500,707, 4,668,777, 4,973,679, 5,047,524, 5,132,418, 5,153,319, 5,262,530 and 5,700,642. In the case of an analogue as described above, particular preference may be given according to the application to those analogues that increase the immunogenicity of the mRNA of the inventive composition and/or do not interfere with a further modification of the mRNA that has been introduced.

In some embodiments, the mRNA encoding the hybrid protein of the present application contains a lipid modification. Such a lipid-modified mRNA typically comprises an mRNA as defined herein, encoding at least one of the six antigens as defined above. Such a lipid-modified mRNA typically further comprises at least one linker covalently linked with that mRNA, and at least one lipid covalently linked with the respective linker. Alternatively, the lipid-modified mRNA comprises an (at least one) mRNA as defined herein and at least one (bifunctional) lipid covalently linked (without a linker) with that mRNA. According to a third alternative, the lipid-modified mRNA comprises an mRNA as defined herein, at least one linker covalently linked with that mRNA, and at least one lipid covalently linked with the respective linker, and also at least one (bifunctional) lipid covalently linked (without a linker) with that mRNA.

In some embodiments, the lipid contained in the mRNA of the present application (complexed or covalently bound thereto) is a lipid or a lipophilic residue that preferably is itself biologically active. Such lipids preferably include natural substances or compounds such as, for example, vitamins, e.g. alpha-tocopherol (vitamin E), including RRR-alpha-tocopherol (formerly D-alpha-tocopherol), L-alpha-tocopherol, the racemate D,L-alpha-tocopherol, vitamin E succinate (VES), or vitamin A and its derivatives, e.g. retinoic acid, retinol, vitamin D and its derivatives, e.g. vitamin D and also the ergosterol precursors thereof, vitamin E and its derivatives, vitamin K and its derivatives, e.g. vitamin K and related quinone or phytol compounds, or steroids, such as bile acids, for example cholic acid, deoxycholic acid, dehydrocholic acid, cortisone, digoxygenin, testosterone, cholesterol or thiocholesterol. Further lipids or lipophilic residues within the scope of the present application include, without implying any limitation, polyalkylene glycols (Oberhauser et al., Nucl. Acids Res., 1 992, 20, 533), aliphatic groups such as, for example, C1-C20-alkanes, C1-C20-alkenes or C1-C20-alkanol compounds, etc., such as, for example, dodecanediol, hexadecanol or undecyl residues (Saison-Behmoaras et al., EMBO J, 1991, 10, 111; Kabanov et al., FEBS Lett., 1990, 259, 327; Svinarchuk et al., Biochimie, 1 993, 75, 49), phospholipids such as, for example, phosphatidylglycerol, diacylphosphatidylglycerol, phosphatidylcholine, dipalmitoylphosphatidylcholine, distearoylphosphatidylcholine, phosphatidylserine, phosphatidylethanolamine, di-hexadecyl-rac-glycerol, sphingolipids, cerebrosides, gangliosides, or triethylammonium 1,2-di-0-hexadecyl-rac-glycero-3-H-phosphonate (Manoharan et al., Tetrahedron Lett., 1 995, 36, 3651; Shea et al., Nucl. Acids Res., 1 990, 18, 3777), polyamines or polyalkylene glycols, such as, for example, polyethylene glycol (PEG) (Manoharan et al., Nucleosides & Nucleotides, 1 995, 14, 969), hexaethylene glycol (HEG), palmitin or palmityl residues (Mishra et al., Biochim. Biophys. Acta, 1 995, 1264, 229), octadecylamines or hexylamino-carbonyl-oxycholesterol residues (Crooke et al., J. Pharmacol. Exp. Ther., 1996, 277, 923), and also waxes, terpenes, alicyclic hydrocarbons, saturated and mono- or poly-unsaturated fatty acid residues, etc.

Pharmaceutical or Vaccine Composition

Another aspect of the present application relates to a pharmaceutical composition or vaccine that comprises (1) a hybrid protein of the present application and/or an expression vector of the present application, and (2) a pharmaceutically acceptable carrier.

Exemplary "pharmaceutically acceptable carriers" include, but are not limited to, any and all solvents, solubilizers, fillers, diluents, stabilizers, surfactants, binders, absorbents, bases, buffering agents, excipients, lubricants, controlled release vehicles, diluents, emulsifying agents, encapsulating materials, humectants, lubricants, gels, dispersion media, coatings, antibacterial or antifungal agents, isotonic and absorption delaying agents, and the like, compatible with pharmaceutical administration. The use of such carriers and agents for pharmaceutically active substances is well-known in the art.

The medium in which the polypeptides and polynucleotides in the vaccine compositions are formulated to be physiologically acceptable. Suitable pharmaceutically acceptable carriers include sterile water, saline, dextrose, glucose, or other buffered solutions (e.g., phosphate buffered saline). Included in the medium can be physiologically acceptable preservatives, stabilizers, diluents, emulsifying agents, pH buffering agents, viscosity enhancing agents, colors, etc. For example, solutions or suspensions used for administration can include the following components: a sterile diluent such as water for injection, saline solution, fixed oils, polyethylene glycols, glycerin; propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose, pH can be adjusted with acids or bases, such as hydrochloric acid or sodium hydroxide.

In some embodiments, the pharmaceutical or vaccine composition of the present application further comprises, or is administered in combination with, one or more adjuvants. Adjuvants may be used in combination with the vaccine composition of the present application to e.g., improve stability and uptake, improve immune induction, enhance an immune response, but is not antigenic itself when administered in the absence of an antigen. Additionally, an adjuvant may decrease the dosage required to induce an effective immune response. Exemplary adjuvants include, but are not limited to, mineral salts, complete and incomplete Freund's adjuvant, squalene based adjuvants, saponins based adjuvants, toll-like receptor (TLR) ligands, microbial derivatives, and cytokines.

In some embodiments, the pharmaceutical or vaccine composition comprises a hybrid protein of the present application and/or an expression vector of the present application encapsulated in lipid nanoparticles (LNPs) for efficient delivery of the hybrid protein/expression vector into a target cell. In some embodiments, the pharmaceutical or vaccine composition comprises an mRNA encapsulated in lipid nanoparticles, wherein the mRNA encodes a hybrid protein of the present application.

In some embodiments, the vaccine is a seasonal influenza vaccine. The HA/NA chimeric molecule could be designed as described for any influenza virus. For example, a combination of current H3N2, H1N1 influenza A, and HN for influenza B virus vaccines, or a combination of measles, mumps and rubella virus vaccines could be developed using 3 different hybrid protein constructs delivered as mRNAs or as proteins.

III. Method of Use

Another aspect of the present application relates to a method for immunizing a subject against one or more viruses. The method comprises the step of administering to the subject an effective amount of the pharmaceutical or vaccine composition of the present application. In some embodiments, the one or more viruses comprise an influenza virus. In some embodiments, the one or more viruses comprise a combination of seasonal influenza viruses. In some embodiments, the one or more viruses comprise a combination of measles, mumps and rubella virus.

Another aspect of the present application relates to a method for vaccination against a subject against one or more viruses. The method comprises the step of administering to the subject an effective amount of the vaccine composition of the present application.

Another aspect of the present application relates to a method for introducing an immune response to one or more viruses in a subject. The method comprises the step of administering to the subject an effective amount of the vaccine composition of the present application.

The pharmaceutical or vaccine composition of the present application may be administered intramuscularly (i.m.), intradermally (i.d.), subcutaneously (s.c.), or by inhalation. The exact amount of the protein/mRNA pharmaceutical composition or vaccine required for effective immunization will vary from subject to subject, depending on the species, age, weight and general condition of the subject, the particular nucleic acid or vector used, its mode of administration and the like. An appropriate amount can be determined by one of ordinary skill in the art using only routine experimentation given the teachings herein. Thus, effective dosages and schedules for administering the compositions may be determined empirically, and making such determinations is within the skill in the art. The dosage ranges for the administration of the compositions are those large enough to produce the desired effect in which the symptoms of the disorders are affected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counter indications. Dosage can vary, and can be administered in one or more dose administrations daily, for one or several days. Guidance can be found in the literature for appropriate dosages for given classes of pharmaceutical products.

IV. Method of Making

The techniques used to generate and isolate the hybrid protein of the present application and/or the polynucleotide encoding the hybrid protein of the present application are known in the art. The cloning of the polynucleotides from genomic DNA can be effected, e.g., by using the well known polymerase chain reaction (PCR) or antibody screening of expression libraries to detect cloned DNA fragments with shared structural features. See, e.g., Innis et al., 1990, PCR: A Guide to Methods and Application, Academic Press, New York. Other nucleic acid amplification procedures such as ligase chain reaction (LCR), ligation activated transcription (LAT) and polynucleotide-based amplification (NASBA) may be used.

Modification of a polynucleotide encoding a hybrid protein of the present application may be necessary for synthesizing polypeptides substantially similar to the original polypeptide. Examples of modified nucleotides, such as 5-methyl pseudouridine and other modified nucleotides that can be substituted for the commonly used nucleotides, are well known in the art.

The term "substantially similar" to the polypeptide refers to non-naturally occurring forms of the polypeptide. These polypeptides may differ in some engineered way from the original polypeptide, e.g., variants that differ in specific activity, thermostability, pH optimum, or the like. The variants may be constructed on the basis of the polynucleotide presented as the polypeptide coding sequence disclosed herein, or the cDNA sequence thereof, e.g., a subsequence thereof, and/or by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence.

V. Vaccination Kit

Another aspect of the present application relates to a vaccination kit that comprises (1) a vaccine composition described herein packaged in administrable form (2) technical instructions with information on the administration and dosage An aspect of the present application is directed to a method for reducing mortality resulting from viral infection comprising administering to a subject in need thereof an effective amount of a composition comprising a hybrid protein comprising a first domain comprising a sequence encoding an ectodomain of a trimeric surface protein of an enveloped RNA virus and a second domain comprising a sequence encoding an ectodomain of a type 2 transmembrane domain protein, wherein the second domain is located at the C-terminal of the first domain; and a pharmaceutically acceptable carrier.

In some embodiments, the viral infection is a respiratory infection. In some embodiments, the viral infection is an influenza infection.

In some embodiments, the enveloped RNA virus is H1N1, H1N3, H3N2, H3N8, H5N1, H5N6, H7N9, or an influenza B virus.

In some embodiments, the surface protein is a mutated hemagglutinin (HA), wherein the second domain comprises an ectodomain of a neuraminidase (NA), wherein the mutated HA comprises a mutation that reduces aggregation and non-specific binding to sialic acid. In some further embodiments, a furin cleavage site of mutated HA is replaced with a linker sequence.

In some embodiments, the hybrid protein comprises SEQ ID NO:13.

In some embodiments, the hybrid protein comprises a sequence selected from the group consisting of SEQ ID NOS: 24-27.

An aspect of the present application is directed to a method for reducing viral load resulting from a viral infection in a subject in need thereof, comprising administering to the subject in need thereof an effective amount of a pharmaceutical composition comprising a hybrid protein comprising a first domain comprising a sequence encoding an ectodomain of a trimeric surface protein of an enveloped RNA virus and a second domain comprising a sequence encoding an ectodomain of a type 2 transmembrane domain protein, wherein the second domain is located at the C-terminal of the first domain; and a pharmaceutically acceptable carrier.

In some embodiments, the viral infection is a respiratory infection. In some embodiments, the viral infection is an influenza infection.

In some embodiments, the enveloped RNA virus is H1N1, H1N3, H3N2, H3N8, H5N1, H5N6, H7N9, or an influenza B virus.

In some embodiments, the surface protein is a mutated hemagglutinin (HA), wherein the second domain comprises an ectodomain of a neuraminidase (NA), wherein the mutated HA comprises a mutation that reduces aggregation and non-specific binding to sialic acid. In some further embodiments, a furin cleavage site of mutated HA is replaced with a linker sequence.

In some embodiments, the hybrid protein comprises SEQ ID NO:13.

In some embodiments, the hybrid protein comprises a sequence selected from the group consisting of SEQ ID NOS: 24-27.

An aspect of the present application is directed to a method for increasing immunity to viral infection in a subject in need thereof, comprising administering to the subject in need thereof an effective amount of a pharmaceutical composition comprising a hybrid protein comprising a first domain comprising a sequence encoding an ectodomain of a trimeric surface protein of an enveloped RNA virus and a second domain comprising a sequence encoding an ectodomain of a type 2 transmembrane domain protein, wherein the second domain is located at the C-terminal of the first domain; and a pharmaceutically acceptable carrier.

In some embodiments, the viral infection is a respiratory infection. In some embodiments, the viral infection is an influenza infection.

In some embodiments, the enveloped RNA virus is H1N1, H1N3, H3N2, H3N8, H5N1, H5N6, and H7N9, or an influenza B virus.

In some embodiments, the surface protein is a mutated hemagglutinin (HA), wherein the second domain comprises an ectodomain of a neuraminidase (NA), wherein the mutated HA comprises a mutation that reduces aggregation and non-specific binding to sialic acid. In some further embodiments, a furin cleavage site of mutated HA is replaced with a linker sequence.

In some embodiments, the hybrid protein comprises SEQ ID NO:13.

In some embodiments, the hybrid protein comprises a sequence selected from the group consisting of SEQ ID NOS: 24-27.

An aspect of the present application relates to a hybrid protein comprising a first domain comprising a sequence encoding an ectodomain of a trimeric surface protein of an enveloped RNA virus and a second domain comprising a sequence encoding an ectodomain of a type 2 transmembrane domain protein, wherein the second domain is located at the C-terminal of the first domain. In some embodiments, the hybrid protein further comprises a transmembrane domain of the trimeric surface protein and/or a transmembrane domain of the type 2 transmembrane domain protein. In some embodiments, the hybrid protein further comprises a cytoplasmic tail of the trimeric surface protein and/or a cytoplasmic tail of the type 2 transmembrane domain protein. In some embodiments, the hybrid protein further comprises an intracytoplasmic linker.

In some embodiments, the first domain comprises a sequence encoding a mutated hemagglutinin (HA) of the virus, wherein the mutated HA comprises a mutation that reduces aggregation and non-specific binding to sialic acid. In some embodiments, the second domain comprises an ectodomain of a neuraminidase (NA) of a virus. In some embodiments, the enveloped RNA virus is a virus of orthomyxoviridae. In some embodiments, the enveloped RNA virus is H1N1, H1N3, H3N2, H3N8, H5N1, H5N6, H7N9, influenza A virus or influenza B virus.

In some embodiments, the virus is H5N1 and wherein the mutation is a modification of the tyrosine at position 91 to phenylalanine in the mature H5N1 HA protein. In some embodiments, the hybrid protein comprises SEQ ID NO:13. In some embodiments, the furin cleavage site of mutated HA is replaced with a linker sequence. In some embodiments, the linker sequence has a length of 4-12 amino acids. In some embodiments, the hybrid protein comprises SEQ ID NO:24. In some embodiments, the hybrid protein comprises SEQ ID NO:25. In some embodiments, the hybrid protein comprises SEQ ID NO:26. In some embodiments, the hybrid protein comprises SEQ ID NO:27. In some embodiments, the hybrid protein comprises SEQ ID NO:28.

In some embodiments, the hybrid protein of the present application comprises a first domain comprising an amino acid sequence having at least 80%, at least 85%, at least 90%, at least 95%, at least 96%, at least 97%, at least 98%, or at least 99% sequence identity to SEQ ID NO:7 and/or a second domain comprising an amino acid sequence having at least 80%, at least 85%, at least 90%, at least 95%, at least 96%, at least 97%, at least 98%, or at least 99% sequence identity to SEQ ID NO:6.

An aspect of the present application relates to a hybrid protein comprising a first domain comprising a sequence encoding an immunogen of a virus; and a second domain comprising a sequence encoding an ectodomain of a type 2 transmembrane domain protein, wherein the second domain is located at the C-terminal of the first domain and wherein the second domain serves as an adjuvant to augment immune responses to the immunogen.

In some embodiments, the second domain comprises a sequence encoding an ectodomain of a neuraminidase (NA). In some embodiments, the ectodomain of the NA is derived from a protein with neuraminidase activity from any enveloped virus that has a neuraminidase that is a type 2 transmembrane protein.

In some embodiments, the immunogen is from a virus selected from the group consisting of orthomyxoviruses (such as influenza viruses, including H1N1, H1N3, H3N2, H3N8, H5N1, H5N6, H7N9, influenza A, and influenza B), paramyxoviruses, pneumoviruses, retroviruses (such as HIV), filoviruses (such as Ebola), coronaviruses, and arenaviruses (such as Lassa) and the type 2 transmembrane domain protein is an NA of an orthomyxovirus (such as an influenza virus). In some embodiments, the immunogen is selected from the group consisting of HAs of orthomyxoviruses, F proteins of paramyxoviruses, F proteins of pneumoviruses, Env proteins of retroviruses, glycoproteins of filoviruses, spike proteins of coronaviruses, and spike complexes of arenaviruses. In some embodiments, the immunogen is an immunogen from a measles virus, a mumps virus or a rubella virus.

An aspect of the present application relates to a hybrid protein comprising a first domain comprising a sequence encoding an immunogen from a first virus, and a second domain comprising a sequence from a type 2 transmembrane domain protein of a second virus. In some embodiments, the second domain is located at the C-terminal of the first domain. In some embodiments, the first virus and the second virus are the same virus. In some embodiments, the first virus and the second virus are different viruses. In some embodiments, the immunogen is an F protein of an RSV or human metapneumovirus and the type 2 transmembrane domain protein is a glycoprotein of an RSV or human metapneumovirus.

An aspect of the present application relates to a polynucleotide comprising a sequence encoding the hybrid protein of the present application. In some embodiments, the polynucleotide is a DNA molecule. In some embodiments, the polynucleotide is an RNA molecule. In some embodiments, the polynucleotide is a mRNA molecule.

An aspect of the present application relates to an expression vector that comprises the polynucleotide of the present application. In some embodiments, the expression vector is a non-viral vector, such as a plasmid. In some embodiments, the expression vector is a viral vector.

An aspect of the present application relates to a flu vaccine. In some embodiments, the vaccine comprises a hybrid protein the present application. In some embodiments, the vaccine comprises a polynucleotide of the present application. In some embodiments, the vaccine comprises an expression vector of the present application. In some embodiments, the vaccine comprises a mRNA of the present application encapsulated in lipid nanoparticles.

An aspect of the present application relates to a method for immunizing a subject against a flu virus. The method comprises the step of administering to the subject an effective amount of the vaccine composition of the present application.

An aspect of the present application relates to a method for introducing an immune response to a virus in a subject. The method comprises the step of administering to the subject an effective amount of the vaccine composition of the present application.

Further embodiments are illustrated in the following Examples which are given for illustrative purposes only and are not intended to limit the scope of the invention.

EXAMPLES

Example 1: Material and Methods

PBMC Isolation and Preparation

PBMCs are isolated from healthy donor whole blood using a Ficoll gradient centrifugation method. Whole blood is centrifuged at 400×g for 10 minutes. Plasma is transferred to a 50 ml tube and spun again at 1200×g for 10 minutes. The plasma is then aliquoted into labeled vials. Remaining blood is transferred to a sterile 50 ml tube, mixed with an equal volume of PBS or HBSS, and gently mixed or placed on a rocker. Ficoll tubes are prepared according to manufacturer guidelines. Diluted blood is carefully layered onto Ficoll, avoiding mixing, and centrifuged at 400×g for 30 minutes at room temperature with the brake off. After centrifugation, the top layer is removed, leaving 0.5 cm above the lymphocyte layer. The lymphocyte layer is transferred into labeled 50 ml tubes, with no more than 25 ml per tube. The lymphocyte suspension is brought to >45 ml with PBS or HBSS and centrifuged at 300×g for 10 minutes. Pellets are resuspended in 5 ml PBS and gently mixed. Suspensions from the same donor (up to 4 pellets) are combined in one tube. The volume is brought to >45 ml and centrifuged again at 300×g for 10 minutes. Finally, the pellet is resuspended in 10-20 ml PBS depending on the number of pellets combined. Cells are counted using standard procedures, and the total cell number is calculated. Following isolation, PBMCs are cryopreserved to allow for batch processing. PBMCs are cryopreserved in freezing media and stored in liquid nitrogen. Cryopreserved PBMCs are thawed rapidly and washed twice with warm complete RPMI 1640 media. Cell viability is determined using trypan blue exclusion.

Cell Culture and Restimulation

PBMCs are seeded in 24-well plates and stimulated under various conditions to assess the vaccine construct's ability to induce costimulatory molecule expression and activate an adaptive immune response. PBMCs are seeded at $5\times10^6$ cells/mL in complete RPMI in a 24-well plate. The following stimulation conditions are prepared: a negative control consisting of complete RPMI only, a positive control of complete RPMI with a T cell activator (e.g., anti-CD3/anti-CD28 beads or PMA/ionomycin), experimental conditions of complete RPMI with the vaccine construct (mRNA or protein) at predetermined concentrations, and an additional control (if applicable) of complete RPMI with HA protein or NA protein alone. Cells are incubated at 37° C. in a 5% $CO_2$ incubator for specified time points. For intracellular cytokine staining, brefeldin A or GolgiPlug is added during the last 4-6 hours of incubation.

Flow Cytometry Staining and Analysis

Cells are harvested and stained with a panel of antibodies to identify cell populations and assess the expression of relevant markers. Cells are harvested and washed with FACS buffer. For surface staining, cells are stained with appropriate surface antibodies. Cells are incubated with antibodies for 20-30 minutes at 4° C. and then washed with FACS buffer. For intracellular staining, cells are fixed and permeabilized. Cells are stained with appropriate intracellular antibodies. Cells are incubated with antibodies for 20-30 minutes at 4° C. and washed with FACS buffer. Cells are resuspended in FACS buffer, and data is acquired using a flow cytometer. Flow cytometry data is analyzed to quantify marker expression. Flow cytometry data is analyzed using appropriate software. Gating strategies are used to identify cell populations. The expression levels of costimulatory molecules, activation markers, cytotoxic markers, and cytokines will be determined. Expression levels are compared between control and experimental conditions. The percentage of positive cells and MFI are calculated.

Statistical Analysis

Statistical methods are used to determine the significance of the findings. Statistical analysis is performed using appropriate software. Statistical tests such as ANOVA or t-tests are used. Statistical significance is determined ($p<0.05$). Data is presented as mean±standard deviation or standard error of the mean.

Animal Experiments

All animal experiments are reviewed and approved by the Institutional Animal Care and Use Committee of Morehouse School of Medicine (MSM). All animals are housed and cared for in accordance with local, state, federal, and institutional policies of the American Association for Accreditation of Laboratory Animal Care. Animal studies are fully conducted at Bioqual. Bioqual has AAALAC, PHS, and USDA assurances and has been used for other studies funded by the NIH.

Example 2: Expression Vectors Encoding a H5N1 Hybrid Vaccine Peptide

An expression vector comprising a coding sequence for a NA-HA hybrid protein is generated with standard molecular cloning techniques. The hybrid protein (SEQ ID NO:1) comprises a signal peptide (SEQ ID NO:2), a HA1 domain of H5N1 strain A/Texas/37/2024 with a Y107F mutation (SEQ ID NO:3), a HA2 domain of H5N1 strain A/Texas/37/202 (SEQ ID NO:4), a foldon/linker region (SEQ ID NO:5) and the ectodomain of the wild-type NA of H5N1 strain A/Texas/37/2024 (SEQ ID NO:6).

Example 3: Hybrid HA-NA mRNA Vaccine for Avian Influenza

This study aims to develop a novel mRNA vaccine platform using a hybrid hemagglutinin-neuraminidase (HA-NA) spike protein. The mRNA construct encodes a hybrid protein incorporating a T4 foldon trimerization domain and a proprietary ESCORT tag to enhance antigen stability and immunogenicity. The vaccine is validated through immunological assays using human PBMCs and protective efficacy testing in murine challenge models, with the goal of advancing toward Phase 1 clinical trials.

Figure 2A:
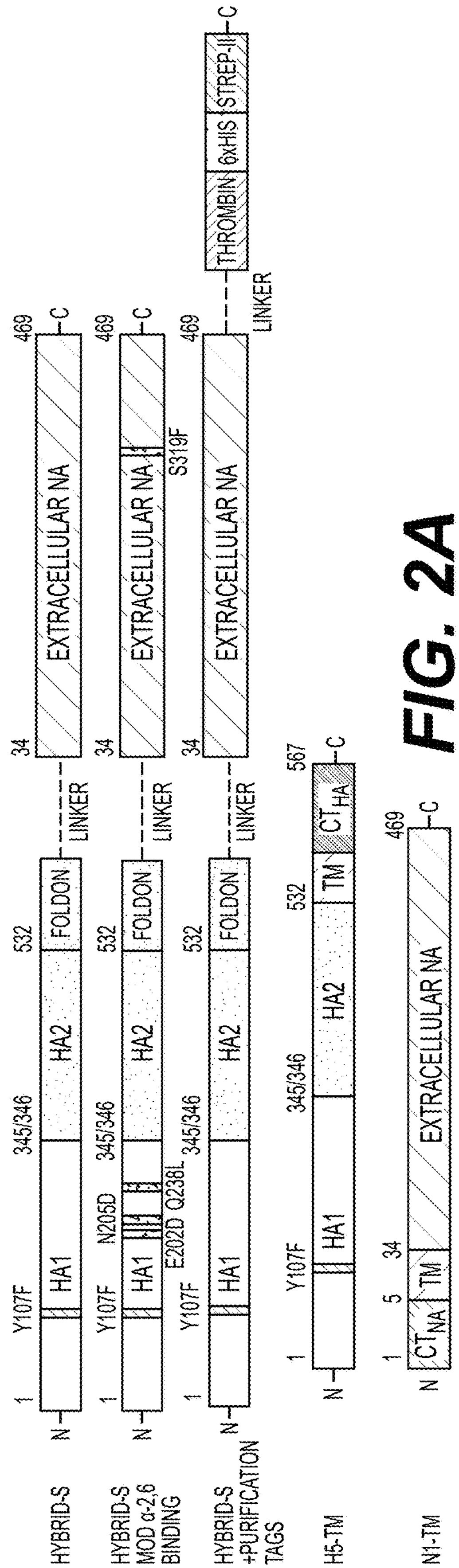
FIG. 2A shows schematic representations of some embodiments of the H5N1 influenza vaccine constructs.
Figure 2B:
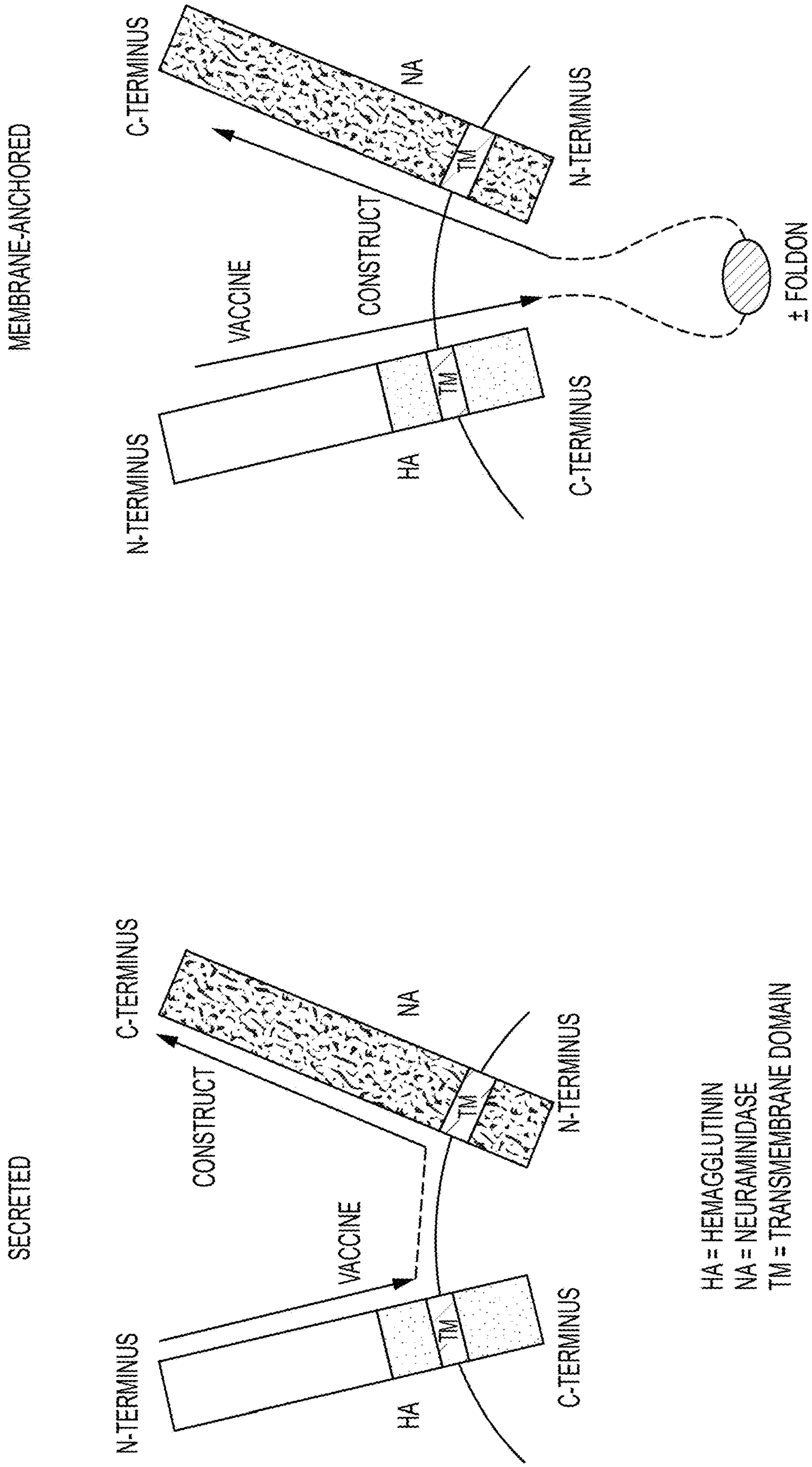
FIG. 2B shows an exemplary membrane-anchored construct design including a foldon at the C-terminus of NA.

The HA-NA constructs are designed with specific mutations to take into account HA modifications that could enhance binding to alpha-2,6 human-type sialic acid receptors. Validation assays include pseudovirus neutralization, hemagglutination inhibition (HI), and structural characterization through electron microscopy and potentially X-ray crystallography. FIG. 2A shows schematic representations of some embodiments of the H5N1 influenza vaccine constructs. FIG. 2B shows construct designs including a foldon and/or an EDN tag (±foldon±EDN) at the C-terminus of NA.

Target genes are amplified from viral RNA using reverse transcription-PCR (RT-PCR) with primers specific to H5N1 sequences. PCR products are purified and cloned into plasmid vectors at VaxCo. Clones are verified by restriction enzyme digestion, colony PCR, and sequencing. Mutagenesis is performed using deep mutational scanning to identify amino acid changes that influence receptor binding, including α2-6 sialic acid specificity. Purification of His-tagged proteins (e.g., HA1) is achieved using Ni-NTA affinity chromatography. Protein quality and integrity are assessed by SDS-PAGE, Western blotting (anti-His or polyclonal antibodies), and hemagglutination assays. Validation assays include Western blotting to confirm antigenicity and ELISA to quantify antibody binding. Functional activity of vaccine-induced antibodies is evaluated using pseudo typed virus neutralization and hemagglutination inhibition (HI) assays. Structural validation of key mutations (e.g., Q226L) is performed via X-ray crystallography or receptor-binding studies.

Figure 3:
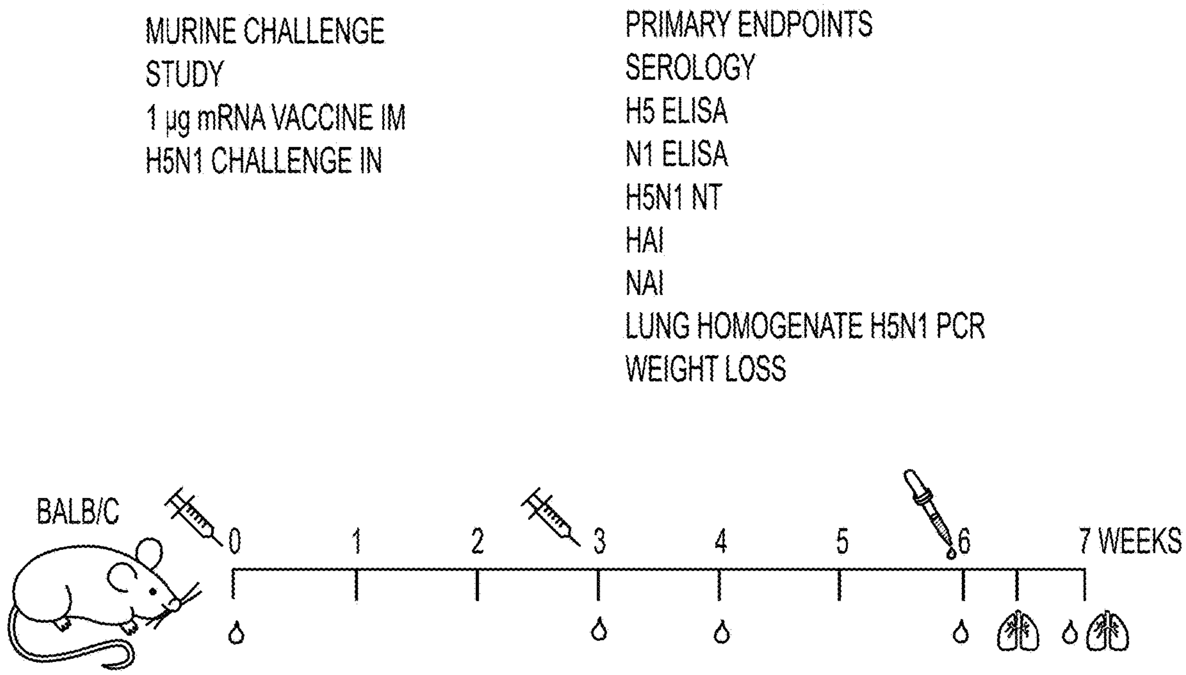
FIG. 3 is a schematic showing the timeline of an animal challenge design.

Upon validation of the hybrid protein constructs, corresponding mRNA constructs are prepared and tested in animal models. FIG. 3 shows an example of the timeline of animal immunization and challenge study in mice. Briefly, female BALB/c mice are used for the study. Treatment for all mice occurs on study day 0 (SDO) and 21 (SD21) via intramuscular (IM) administration. Following treatment, the animals are challenged intranasally with H5N1A/Texas/37/2024 as indicated (FIG. 3). All animals have terminal blood collections at the specified timepoints. The animals are terminated at 2 timepoints as indicated. Lungs are collected at timepoints as exemplified in FIG. 3 and have viral load measured by PCR analysis. ELISA and hemagglutination inhibition (HAI) assay are performed. During the challenge period, weights are recorded daily, and clinical observations are recorded BID. Weights are used as a measure of illness and used to calibrate in-life blood collection, weight-based sedation, and weight-based treatments. Additionally, Injection site monitoring occurs for 1 day after each IM treatment.

Example 4: Characterization of Exemplary Antigenic Constructs

Figure 4:
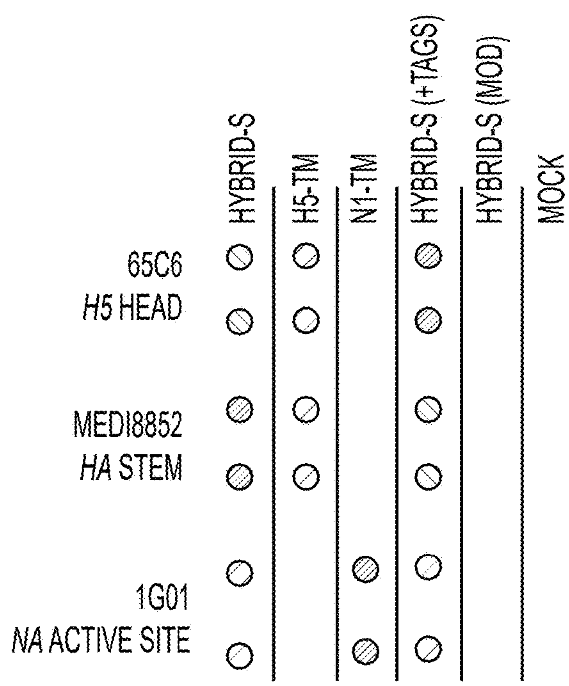
FIG. 4 shows the result of a preliminary antigen expression test with some of the exemplary mRNA constructs in a dot blot assay.
Figure 5A:
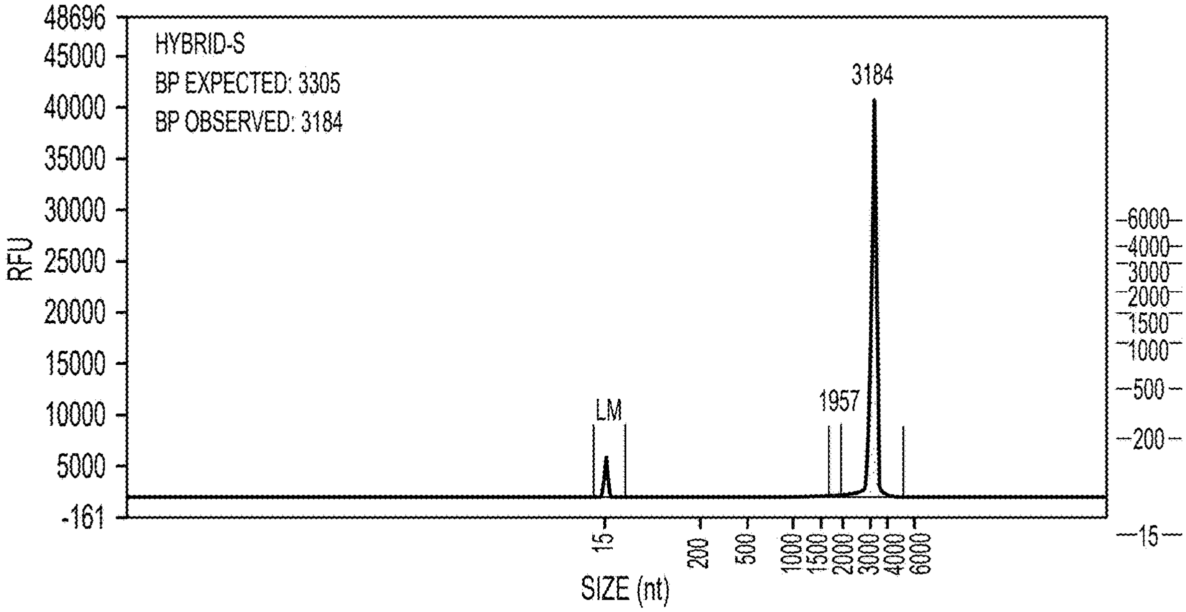
FIGS. 5A-5C show the mRNA size and quality as determined by fragment analyzer for construct Hybrid-S (FIG. 5A), H5-TM (FIG. 5B), and N1-TM (FIG. 5C).
Figure 5B:
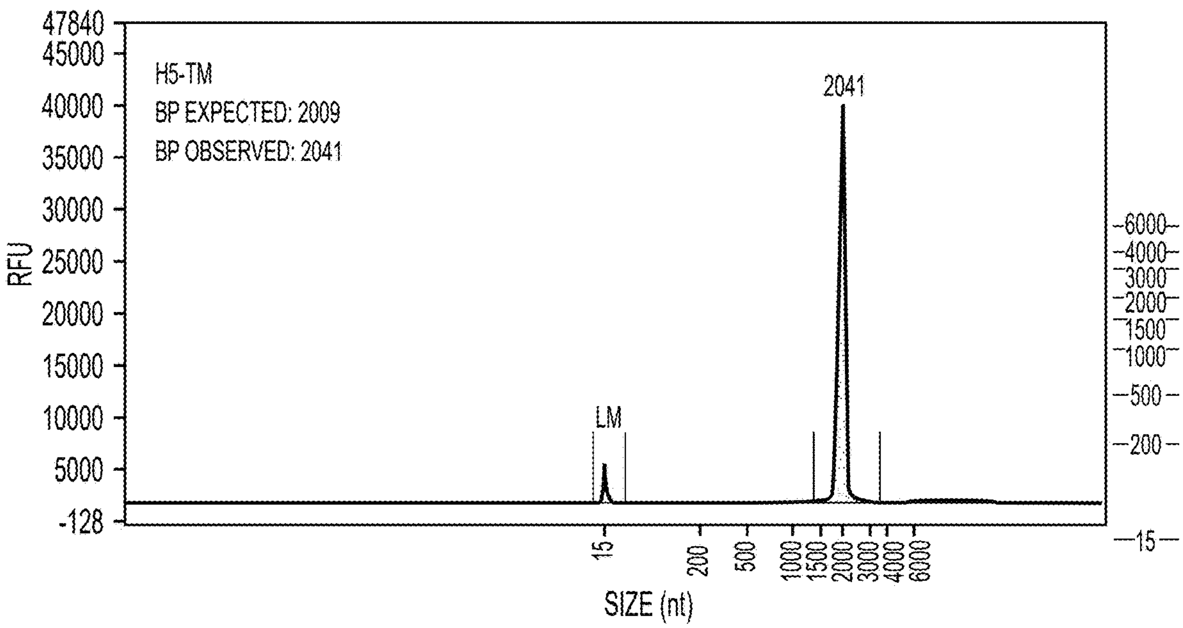
Figure 5C:
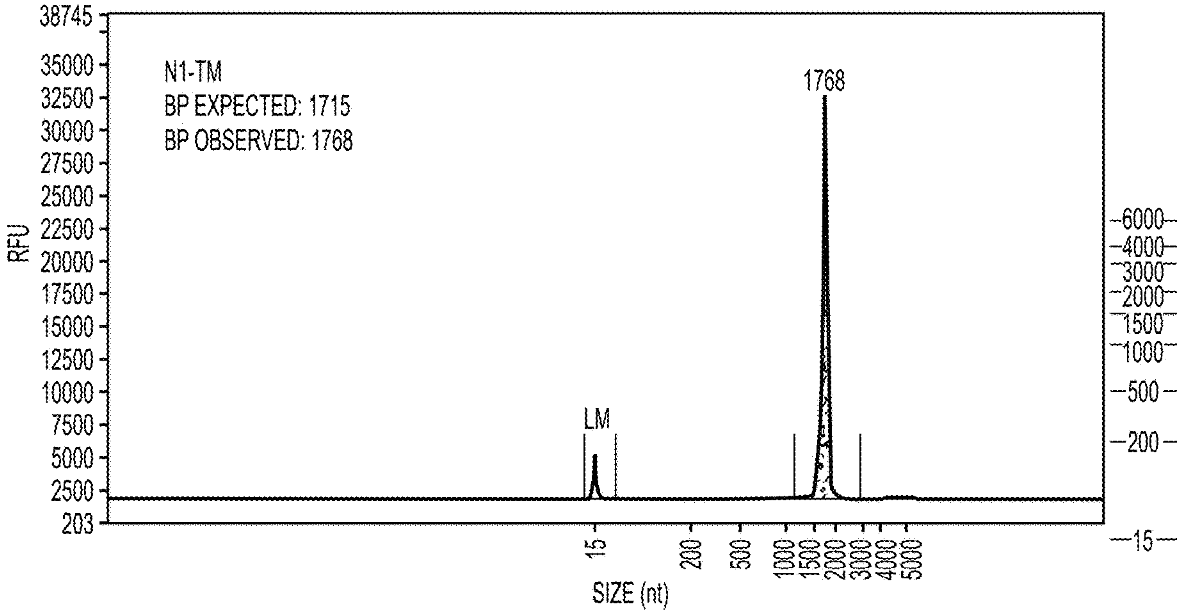
Figure 6A:
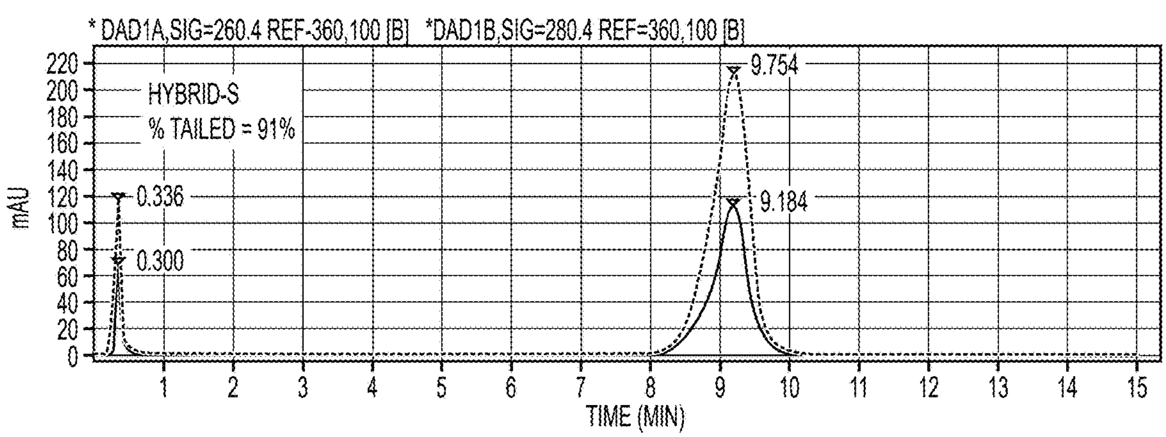
Figure 7:
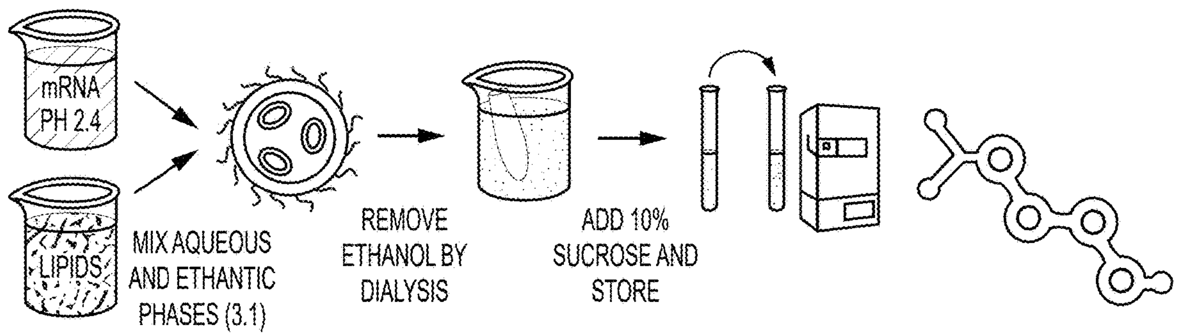
FIG. 7 shows encapsulation of mRNAs encoding the hybrid proteins of the present application.
Figure 8A:
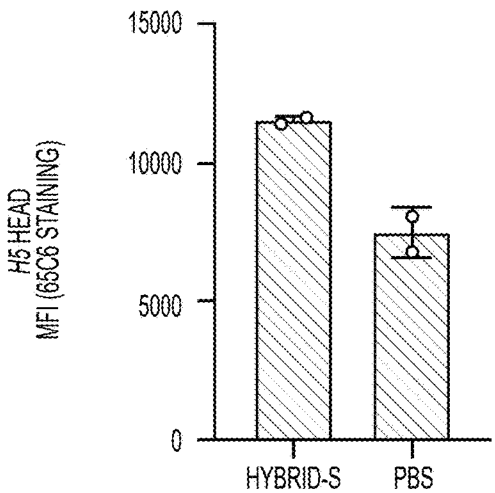
FIG. 8A shows 65C6 staining of Hybrid-S-transfected HeLa cells compared to PBS controls.
Figure 8B:
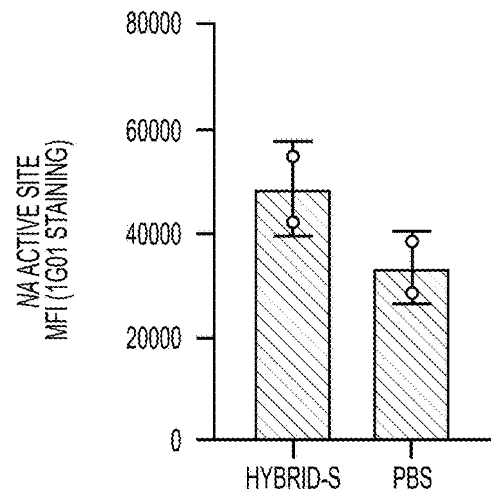
FIG. 8B shows 1G01 staining of Hybrid-S-transfected HeLa cells compared to PBS controls.
Figure 9:
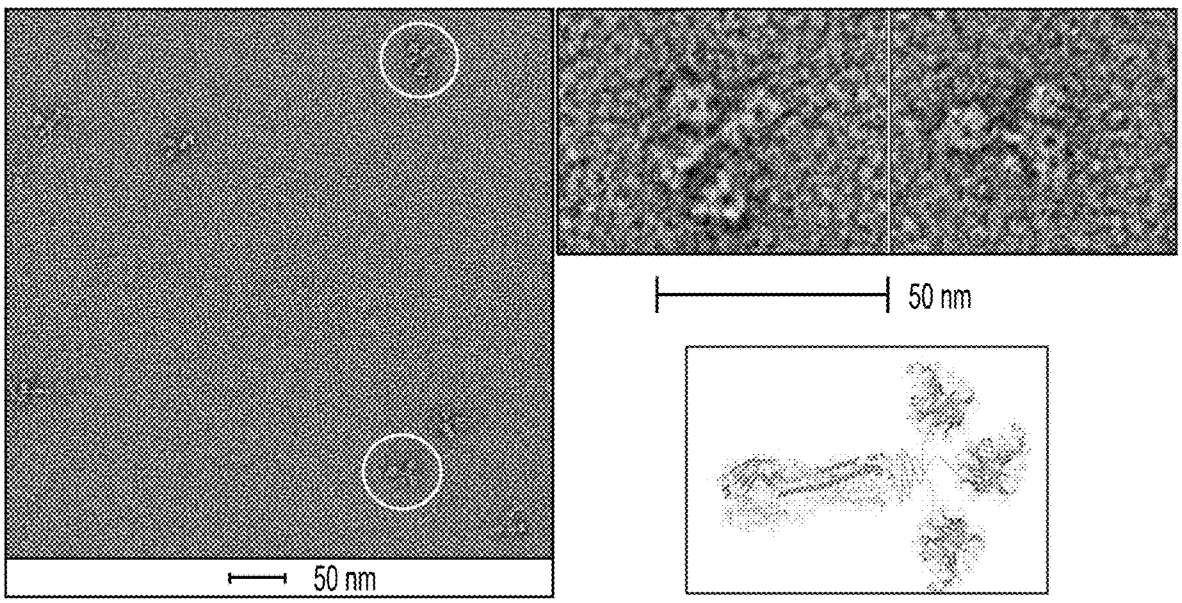
FIG. 9 shows transmission electron microscopic images of the secreted molecule and the predicted model.

FIG. 2A is a schematic showing the mRNA design for some exemplary constructs encoding some of the antigenic hybrid protein constructs for Hybrid-S(SEQ ID NO:16), Hybrid-S modified for better α-2,6 binding (SEQ ID NO:23), Hybrid-S having a linker and thrombin cleavage site along with histidine and streptavidin tags (SEQ ID NO:22), full-length hemagglutinin (SEQ ID NO:17) including a trans-membrane domain, and full-length neuraminidase (SEQ ID NO:18) including a trans-membrane domain. The amino acid sequences of the other two constructs, with GS linker and GS linkers/foldon are shown in SEQ ID NO:19 (HA+GS linker+NA) and SEQ ID NO:20 (HA+GS linker+Foldon+GS linker+NA), respectively. DNA plasmids encoding the mRNA constructs were generated. FIG. 4 shows the result of a preliminary antigen expression test with some of the exemplary mRNA constructs in a dot blot assay. FIGS. 5A-5C show the mRNA size of Hybrid-S (FIG. 5A), H5-TM (FIG. 5B), and N1-TM (FIG. 5C) and quality as determined by fragment analyzer. DNA plasmid encoding the constructs of interest were linearized by BspQI digest. mRNA was produced by T7 in vitro transcription and purified by lithium chloride precipitation. mRNA size and quality was determined by fragment analyzer. FIG. 6A-6C show the percentage of mRNA tailing by analytical HPLC and tail length by LC/MS of Hybrid-S (FIG. 6A), h5-TM (FIG. 6B), and N1-TM (FIG. 6C), with FIG. 6D depicting distribution and main peak length tor the constructs of FIGS. 6A-6C and for Flu 1014. mRNA % tailing was determined on the basis of binding to an oligo dT column by analytical HPLC. The % tailed was defined as the % of the bound peak area relative to the peak are eluting in the void volume. The constructs were digested with cusativin, an RNase T2, to liberate the intact tails and the digest products were separated by ion-pairing HPLC directly coupled to mass spectrometry. The mass spectra corresponding to the polyA tail were averaged and the tail lengths were determined by deconvolution of the isotopically-resolved spectra. The expressed mRNA was then encapsulated in lipid nanoparticles (LNPs) as shown in FIG. 7. Expression of the mRNA encoded proteins were successfully detected in cells transduced with the LNP-encapsulated mRNAs (FIG. 8). Expi293 cells were transfected with the Hybrid-S plasmid encoding a hybrid spike-H5 hemagglutinin hybrid protein. PBS-treated cells served as a negative control. At the indicated timepoint post-transfection, cells were fixed and permeabilized to permit intracellular staining. Cells were then stained with either 65C6 (anti-H5 hemagglutinin monoclonal antibody) or 1G01 (anti-neuraminidase monoclonal antibody), followed by flow cytometry. In FIG. 8A, staining with 65C6 showed significantly elevated intracellular HA expression in Hybrid-S-transfected cells compared to PBS controls, as indicated by higher mean fluorescence intensity (MFI). In contrast, FIG. 8B shows that 1G01 staining did not differ significantly between Hybrid-S and PBS groups, suggesting that the Hybrid-S construct does not drive robust intracellular neuraminidase expression detectable by 1G01. Bars represent mean±SD of MFI. Statistical comparisons were performed using unpaired two-tailed t-tests. Significance is indicated as: $p<0.01$ (); ns, not significant. FIG. 9** shows low-resolution transmission electron microscopic images of the secreted molecule confirming that the structure corresponds to the illustrated predicted model.

Figure 10A:
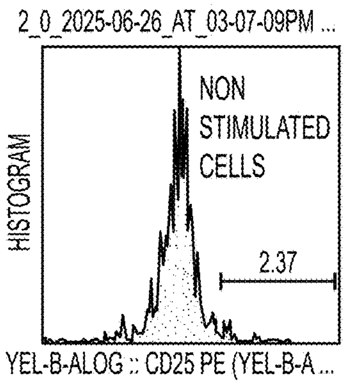
FIGS. 10A-10I show CD25 expression in $CD4^+$ T cells following stimulation with influenza vaccine construct or viral particle supernatants. PBS-treated control cells (FIG. 10A) are shown, along with cells treated with supernatants from, Hybrid-S (FIG. 10B), H5 (FIG. 10C), N1 (FIG. 10D), and strep-tagged Hybrid-S (FIG. 10E). Cells were also treated with supernatants from H5N1 field isolates (Colorado (FIG. 10G) and Michigan (FIG. 10H)), as well as seasonal influenza virus (FIG. 10I).
Figure 10B:
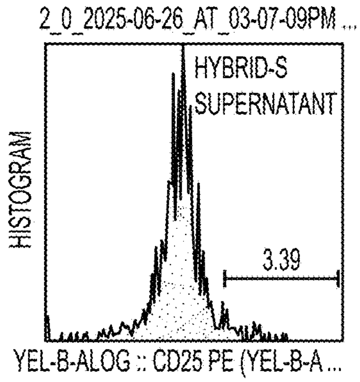
Figure 10C:
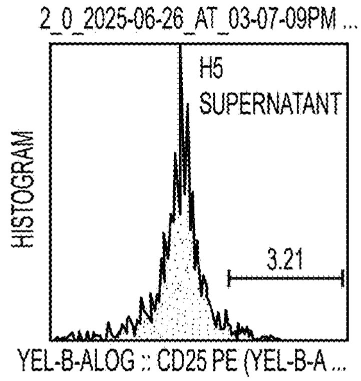
Figure 10D:
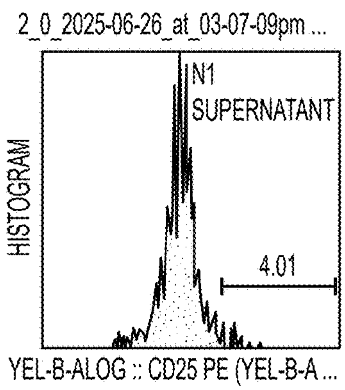
Figure 10E:
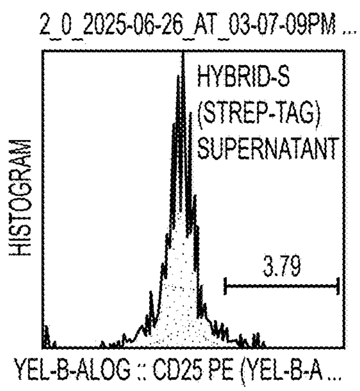
Figure 10F:
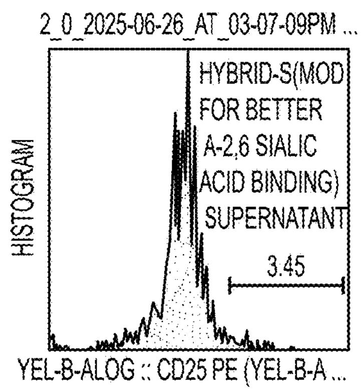
Figure 10G:
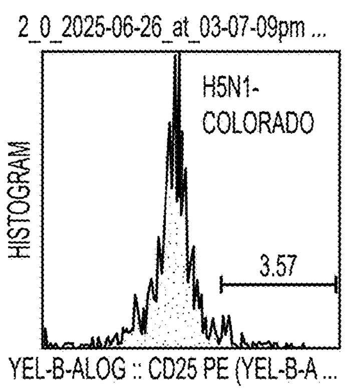
Figure 10H:
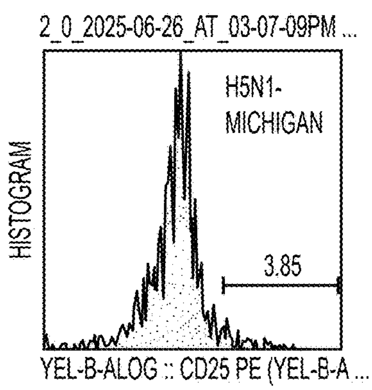
Figure 10I:
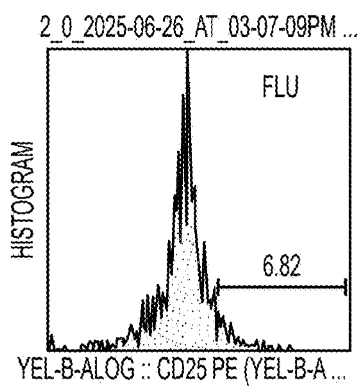

Example 5: CD25 Expression in $CD4^+$ T Cells Following Stimulation with Supernatants Naïve human donor $CD4^+$ T cells were stimulated with supernatants collected from Expi293 cells transfected with various influenza vaccine constructs, including H5 (FIG. 10C), N1 (FIG. 10D), Hybrid-S (a hybrid spike-H5 hemagglutinin fusion; FIG. 10B), strep-tagged Hybrid-S (FIG. 10E), and a version of Hybrid-S modified to enhance α2,6 sialic acid binding (FIG. 10F). Supernatants from H5N1 field isolates (Colorado (FIG. 10G) and Michigan (FIG. 10H)), as well as seasonal influenza virus (such as H1N1 and H3N2 strains; FIG. 10I). PBS-treated (non-stimulated) cells (FIG. 10A) were used as controls. Following stimulation, CD25 surface expression was measured by flow cytometry using PE-conjugated anti-CD25 antibody. Histograms represent fluorescence intensity distributions, with values indicating geometric mean fluorescence intensity (gMFI).

Results show that N1 supernatant induced the highest level of CD25 expression in $CD4^+$ T cells (gMFI 4.01), with strep-tagged Hybrid-S, H5N1 Michigan, and Hybrid-S also inducing modest activation compared to the non-stimulated control (2.37). Seasonal influenza supernatant provided a strong positive response (gMFI 6.82), inducing the highest CD25 expression across all conditions. This indicates surprisingly strong $CD4^+$ T cell reactivity to seasonal flu strains different from the strain that the antigenic construct was constructed, providing a strong protective effect for both humoral and cellular immune responses to influenza strains.

Figure 11A:
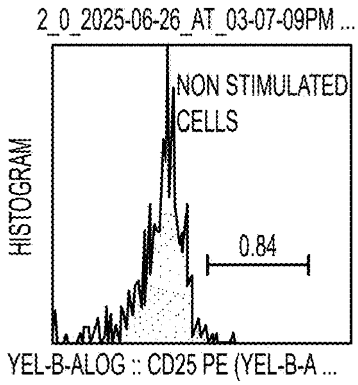
FIGS. 11A-11I show CD25 expression in $CD8^+$ T cells following stimulation with influenza vaccine construct or viral particle supernatants. PBS-treated control cells (FIG. 11A) are shown, along with cells treated with supernatants from, Hybrid-S (FIG. 11B), H5 (FIG. 11C), N1 (FIG. 11D), and strep-tagged Hybrid-S (FIG. 11E). Cells were also treated with supernatants from H5N1 field isolates (Colorado (FIG. 11G) and Michigan (FIG. 11H)), as well as seasonal influenza virus (FIG. 11I).
Figure 11B:
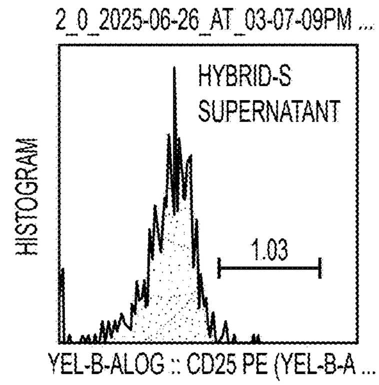
Figure 11C:
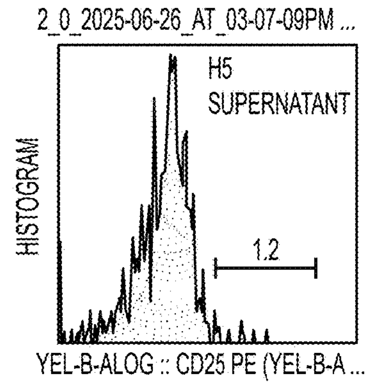
Figure 11D:
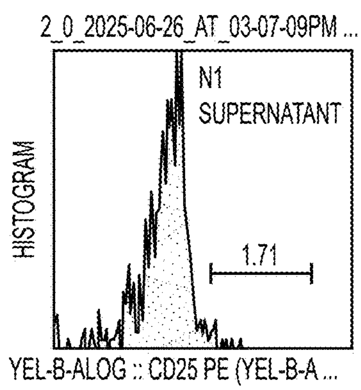
Figure 11E:
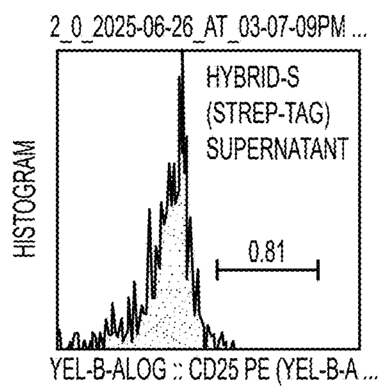
Figure 11F:
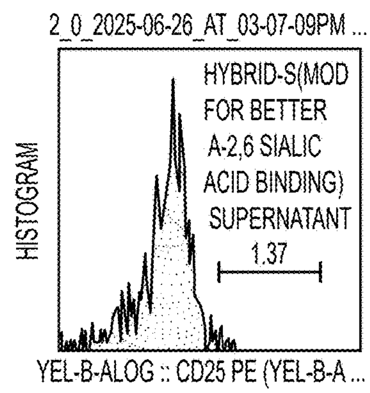
Figure 11G:
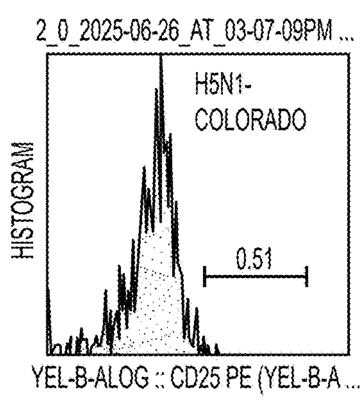
Figure 11H:
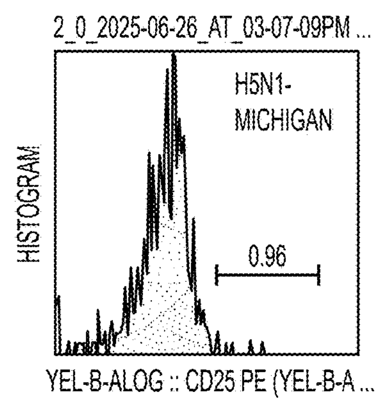

Example 6: CD25 Expression in $CD8^+$ T Cells Following Stimulation with Supernatants Naïve human donor $CD8^+$ T cells were stimulated with the same panel of vaccine construct supernatants and viral controls as described in FIGS. 10A-10I. Cells were stained with PE-conjugated anti-CD25 antibody and analyzed by flow cytometry. Histograms display CD25 fluorescence intensity profiles, and values reflect geometric mean fluorescence intensity (gMFI). Among $CD8^+$ T cells, the N1 supernatant (FIG. 11D) again triggered the highest activation (gMFI 1.71), followed by the α2,6-binding-optimized Hybrid-S (gMFI 1.37; FIG. 11F). The standard Hybrid-S construct (gMFI 1.03; FIG. 11B) showed modest CD25 induction relative to the non-stimulated group (0.84; FIG. 11A), indicating weak $CD8^+$ T cell activation. H5N1 Michigan supernatant induced a moderate response (FIG. 11H), while H5N1 Colorado (FIG. 11G) and the strep-tagged Hybrid-S (FIG. 11E) construct failed to elevate CD25 expression, suggesting poor immunostimulatory activity in the $CD8^+$ compartment. Because the hybrid-S was mostly a secreted soluble protein, it would not be expected to induce much of a CD8 response. Without being bound by theory, the modified hybrid protein did not express well so more of it may have gone through the proteasome and was processed in a way that could trigger CD8.

Figure 11I:
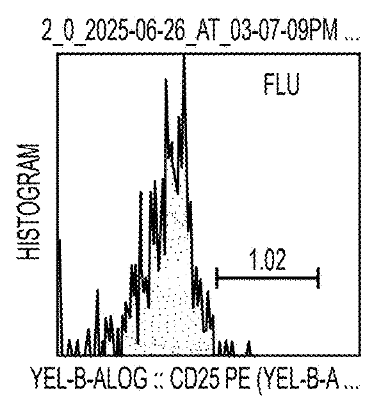

Seasonal flu supernatant showed a good response (1.02; FIG. 11I) that, when viewed in conjunction with the CD4+ T cell response (FIG. 10I) is promising for the cellular response to seasonal flu strains, such as the H1N1 and H3N2 strains.

Figure 12A:
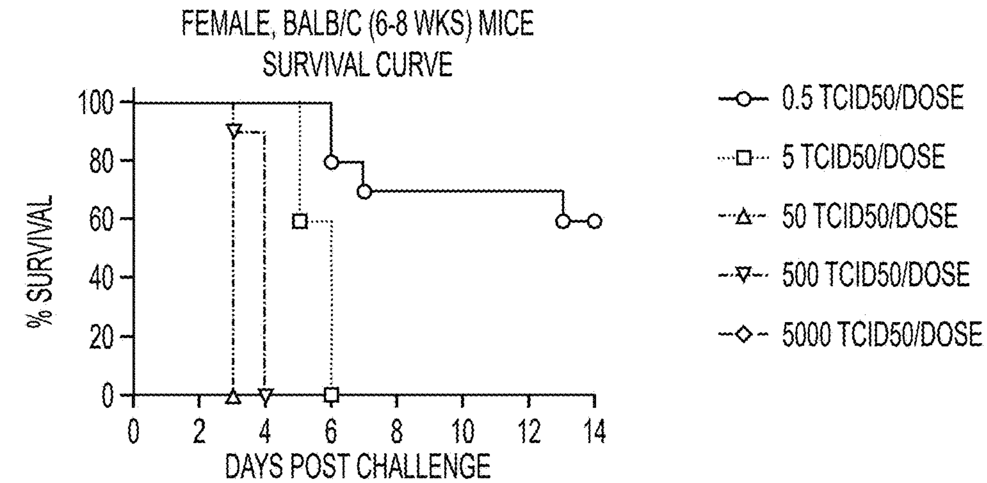
FIGS. 12A-12C show determination of the $LD_{50}$ dose of viral particles and protective efficacy of candidate vaccine constructs against H5N1 challenge in female BALB/c mice.

Example 7: Protective Efficacy of Candidate Vaccine Constructs Against H5N1 Challenge in Female BALB/c Mice To determine the $LD_{50}$ dose of viral particles, female BALB/c mice (6-8 weeks old) were challenged with 0.5 to 5000 $TCID_{50}$ of H5N1 virus (A/TEXAS/8/37/2024) via the indicated doses (FIG. 12A). For the first dose, mice were given 1 μg of vaccine construct injected in the right quadriceps muscle. The second immunization was performed 21 days later, with 1 μg of vaccine construct injected in the left quadriceps muscle. The mice were infected with H5N1 intranasally 21 days later. The challenge dose of 5 $TCID_{50}$ corresponds to approximately 10× the $LD_{50}$ for this strain ($LD_{50}$≈0.7 $TCID_{50}$), based on internal titration studies performed in MDCK cells ($TCID_{50}$ titer: $1.3\times10^9$ $TCID_{50}$/ml).

Survival was monitored daily for 14 days post-challenge. Mice receiving 0.5 $TCID_{50}$/dose exhibited the highest survival, while all mice challenged with ≥50 $TCID_{50}$ succumbed to infection within 6 days post-challenge. Data demonstrate a dose-dependent lethality curve for this H5N1 strain in unprotected mice.

Figure 12B:
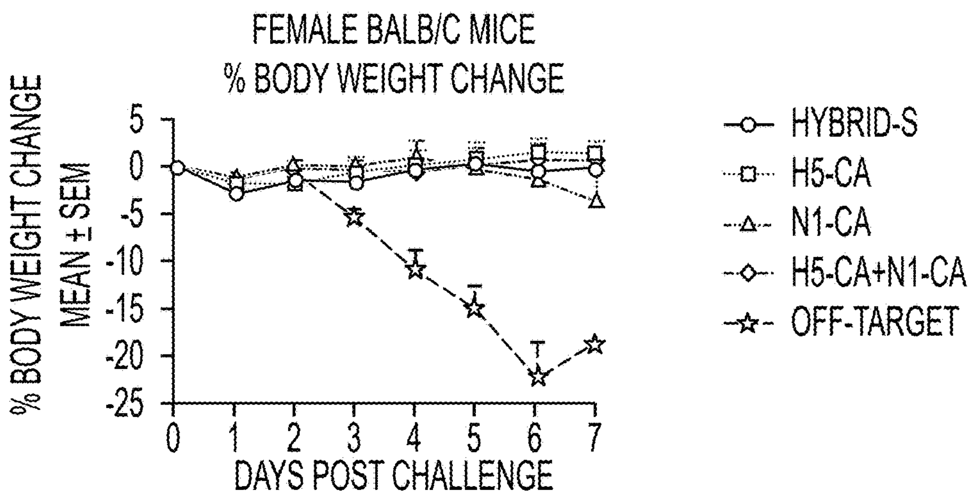

FIG. 12B shows the percent body weight change following intranasal challenge with H5N1 (A/Texas/37/2024) at $7.34\times10^3$ $TCID_{50}$/dose. Groups included Hybrid-S, H5-CA, N1-CA, H5-CA+N1-CA, and an off-target control. Vaccinated groups (Hybrid-S, H5-CA, N1-CA, H5-CA+N1-CA) maintained stable body weight post-challenge, while the off-target control group exhibited progressive weight loss exceeding 20% by day 6-7. Data are shown as mean±SEM.

Figure 12C:
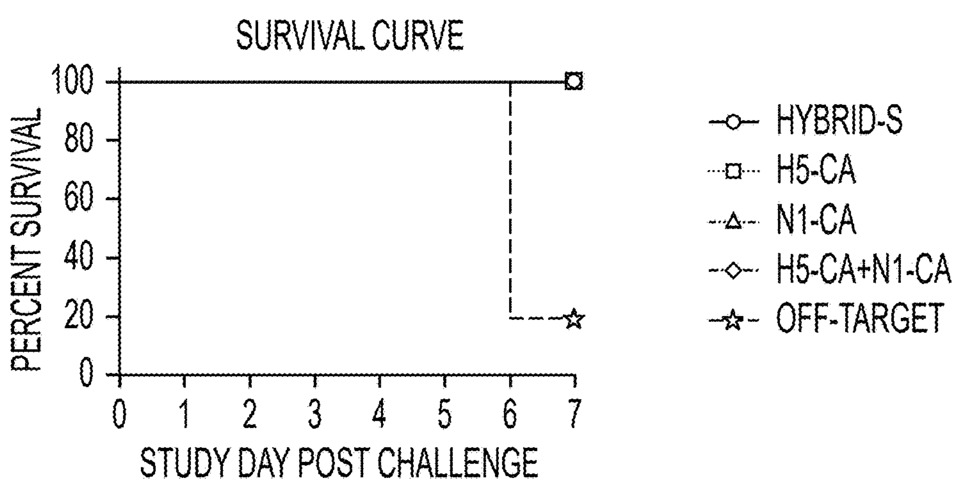

FIG. 12C shows the Kaplan-Meier survival analysis over 7 days post-challenge. All vaccinated groups (Hybrid-S, H5-CA, N1-CA, H5-CA+N1-CA) demonstrated 100% survival, whereas only 20% of the off-target group survived to day 7. Challenge material for this study was H5N1 (A/Texas/37/2024), Titer: $1\times10^9.^{13}$ $TCID_{50}$/mL, Lot #25JULY2024-MPORTO.

These results illustrate that the immunogenic vaccine constructs of the present application demonstrate the ability to reduce mortality resulting from influenza infection.

Figure 13A:
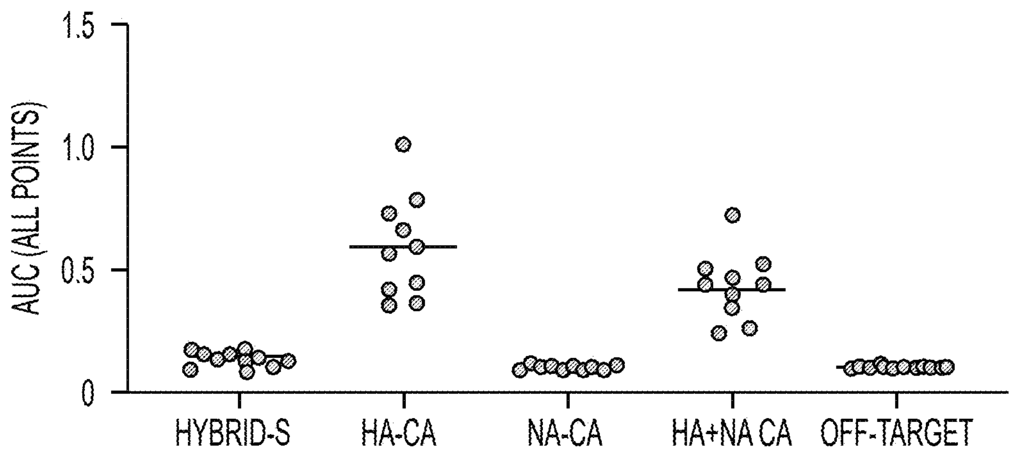
FIGS. 13A-13B show HA-specific antibody responses of female BALB/c mice on day 20 after priming only (FIG. 13A), or on day 28 after priming and boost (FIG. 13B).
Figure 13B:
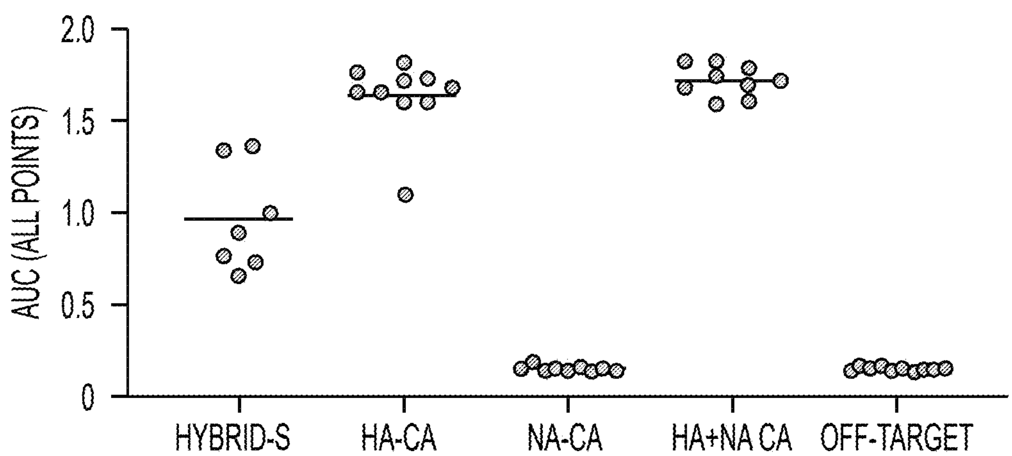

Example 8: Induction of HA-Specific Antibody Responses Following Vaccination with Candidate Constructs Sera from vaccinated female BALB/c mice were analyzed by HA-binding ELISA. Antibody responses were quantified as area under the curve (AUC) across all dilutions. For the first dose, mice were given 1 μg of vaccine construct injected in the right quadriceps muscle. The second immunization was performed 21 days later, with 1 μg of vaccine construct injected in the left quadriceps muscle. The mice were infected with H5N1 intranasally 21 days later. (FIG. 13A) Prime-only (Day 20): HA-CA and HA+NA-CA groups demonstrated measurable HA-binding activity, while Hybrid-S, NA-CA, and off-target controls exhibited minimal responses. (FIG. 13B) Prime+Boost (Day 28): HA-CA and HA+NA-CA groups showed strong and consistent HA-binding antibody responses, with Hybrid-S displaying intermediate activity. NA-CA and off-target controls remained negative.

These results demonstrate that constructs encoding HA, either alone or in combination with NA, elicit robust antigen-specific humoral responses following prime-boost immunization. These results show the surprising adjuvant effect that the NA subunit has, strongly enhancing the antibody response to HA. NA increases the affinity of antibodies to influenza antigens, protecting subjects against lethal challenge.

Figure 14A:
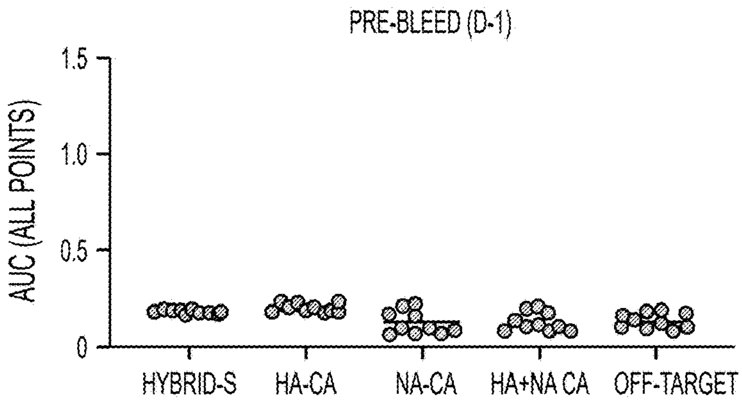
FIGS. 14A-14C show the Induction of NA-specific antibody responses following vaccination with candidate constructs.
Figure 14B:
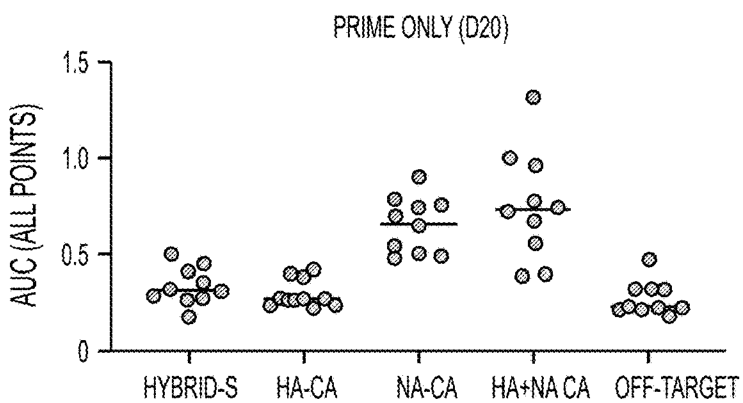
Figure 14C:
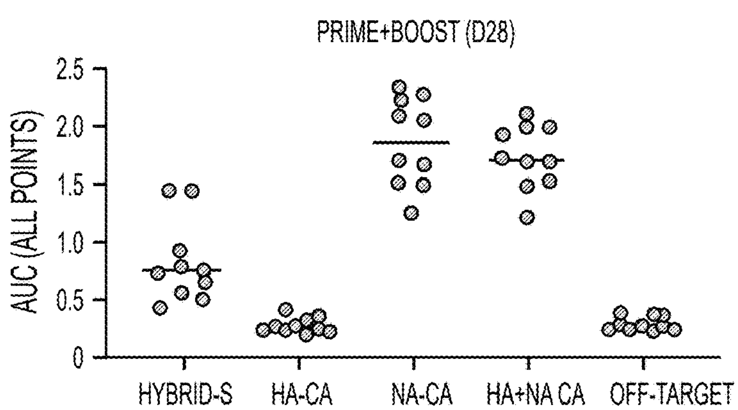

Example 9: Induction of NA-Specific Antibody Responses Following Vaccination with Candidate Constructs Sera from vaccinated female BALB/c mice were analyzed by NA-binding ELISA, and responses were quantified as area under the curve (AUC) across all serum dilutions. FIG. 14A shows that at pre-bleed on Day ⁻1 there was no detectable NA-specific antibody responses were observed across all groups, confirming baseline seronegativity prior to vaccination. FIG. 14B shows that on Day 20 in mice that were primed-only the NA-CA and HA+NA-CA groups demonstrated induction of NA-binding activity, with Hybrid-S and HA-CA groups showing minimal responses, and off-target controls remaining negative. FIG. 14C shows that on Day 28, in mice that were both primed and boosted, the NA-CA and HA+NA-CA groups showed strong and consistent NA-binding antibody responses, exceeding those seen in the prime-only condition. Hybrid-S exhibited intermediate activity, while HA-CA and off-target controls remained negative.

These results demonstrate that constructs encoding NA, either alone or in combination with HA, elicit robust antigen-specific humoral responses following prime-boost immunization. These results show the surprising adjuvant effect that the NA subunit has, strongly enhancing the antibody response to HA. NA increases the affinity of antibodies to influenza antigens, protecting subjects against lethal challenge.

Example 10: Viral Load in Lung Tissue Following H5N1 Challenge

Figure 15:
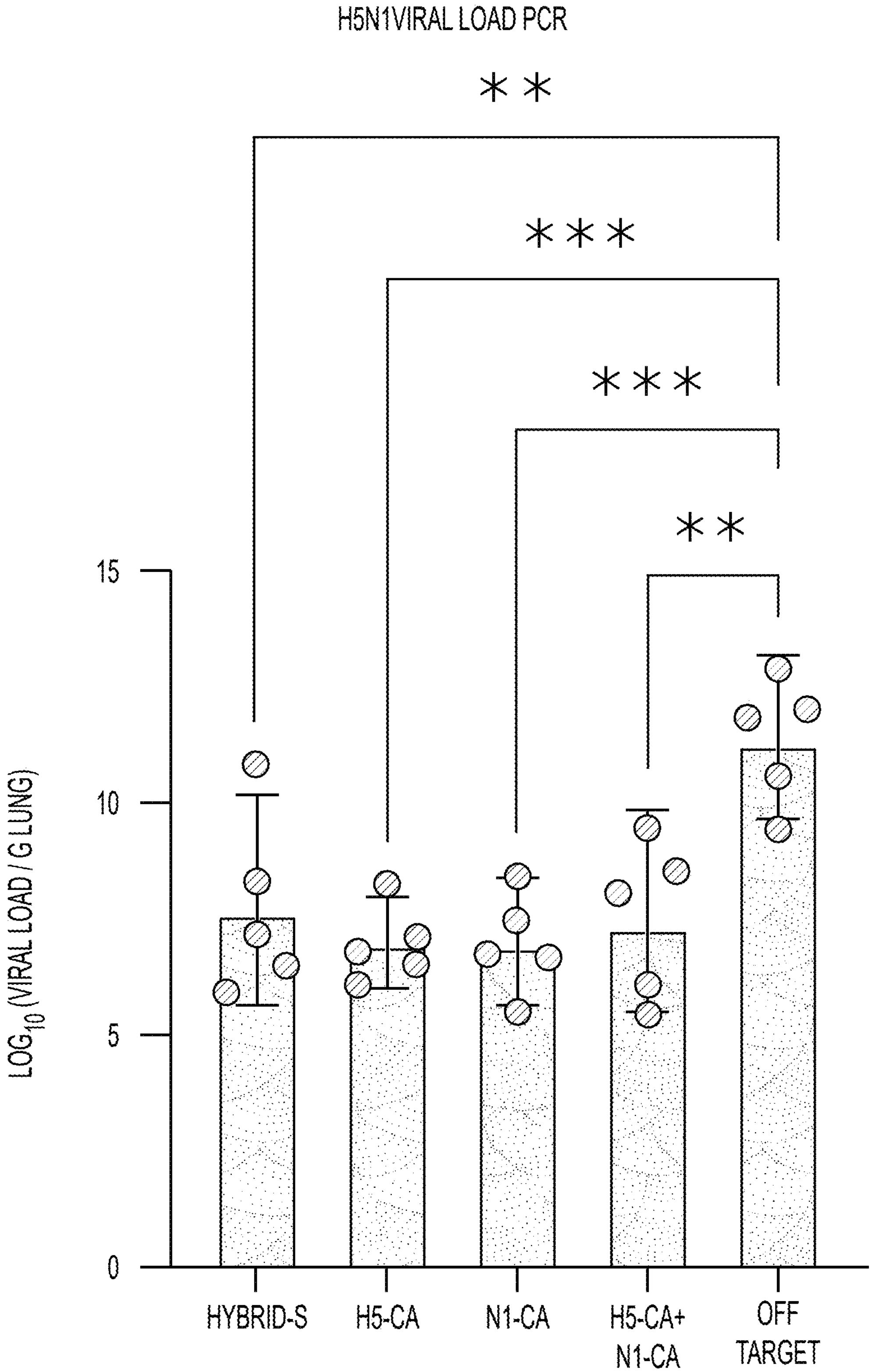
FIG. 15 shows the viral load in lung tissue following H5N1 challenge.

Viral titers were measured by PCR and are expressed as $\log_{10}$ viral load per gram of lung tissue. As seen in FIG. 15, animals immunized with H5-CA, N1-CA, or H5-CA+N1-CA exhibited reduced viral loads to compared to the Off Target control group. Intranasal challenge was with H5N1 (A/Texas/37/2024) at $7.34\times10^3$ $TCID_{50}$/dose 21 days after second immunization. Statistical analysis by ANOVA with multiple comparisons showed significant reductions in viral load for the vaccine-targeted groups relative to the Off Target group (p<0.01, *p<0.001). The Hybrid-S construct reduced viral load by an average of >$10^4$.

List of sequences

| Description | SEQ ID NO: | SEQUENCE |
|---|---|---|
| H5N1 hybrid vaccine antigen with signal peptide | 1 | MENIVLLLAIVSLVKSDQICIGYHANNSTEQVDTIMEKN<br>VTVTHAQDILEKTHNGKLCDLNGVKPLILKDCSVAGW<br>LLGNPMCDEFIRVPEWSYIVERANPANDLCFPGSLNDY<br>EELKHMLSRINHFEKIQIIPKSSWPNHETSLGVSAACPY<br>QGAPSFFRNVVWLIKKNDAYPTIKISYNNTNREDLLILW<br>GIHHSNNAEEQTNLYKNPITYISVGTSTLNQRLAPKIAT<br>RSQVNGQRGRMDFFWTILKPDDAIHFESNGNFIAPEYA<br>YKIVKKGDSTIMKSGVEYGHCNTKCQTPVGAINSSMPF<br>HNIPLTIGECPKYVKSNKLVLATGLRNSPLREKRRKRGL<br>FGAXAGFIEGGWQGMVDGWYGYHHSNEQGSGYAAD<br>KESTQKAIDGVTNKVNSIIDKMNTQFEAVGREFNNLER<br>RIENLNKKMEDGFLDVWTYNAELLVLMENERTLDFHD<br>SNVKNLYDKVRLQLRDNAKELGNGCFEFYHKCDNEC<br>MESVRNGTYDYPQYSEEARLKREEISGVKLESVGTYQI<br>LSAIGGYIPEAPRDGQAYVRKDGEWVLLSTFLGGHSIQ |

-continued

List of sequences

| Description | SEQ ID NO: | SEQUENCE |
|---|---|---|
| | | TGNQYQPEPCNQSIITYENNTWVNQTYINISNTNFLAEQ<br>AVTSVTLAGNSSLCPISGWAIYSKDNGIRIGSKGDVFVI<br>REPFISCSHLECRTFFLTQGALLNDKHSNGTVKDRSPYR<br>TLMSCPVGEAPSPYNSRFESVAWSASACHDGISWLTIGI<br>SGPDNGAVAVLKYNGIITDTIKSWRNNILRTQESECACV<br>NGSCFTVMTDGPSNGQASYKIFKIEKGKVVKSVEMNAP<br>NYHYEECSCYPDAGDIMCVCRDNWHGSNRPWVSFNQ<br>NLEYQIGYICSGIFGDNPRPNDGTGSCSPMPSNGAYGVK<br>GFSFKYGNGVWIGRTKSTSSRSGFEMIWDPNGWTETDS<br>SFSVKQDIVEITDWSGYSGSFVQHPELTGLDCMRPCFW<br>VELIRGRPKENTIWTSGSSISFCGVNSDTVGWSWPDGA<br>ELPFTIDK |
| Signal peptide | 2 | MENIVLLLAIVSLVKS |
| HA1 domain with Y107F mutation | 3 | DQICIGYHANNSTEQVDTIMEKNVTVTHAQDILEKTHN<br>GKLCDLNGVKPLILKDCSVAGWLLGNPMCDEFIR VPEW<br>SYIVERANPANDLCFPGSLNDYEELKHMLSRINHFEKIQI<br>IPKSSWPNHETSLGVSAACPYQGAPSFFRNVVWLIKKND<br>AYPTIKISYNNTNREDLLILWGIHHSNNAEEQTNLYKNPI<br>TYISVGTSTLNQRLAPKIATRSQVNGQRGRMDFFWTILK<br>DDAIHFESNGNFIAPEYAYKIVKKGDSTIMKSGVEYGHC<br>NTKCQTPVGAINSSMPFHNIHPLTIGECPKYVKSNKLVL<br>ATGLRNSPLREKRRKR |
| HA2 domain | 4 | GLFGAXAGFIEGGWQGMVDGWYGYHHSNEQGSGYA<br>ADKESTQKAIDGVTNKVNSIIDKMNTQFEAVGREFNNL<br>ERRIENLNKKMEDGFLDVWTYNAELLVLMENERTLDF<br>HDSNVKNLYDKVRLQLRDNAKELGNGCFEFYHKCDN<br>ECMESVRNGTYDYPQYSEEARLKREEISGVKLESVGTY<br>QIL |
| Foldon/linker region | 5 | SAIGGYIPEAPRDGQAYVRKDGEWVLLSTFLGG |
| The ectodomain of the wild-type NA of H5N1 strain A/Texas/37/2024 | 6 | HSIQTGNQYQPEPCNQSIITYENNTWVNQTYINISNTNF<br>LAEQAVTSVTLAGNSSLCPISGWAIYSKDNGIRIGSKGD<br>VFVIREPFISCSHLECRTFFLTQGALLNDKHSNGTVKDR<br>SPYRTLMSCPVGEAPSPYNSRFESVAWSASACHDGISW<br>LTIGISGPDNGAVAVLKYNGIITDTIKSWRNNILRTQESE<br>CACVNGSCFTVMTDGPSNGQASYKIFKIEKGKVVKSVE<br>MNAPNYHYEECSCYPDAGDIMCVCRDNWHGSNRPWV<br>SFNQNLEYQIGYICSGIFGDNPRPNDGTGSCSPMPSNGA<br>YGVKGFSFKYGNGVWIGRTKSTSSRSGFEMIWDPNGW<br>TETDSSFSVKQDIVEITDWSGYSGSFVQHPELTGLDCMR<br>PCFWVELIRGRPKENTIWTSGSSISFCGVNSDTVGWSWP<br>DGAELPFTIDK |
| Complete amino acid sequence of wild-type HA of H5N1 strain A/Texas/37/2024 | 7 | MENIVLLLAIVSLVKSDQICIGYHANNSTEQVDTIMEKN<br>VTVTHAQDILEKTHNGKLCDLNGVKPLILKDCSVAGW<br>LLGNPMCDEFIRVPEWSYIEVERANPANDLCYPGSLNDY<br>EELKHMLSRINHFEKIQIIPKSSWPNHETSLGVSAACPY<br>QGAPSFFRNVVWLIKKNDAYPTIKSIYNNTNREDLLILW<br>GIHHSNNAEEQTNLYKNPITYISVGTSTLNQRLAPKIAT<br>RSQVNGQRGRMDFFWTILKPDDAIHFESNGNFIAPEYA<br>YKIVKKGDSTIMKSGVEYGHCNTKCQTPVGAINSSMPF<br>HNIHPLTIGECPKYVKSNKLVLATGLRNSPLREKRRKR<br>GLFGAXAGFIEGGWQGMVDGWYGYHHSNEQGSGYA<br>ADKESTQKAIDGVTNKVNSIIDKMNTQFEAVGREFNNL<br>ERRIENLNKKMEDGFLDVWTYNAELLVLMENERTLDF<br>HDSNVKNLYDKVRLQLRDNAKELGNGCFEFYHKCDN<br>ECMESVRNGTYDYPQYSEEARLKREEISGVKLESVGTY<br>QILSIYSTAASSLALAIMMAGLSLWMCSNGSLQCRICI |
| Complete nucleotide sequence of wild-type HA of H5N1 strain A/Texas/37/2024 | 8 | ggttcactctgtcaaaatggagaacatagtactacttcttgcaatagttagccttgttaaaa<br>gtgatcagatttgcattggttaccatgcaaacaattcgacagagcaagttgacacgataat<br>ggaaaagaacgtcactgttacacatgcccaagacatactggaaaaacacacaacgg<br>gaagctatgcgacctaaatggggtgaagccactgattttaaaggactgcagtgtagctg<br>gatggctcctcggaaacccaatgtgcgacgaattcatcagagtgccggaatggtcttac<br>atagtggagcgggctaacccagctaatgacctctgttacccagggagcctcaatgacta<br>tgaagaactgaaacacatgttgagcagaataaatcattttgagaagattcagatcattccc<br>aagagttcctggccaaatcatgaaacatcactaggggtgagcgcagcttgtccatacca<br>gggagcaccctcctttttcagaaatgtggtgtggcttatcaaaaagaacgatgcataccc<br>aacaataaagataagctacaataatactaatcgggaagatctcttgatactgtgggggatt<br>catcattccaacaatgcagaagagcagacaaatctctacaaaaacccaatcacctacatt<br>tcagttggaacatcaactttaaaccagaggttggcaccaaaaatagctactagatcccaa |

-continued

List of sequences

| Description | SEQ ID NO: | SEQUENCE |
|---|---|---|
| | | gtaaacgggcaacgtggaagaatggacttcttctggacaatcttaaaaccagatgatgc<br>aatccatttcgagagtaacggaaatttcattgctccagagtatgcatacaaaattgttaaga<br>aaggggactcgacaattatgaaaagtggagtggaatatggccactgcaacaccaaatg<br>tcaaaccccagtaggtgcgataaattctagtatgccatttcacaacatacatcctctcacc<br>attggggaatgccccaaatacgtgaaatcaaacaagttggtccttgcgactgggctcag<br>aaatagtcctctaagagaaaagagaagaaaaagaggtctgtttggggcgawagcagg<br>gtttatagagggaggatggcagggaatggttgatggttggtatgggtaccatcatagca<br>atgagcaggggagtgggtacgctgcggacaaagaatccacccaaaaggcaatagatg<br>gagttaccaataaggtcaactcaatcattgacaaaatgaacactcaatttgaggcagttg<br>gaagggagtttaataacttagaaaggaggatagagaatttgaacaagaaaatggaaga<br>cggattcctagatgtctggacctataatgctgaacttctagttctcatggaaaacgagagg<br>actctagatttccatgattcaaatgtcaagaacctttacgacaaagtcagattacagcttag<br>ggataatgcaaaggagctgggtaacggctgtttcgaattctatcacaaatgtgataatga<br>atgtatggaaagtgtgagaaatgggacgtatgactaccctcagtattcagaagaagcaa<br>gattaaaaagagaagaaataagcggagtgaaattagaatcagtaggaacttaccagata<br>ctgtcaatttattcaacagcggcaagttccctagcactggcaatcatgatggctggtctat<br>ctttatggatgtgctccaatgggtcgttacaatgcagaatttgcatttagatttatgagctca<br>gattgtagttaaaaacac |
| Complete amino acid sequence of wild-type NA of H5N1 strain A/Texas/37/2024 | 9 | MNPNQKITTIGSICMVIGIVSLMLQIGNIISIWVSHSIQTG<br>NQYQPEPCNQSIITYENNTWVNQTYINISNTNFLAEQAV<br>TSVTLAGNSSLCPISGWAIYSKDNGIRIGSKGDVFVIREP<br>FISCSHLECRTFFLTQGALLNDKHSNGTVKDRSPYRTL<br>MSCPVGEAPSPYNSRFESVAWSASACHDGISWLTIGISG<br>PDNGAVAVLKYNGIITDTIKSWRNNILRTQESECACVN<br>GSCFTVMTDGPSNGQASYKIFKIEKGKVVKSVEMNAPN<br>YHYEECSCYPDAGDIMCVCRDNWHGSNRPWVSFNON<br>LEYQIGYICSGIFGDNPRPNDGTGSCSPMPSNGAYGVKG<br>FSFKYGNGVWIGRTKSTSSRSGFEMIWDPNGWTETDSS<br>FSVKQDIVEITDWSGYSGSFVQHPELTGLDCMRPCFWV<br>ELIRGRPKENTIWTSGSSISFCGVNSDTVGWSWPDGAEL<br>PFTIDK |
| Complete nucleotide sequence of wild-type NA of H5N1 strain A/Texas/37/2024 | 10 | agttcaaaatgaatccaaatcaaaagataacaaccattggatcaatctgtatggtaattgg<br>gatagtcagcttgatgctgcaaattgggaacataatctcaatatgggttagccattcaatc<br>caaacagggaatcaataccagcctgaaccatgcaatcaaagcatcattacctatgagaa<br>caacacctgggtaaatcagacgtatatcaacatcagcaataccaatttcttgctgagcag<br>gctgttacttcggtaacattagcgggcaattcatctctttgccctattagtgggggcaat<br>atacagtaaggacaacggtataagaattgggtctaaggggatgtgtttgttataagaga<br>accattcatctcatgctcccacttggaatgcagaacctttttcctgacccagggagctctg<br>ctgaatgacaaacattctaatgggacagttaaggatagaagcccttatagaactttgatga<br>gttgtcccgtgggtgaggctccttccccgtacaattcaagatttgagtctgttgcttggtcg<br>gcaagtgcttgtcatgatggcatcagttggttgacaatcggtatttctggtccagacaatg<br>gagctgtggctgtattgaagtacaatggcataataacggatactatcaagagttggagaa<br>acaacattttgagaactcaagaatctgaatgtgcttgcgtaaatggctcctgcttcaccgta<br>atgactgatggaccaagcaatgggcaggcctcatataaaatcttcaagatagagaaagg<br>gaaagttgtcaaatcagttgaaatgaatgcccctaattaccactacgaggaatgctcctgt<br>tatcctgatgcgggtgatattatgtgtgtgtgcagggacaattggcatggctcgaaccgg<br>ccgtgggtatcttttaatcaaaatctggagtatcaaataggatatatatgcagtgggatttc<br>ggggacaatccccgccccaatgatggaacaggcagttgcagtccaatgccctctaatg<br>gggcatatggggtgaaagggttttcatttaagtacggtaatggggtttggatcggaagaa<br>caaaaagcactagttccagaagcggctttgagatgatttgggatccgaatgggtggact<br>gagacagacagtagtttctcagtgaagcaagacattgtagaaataactgactggtcagg<br>atatagtgggagttttgtccagcatccagaactgacaggattagattgcatgaggccttgt<br>ttctgggttgagctaattagagggaggcccaaagagaatacaatttggactagcgggag<br>cagcatatccttttgtggtgtaaatagtgacactgtgggttggtcttggccagacggtgct<br>gagttgccattcaccattgacaagtagtttgttcaaaaaact |
| linker/thrombin/his tag/strep tag | 11 | GGLVPRGSHHHHHHSAWSHPQFEK |
| Polybasic cleavage site of the HA of H5N1 strain A/Texas/37/2024 | 12 | KRRKR |
| H5N1 hybrid vaccine antigen without signal peptide | 13 | DQICIGYHANNSTEQVDTIMEKNVTVTHAQDILEKTHN<br>GKLCDLNGVKPLILKDCSVAGWLLGNPMCDEFIRVPE<br>WSYIVERANPANDLCFPGSLNDYEELKHMLSRINHFEKI<br>QIIPKSSWPNHETSLGVSAACPYQGAPSFFRNVVWLIKK<br>NDAYPTIKISYNNTNREDLLILWGIHHSNNAEEQTNLYK<br>NPITYISVGTSTLNQRLAPKIATRSQVNGQRGRMDFFW<br>TILKPDDAIHFESNGNFIAPEYAYKIVKKGDSTIMKSGV<br>EYGHCNTKCQTPVGAINSSMPFHNIHPLTIGECPKYVKS<br>NKLVLATGLRNSPLREKRRKRGLFGAXAGFIEGGWQG<br>MVDGWYGYHHSNEQGSGYAADKESTQKAIDGVTNKV |

-continued

List of sequences

| Description | SEQ ID NO: | SEQUENCE |
|---|---|---|
| | | NSIIDKMNTQFEAVGREFNNLERRIENLNKKMEDGELD<br>VWTYNAELLVLMENERTLDFHDSNVKNLYDKVRLQL<br>RDNAKELGNGCFEFYHKCDNECMESVRNGTYDYPQYS<br>EEARLKREEISGVKLESVGTYQILSAIGGYIPEAPRDGQ<br>AYVRKDGEWVLLSTFLGGHSIQTGNQYQPEPCNQSIIT<br>YENNTWVNQTYINISNTNFLAEQAVTSVTLAGNSSLCPI<br>SGWAIYSKDNGIRIGSKGDVFVIREPFISCSHLECRTFFL<br>TQGALLNDKHSNGTVKDRSPYRTLMSCPVGEAPSPYNS<br>RFESVAWSASACHDGISWLTIGISGPDNGAVAVLKYNG<br>IITDTIKSWRNNILRTQESECACVNGSCFTVMTDGPSNG<br>QASYKIFKIEKGKVVKSVEMNAPNYHYEECSCYPDAG<br>DIMCVCRDNWHGSNRPWVSFNQNLEYQIGYICSGIFGD<br>NPRPNDGTGSCSPMPSNGAYGVKGFSFKYGNGVWIGR<br>TKSTSSRSGFEMIWDPNGWTETDSSFSVKQDIVEITDWS<br>GYSGSFVQHPELTGLDCMRPCFWVELIRGRPKENTIWT<br>SGSSISFCGVNSDTVGWSWPDGAELPFTIDK |
| Linker Sequence | 14 | GGGGS |
| Linker Sequence | 15 | GSGS |
| H5N1 hybrid vaccine antigen (Hybrid-S) with signal peptide | 16 | MENIVLLLAIVSLVKSDQICIGYHANNSTEQVDTIMEKN<br>VTVTHAQDILEKTHNGKLCDLNGVKPLILKDCSVAGWL<br>LGNPMCDEFIRVPEWSYIVERANPANDLCFPGSLNDYEE<br>LKHMLSRINHFEKIQIIPKSSWPNHETSLGVSAACPYQGA<br>PSFFRNVVWLIKKNDAYPTIKISYNNTNREDLLILWGIHH<br>SNNAEEQTNLYKNPITYISVGTSTLNQRLAPKIATRSQVN<br>GQRGRMDFFWTILKPDDAIHFESNGNFIAPEYAYKIVKK<br>GDSTIMKSGVEYGHCNTKCQTPVGAINSSMPFHNIHPLTI<br>GECPKYVKSNKLVLATGLRNSPLREKRRKRGLFGAIAGF<br>IEGGWQGMVDGWYGYHHSNEQGSGYAADKESTQKAI<br>DGVTNKVNSIIDKMNTQFEAVGREFNNLERRIENLNKK<br>MEDGFLDVWTYNAELLVLMENERTLDFHDSNVKNLYD<br>KVRLQLRDNAKELGNGCFEFYHKCDNECMESVRNGTY<br>DYPQYSEEARLKREEISGVKLESVGTYQILSAIGGYIPEA<br>PRDGQAYVRKDGEWVLLSTFLGGHSIQTGNQYQPEPCN<br>QSIITYENNTWVNQTYINISNTNFLAEQAVTSVTLAGNSS<br>LCPISGWAIYSKDNGIRIGSKGDVFVIREPFISCSHLECRT<br>FFLTQGALLNDKHSNGTVKDRSPYRTLMSCPVGEAPSP<br>YNSRFESVAWSASACHDGISWLTIGISGPDNGAVAVLKY<br>NGIITDTIKSWRNNILRTQESECACVNGSCFTVMTDGPSN<br>GQASYKIFKIEKGKVVKSVEMNAPNYHYEECSCYPDAG<br>DIMCVCRDNWHGSNRPWVSFNQNLEYQIGYICSGIFGD<br>NPRPNDGTGSCSPMPSNGAYGVKGFSFKYGNGVWIGRT<br>KSTSSRSGFEMIWDPNGWTETDSSFSVKQDIVEITDWSG<br>YSGSFVQHPELTGLDCMRPCFWVELIRGRPKENTIWTSG<br>SSISFCGVNSDTVGWSWPDGAELPFTIDK |
| Full length HA-A/Texas/37/2024 | 17 | MENIVLLLAIVSLVKSDQICIGYHANNSTEQVDTIMEKN<br>VTVTHAQDILEKTHNGKLCDLNGVKPLILKDCSVAGWL<br>LGNPMCDEFIRVPEWSYIVERANPANDLCFPGSLNDYEE<br>LKHMLSRINHFEKIQIIPKSSWPNHETSLGVSAACPYQGA<br>PSFFRNVVWLIKKNDAYPTIKISYNNTNREDLLILWGIHH<br>SNNAEEQTNLYKNPITYISVGTSTLNQRLAPKIATRSQVN<br>GQRGRMDFFWTILKPDDAIHFESNGNFIAPEYAYKIVKK<br>GDSTIMKSGVEYGHCNTKCQTPVGAINSSMPFHNIHPLTI<br>GECPKYVKSNKLVLATGLRNSPLREKRRKRGLFGAIAGF<br>IEGGWQGMVDGWYGYHHSNEQGSGYAADKESTQKAI<br>DGVTNKVNSIIDKMNTQFEAVGREFNNLERRIENLNKK<br>MEDGFLDVWTYNAELLVLMENERTLDFHDSNVKNLYD<br>KVRLQLRDNAKELGNGCFEFYHKCDNECMESVRNGTY<br>DYPQYSEEARLKREEISGVKLESVGTYQILSIYSTAASSL<br>ALAIMMAGLSLWMCSNGSLQCRICI |
| Full length NA-A/Texas/37/2024 | 18 | MNPNQKITTIGSICMVIGIVSLMLQIGNIISIWVSHSIQTGN<br>QYQPEPCNQSIITYENNTWVNQTYINISNTNFLAEQAVTS<br>VTLAGNSSLCPISGWAIYSKDNGIRIGSKGDVFVIREPFIS<br>CSHLECRTFFLTQGALLNDKHSNGTVKDRSPYRTLMSCP<br>VGEAPSPYNSRESVAWSASACHDGISWLTIGISGPDNG<br>AVAVLKYNGIITDTIKSWRNNILRTQESECACVNGSCFT<br>VMTDGPSNGQASYKIFKIEKGKVVKSVEMNAPNYHYEE<br>CSCYPDAGDMICCVCRDNWHGSNRPWVSFNQNLEYQIG<br>YICSGIFGDNPRPNDGTGSCSPMPSNGAYGVKGFSFKYG<br>NGVWIGRTKSTSSRSGFEMIWDPNGWTETDSSFSVKQDI |

-continued

| List of sequences | | |
|---|---|---|
| Description | SEQ ID NO: | SEQUENCE |
| | | VEITDWSGYSGSFVQHPELTGLDCMRPCFWVELIRGRPK ENTIWTSGSSISFCGVNSDTVGWSWPDGAELPFTIDK |
| HA + GS linker + NA (hybrid TM) with signal peptide | 19 | MENIVLLLAIVSLVKSDQICIGYHANNSTEQVDTIMEKN VTVTHAQDILEKTHNGKLCDLNGVKPLILKDCSVAGWL LGNPMCDEFIRVPEWSYIVERANPANDLCFPGSLNDYEE LKHMLSRINHFEKIQIIPKSSWPNHETSLGVSAACPYQGA PSFFRNVVWLIKKNDAYPTIKISYNNTNREDLLILWGIHH SNNAEEQTNLYKNPITYISVGTSTLNQRLAPKIATRSQVN GQRGRMDFFWTILKPDDAIHFESNGNFIAPEYAYKIVKK GDSTIMKSGVEYGHCNTKCQTPVGAINSSMPFHNIHPLTI GECPKYVKSNKLVLATGLRNSPLREKRRKRGLFGAIAGF IEGGWQGMVDGWYGYHHSNEQGSGYAADKESTQKAI DGVTNKVNSIIDKMTQFEAVGREFNNLERRIENLNKK MEDGFLDVWTYNAELLVLMENERTLDFHDSNVKNLYD KVRLQLRDNAKELGNGCFEFYHKCDNECMESVRNGTY DYPQYSEEARLKREEISGVKLESVGTYQILSIYSTAASSL ALAIMMAGLSLWMCSNGSLQCRICIGGSGGSGGSGGSG SGMNPNQKITTIGSICMVIGIVSLMLQIGNIISIWVSHSIQT GNQYQPEPVNQSIITYENNTWVNQTYINISNTNFLAEQA VTSVTLAGNSSLCPISGWAIYSKDNGIRIGSKGDVFVIRE PFISCSHLECRTFFLTQGALLNDKHSNGTVKDRSPYRTL MSCPVGEAPSPYNSRFESVAWSASACHDGISWLTIGISGP DNGAVAVLKYNGIITDTIKSWRNNILRTQESECACVNGS CFTVMTDGPSNGQASYKIFKIEKGKVVKSVEMNAPNYH YEECSCYPDAGDIMCVCRDNWHGSNRPWVSFNQNLEY QIGYICSGIFGDNPRPNDGTGSCSPMPSNGAYGVKGFSF KYGNGVWIGRTKSTSSRSGFEMIWDPNGWTETDSSFSV KQDIVEITDWSGYSGSFVQHPELTGLDCMRPCFWVELIR GRPKENTIWTSGSSISFCGVNSDTVGWSWPDGAELPFTI DK |
| HA + GS linker + Foldon + GS linker+ NA (Hybrid-TM with foldon) with signal peptide | 20 | MENIVLLLAIVSLVKSDQICIGYHANNSTEQVDTIMEKN VTVTHAQDILEKTHNGKLCDLNGVKPLILKDCSVAGWL LGNPMCDEFIRVPEWSYIVERANPANDLCFPGSLNDYEE LKHMLSRINHFEKIQIIPKSSWPNHETSLGVSAACPYQGA PSFFRNVVWLIKKNDAYPTIKISYNNTNREDLLILWGIHH SNNAEEQTNLYKNPITYISVGTSTLNQRLAPKIATRSQVN GQRGRMDFFWTILKPDDAIHFESNGNFIAPEYAYKIVKK GDSTIMKSGVEYGHCNTKCQTPVGAINSSMPFHNIHPLTI GECPKYVKSNKLVLATGLRNSPLREKRRKRGLFGAIAGF IEGGWQGMVDGWYGYHHSNEQGSGYAADKESTQKAI DGVTNKVNSIIDKMNTQFEAVGREFNNLERRIENLNKK MEDGFLDVWTYNAELLVLMENERTLDFHDSNVKNLYD KVRLQLRDNAKELGNGCFEFYHKCDNECMESVRNGTY DYPQYSEEARLKREEISGVKLESVGTYQILSIYSTAASSL ALAIMMAGLSLWMCSNGSLQCRICIGSGSAIGGYIPEAP RDGQAYVRKDGEWVLLSTFLGMNPNQKITTIGSICMVIG IVSLMLQIGNIISIWVSHSIQTGNQYQPEPCNQSIITYENN TWVNQTYINISNTNFLAEQAVTSVTLAGNSSLCPISGWAI YSKDNGIRIGSKGDVFVIREPFISCSHLECRTFFLTQGALL NDKHSNGTVKDRSPYRTLMSCPVGEAPSPYNSRFESVA WSASACHDGISWLTIGISGPDNGAVAVLKYNGIITDTIKS WRNNILRTQESECACVNGSCFTVMTDGPSNGQASYKIF KIEKGKVVKSVEMNAPNYHYEECSCYPDAGDIMCVCR DNWHGSNRPWVSFNQNLEYQIGYICSGIFGDNPRPNDG TGSCSPMPSNGAYGVKGFSFKYGNGVWIGRTKSTSSRS GFEMIWDPNGWTETDSSFSVKQDIVEITDWSGYSGSFVQ HPELTGLDCMRPCFWVELIRGRPKENTIWTSGSSISFCGV NSDTVGWSWPDGAELPFTIDK |
| linker/thrombin/his tag/strep tag | 21 | GGLVPRGSHHHHHHSAWSHPQFEK |
| H5N1 vaccine antigen + linker/thrombin/his tag/strep tag (Hybrid-S + purification tags) with signal peptide | 22 | MENIVLLLAIVSLVKSDQICIGYHANNSTEQVDTIMEKN VTVTHAQDILEKTHNGKLCDLNGVKPLILKDCSVAGWL LGNPMCDEFIRVPEWSYIVERANPANDLCFPGSLNDYEE LKHMLSRINHFEKIQIIPKSSWPNHETSLGVSAACPYQGA PSFFRNVVWLIKKNDAYPTIKISYNNTNREDLLILWGIHH SNNAEEQTNLYKNPITYISVGTSTLNQRLAPKIATRSQVN GQRGRMDFFWTILKPDDAIHFESNGNFIAPEYAYKIVKK GDSTIMKSGVEYGHCNTKCQTPVGAINSSMPFHNIHPLTI GECPKYVKSNKLVLATGLRNSPLREKRRKRGLFGAIAGF IEGGWQGMVDGWYGYHHSNEQGSGYAADKESTQKAI DGVTNKVNSIIDKMNTQFEAVGREFNNLERRIENLNKK |

-continued

List of sequences

| Description | SEQ ID NO: | SEQUENCE |
|---|---|---|
| | | MEDGFLDVWTYNAELLVLMENERTLDFHDSNVKNLYD KVRLQLRDNAKELGNGCFEFYHKCDNECMESVRNGTY DYPQYSEEARLKREEISGVKLESVGTYQILSAIGGYIPEA PRDGQAYVRKDGEWVLLSTFLGGHSIQTGNQYQPEPCN QSIITYENNTWVNQTYINISNTNFLAEQAVTSVTLAGNSS LCPISGWAIYSKDNGIRIGSKGDVFVIREPFISCSHLECRT FFLTQGALLNDKHSNGTVKDRSPYRTLMSCPVGEAPSP YNSRFESVAWSASACHDGISWLTIGISGPDNGAVAVLKY NGIITDTIKSWRNNILRTQESECACVNGSCFTVMTDGPSN GQASYKIFKIEKGKVVKSVEMNAPNYHYEECSCYPDAG DIMCVCRDNWHGSNRPWVSFNQNLEYQIGYICSGIFGD NPRPNDGTGSCSPMPSNGAYGVKGFSFKYGNGVWIGRT KSTSSRSGFEMIWDPNGWTETDSSFSVKQDIVEITDWSG YSGSFVQHPELTGLDCMRPCFWVELIRGRPKENTIWTSG SSISFCGVNSDTVGWSWPDGAELPFTIDKGGLVPRGSHH HHHHSAWSHPQFEK |
| Mutated H5N1 Vaccine antigen-alternative HA modified (Hybrid-S mod α-2, 6 binding) with signal peptide | 23 | MENIVLLLAIVSLVKSDQICIGYHANNSTEQVDTIMEKN VTVTHAQDILEKTHNGKLCDLNGVKPLILKDCSVAGWL LGNPMCDEFIRVPEWSYIVERANPANDLCFPGSLNDYEE LKHMLSRINHFEKIQIIPKSSWPNHETSLGVSAACPYQGA PSFFRNVVWLIKKNDAYPTIKISYNNTNREDLLILWGIHH SNNAE**D**QT**D**LYKNPITYISVGTSTLNQRLAPKIATRSQV NG**L**RGRMDFFWTILKPDDAIHFESNGNFIAPEYAYKIVK KGDSTIMKSGVEYGHCNTKCQTPVGAINSSMPFHNIHPL TIGECPKYVKSNKLVLATGLRNSPLREKRRKRGLFGAIA GFIEGGWQGMVDGWYGYHHSNEQGSGYAADKESTQK AIDGVTNKVNSIIDKMNTQFEAVGREFNNLERRIENLNK KMEDGFLDVWTYNAELLVLMENERTLDFHDSNVKNLY DKVRLQLRDNAKELGNGCFEFYHKCDNECMESVRNGT YDYPQYSEEARLKREEISGVKLESVGTYQILSAIGGYIPE APRDGQAYVRKDGEWVLLSTFLGGHSIQTGNQYQPEPC NQSIITYENNTWVNQTYINISNTNFLAEQAVTSVTLAGN SSLCPISGWAIYSKDNGIRIGSKGDVFVIREPFISCSHLEC RTFFLTQGALLNDKHSNGTVKDRSPYRTLMSCPVGEAP SPYNSRFESVAWSASACHDGISWLTIGISGPDNGAVAVL KYNGIITDTIKSWRNNILRTQESECACVNGSCFTVMTDG PSNGQASYKIFKIEKGKVVKSVEMNAPNYHYEECSCYP DAGDIMCVCRDNWHGSNRPWVSFNQNLEYQIGYICFGI FGDNPRPNDGTGSCSPMPSNGAYGVKGFSFKYGNGVWI GRTKSTSSRSGFEMIWDPNGWTETDSSFSVKQDIVEITD WSGYSGSFVQHPELTGLDCMRPCFWVELIRGRPKENTI WTSGSSISFCGVNSDTVGWSWPDGAELPFTIDK |
| H5N1 hybrid vaccine antigen (Hybrid-S) without signal peptide | 24 | DQICIGYHANNSTEQVDTIMEKNVTVTHAQDILEKTHNG KLCDLNGVKPLILKDCSVAGWLLGNPMCDEFIRVPEWS YIVERANPANDLCFPGSLNDYEELKHMLSRINHFEKIQII PKSSWPNHETSLGVSAACPYQGAPSFFRNVVWLIKKND AYPTIKISYNNTNREDLLILWGIHHSNNAEEQTNLYKNPI TYISVGTSTLNQRLAPKIATRSQVNGQRGRMDFFWTILK PDDAIHFESNGNFIAPEYAYKIVKKGDSTIMKSGVEYGH CNTKCQTPVGAINSSMPFHNIHPLTIGECPKYVKSNKLV LATGLRNSPLREKRRKRGLFGAIAGFIEGGWQGMVDGW YGYHHSNEQGSGYAADKESTQKAIDGVTNKVNSIIDKM NTQFEAVGREFNNLERRIENLNKKMEDGFLDVWTYNAE LLVLMENERTLDFHDSNVKNLYDKVRLQLRDNAKELG NGCFEFYHKCDNECMESVRNGTYDYPQYSEEARLKREE ISGVKLESVGTYQILSAIGGYIPEAPRDGQAYVRKDGEW VLLSTFLGGHSIQTGNQYQPEPCNQSIITYENNTWVNQT YINISNTNFLAEQAVTSVTLAGNSSLCPISGWAIYSKDNG IRIGSKGDVFVIREPFISCSHLECRTFFLTQGALLNDKHSN GTVKDRSPYRTLMSCPVGEAPSPYNSRFESVAWSASAC HDGISWLTIGISGPDNGAVAVLKYNGIITDTIKSWRNNIL RTQESECACVNGSCFTVMTDGPSNGQASYKIFKIEKGKV VKSVEMNAPNYHYEECSCYPDAGDIMCVCRDNWHGSN RPWVSFNQNLEYQIGYICSGIFGDNPRPNDGTGSCSPMPS NGAYGVKGFSFKYGNGVWIGRTKSTSSRSGFEMIWDPN GWTETDSSFSVKQDIVEITDWSGYSGSFVQHPELTGLDC MRPCFWVELIRGRPKENTIWTSGSSISFCGVNSDTVGWS WPDGAELPFTIDK |
| HA + GS linker + NA without signal peptide | 25 | DQICIGYHANNSTEQVDTIMEKNVTVTHAQDILEKTHNG KLCDLNGVKPLILKDCSVAGWLLGNPMCDEFIRVPEWS YIVERANPANDLCFPGSLNDYEELKHMLSRINHFEKIQII PKSSWPNHETSLGVSAACPYQGAPSFFRNVVWLIKKND |

-continued

List of sequences

| Description | SEQ ID NO: | SEQUENCE |
|---|---|---|
| | | AYPTIKISYNNTNREDLLILWGIHHSNNAEEQTNLYKNPI TYISVGTSTLNQRLAPKIATRSQVNGQRGRMDFFWTILK PDDAIHFESNGNFIAPEYAYKIVKKGDSTIMKSGVEYGH CNTKCQTPVGAINSSMPFHNIHPLTIGECPKYVKSNKLV LATGLRNSPLREKRRKRGLFGAIAGFIEGGWQGMVDGW YGYHHSNEQGSGYAADKESTQKAIDGVTNKVNSIIDKM NTQFEAVGREFNNLERRIENLNKKMEDGFLDVWTYNAE LLVLMENERTLDFHDSNVKNLYDKVRLQLRDNAKELG NGCFEFYHKCDNECMESVRNGTYDYPQYSEEARLKREE ISGVKLESVGTYQILSIYSTAASSLALAIMMAGLSLWMC SNGSLQCRICIGGSGGSGGSGGSGSGMNPNQKITTIGSIC MVIGIVSLMLQIGNIISIWVSHSIQTGNQYQPEPCNQSIIT YENNTWVNQTYINISNTNFLAEQAVTSVTLAGNSSLCPI SGWAIYSKDNGIRIGSKGDVFVIREPFISCSHLECRTFFLT QGALLNDKHSNGTVKDRSPYRTLMSCPVGEAPSPYNSR FESVAWSASACHDGISWLTIGISGPDNGAVAVLKYNGII TDTIKSWRNNILRTQESECACVNGSCFTVMTDGPSNGQ ASYKIFKIEKGKVVKSVEMNAPNYHYEECSCYPDAGDI MCVCRDNWHGSNRPWVSFNQNLEYQIGYICSGIFGDNP RPNDGTGSCSPMPSNGAYGVKGFSFKYGNGVWIGRTKS TSSRSGFEMIWDPNGWTETDSSFSVKQDIVEITDWSGYS GSFVQHPELTGLDCMRPCFWVELIRGRPKENTIWTSGSSI SFCGVNSDTVGWSWPDGAELPFTIDK |
| HA + GS linker + Foldon + GS linker + NA without signal peptide | 26 | DQICIGYHANNSTEQVDTIMEKNVTVTHAQDILEKTHNG KLCDLNGVKPLILKDCSVAGWLLGNPMCDEFIRVPEWS YIVERANPANDLCFPGSLNDYEELKHMLSRINHFEKIQII PKSSWPNHETSLGVSAACPYQGAPSFFRNVVWLIKKND AYPTIKISYNNTNREDLLILWGIHHSNNAEEQTNLYKNPI TYISVGTSTLNQRLAPKIATRSQVNGQRGRMDFFWTILK PDDAIHFESNGNFIAPEYAYKIVKKGDSTIMKSGVEYGH CNTKCQTPVGAINSSMPFHNIHPLTIGECPKYVKSNKLV LATGLRNSPLREKRRKRGLFGAIAGFIEGGWQGMVDGW YGYHHSNEQGSGYAADKESTQKAIDGVTNKVNSIIDKM NTQFEAVGREFNNLERRIENLNKKMEDGFLDVWTYNAE LLVLMENERTLDFHDSNVKNLYDKVRLQLRDNAKELG NGCFEFYHKCDNECMESVRNGTYDYPQYSEEARLKREE ISGVKLESVGTYQILSIYSTAASSLALAIMMAGLSLWMC SNGSLQCRICIGSGSAIGGYIPEAPRDGQAYVRKDGEWV LLSTFLGMNPNQKITTIGSICMVIGIVSLMLQIGNIISIWVS HSIQTGNQYQPEPCNQSIITYENNTWVNQTYINISNTNFL AEQAVTSVTLAGNSSLCPISGWAIYSKDNGIRIGSKGDVF VIREPFISCSHLECRTFFLTQGALLNDKHSNGTVKDRSPY RTLMSCPVGEAPSPYNSRFESVAWSASACHDGISWLTIG ISGPDNGAVAVLKYNGIITDTIKSWRNNILRTQESECACV NGSCFTVMTDGPSNGQASYKIFKIEKGKVVKSVEMNAP NYHYEECSCYPDAGDIMCVCRDNWHGSNRPWVSFNON LEYQIGYICSGIFGDNPRPNDGTGSCSPMPSNGAYGVKG FSFKYGNGVWIGRTKSTSSRSGFEMIWDPNGWTETDSSF SVKQDIVEITDWSGYSGSFVQHPELTGLDCMRPCFWVE LIRGRPKENTIWTSGSSISFCGVNSDTVGWSWPDGAELP FTIDK |
| H5N1 vaccine antigen + linker/thrombin/his tag/strep tag (Hybrid-S + purification tags) without signal peptide | 27 | DQICIGYHANNSTEQVDTIMEKNVTVTHAQDILEKTHNG KLCDLNGVKPLILKDCSVAGWLLGNPMCDEFIRVPEWS YIVERANPANDLCFPGSLNDYEELKHMLSRINHFEKIQII PKSSWPNHETSLGVSAACPYQGAPSFFRNVVWLIKKND AYPTIKISYNNTNREDLLILWGIHHSNNAEEQTNLYKNPI TYISVGTSTLNQRLAPKIATRSQVNGQRGRMDFFWTILK PDDAIHFESNGNFIAPEYAYKIVKKGDSTIMKSGVEYGH CNTKCQTPVGAINSSMPFHNIHPLTIGECPKYVKSNKLV LATGLRNSPLREKRRKRGLFGAIAGFIEGGWQGMVDGW YGYHHSNEQGSGYAADKESTQKAIDGVTNKVNSIIDKM NTQFEAVGREFNNLERRIENLNKKMEDGFLDVWTYNAE LLVLMENERTLDFHDSNVKNLYDKVRLQLRDNAKELG NGCFEFYHKCDNECMESVRNGTYDYPQYSEEARLKREE ISGVKLESVGTYQILSAIGGYIPEAPRDGQAYVRKDGEW VLLSTFLGGHSIQTGNQYQPEPCNQSIITYENNTWVNQT YINISNTFLAEQAVTSVTLAGNSSLCPISGWAIYSKDNG IRIGSKGDVFVIREPFISCSHLECRTFFLTQGALLNDKHSN GTVKDRSPYRTLMSCPVGEAPSPYNSRFESVAWSASAC HDGISWLTIGISGPDNGAVAVLKYNGIITDTIKSWRNNIL RTQESECACVNGSCFTVMTDGPSNGQASYKIFKIEKGKV VKSVEMNAPNYHYEECSCYPDAGDIMCVCRDNWHGSN RPWVSFNQNLEYQIGYICFGIFGDNPRPNDGTGSCSPMP |

-continued

List of sequences

| Description | SEQ ID NO: | SEQUENCE |
|---|---|---|
| | | SNGAYGVKGFSFKYGNGVWIGRTKSTSSRSGFEMIWDP<br>NGWTETDSSFSVKQDIVEITDWSGYSGSFVQHPELTGLD<br>CMRPCFWVELIRGRPKENTIWTSGSSISFCGVNSDTVGW<br>SWPDGAELPFTIDK |
| Mutated H5N1 Vaccine antigen-alternative HA modified (Hybrid-S mod α-2,6 binding) without signal peptide | 28 | DQICIGYHANNSTEQVDTIMEKNVTVTHAQDILEKTHNG<br>KLCDLNGVKPLILKDCSVAGWLLGNPMCDEFIRVPEWS<br>YIVERANPANDLCFPGSLNDYEELKHMLSRINHFEKIQII<br>PKSSWPNHETSLGVSAACPYQGAPSFFRNVVWLIKKND<br>AYPTIKISYNNTNREDLLILWGIHHSNNAE**D**QT**D**LYKNPI<br>TYISVGTSTLNQRLAPKIATRSQVNG**L**RGRMDFFWTILK<br>PDDAIHFESNGNFIAPEYAYKIVKKGDSTIMKSGVEYGH<br>CNTKCQTPVGAINSSMPFHNIHPLTIGECPKYVKSNKLV<br>LATGLRNSPLREKRRKRGLFGAIAGFIEGGWQGMVDGW<br>YGYHHSNEQGSGYAADKESTQKAIDGVTNKVNSIIDKM<br>NTQFEAVGREFNNLERRIENLNKKMEDGFLDVWTYNAE<br>LLVLMENERTLDFHDSNVKNLYDKVRLQLRDNAKELG<br>NGCFEFYHKCDNECMESVRNGTYDYPQYSEEARLKREE<br>ISGVKLESVGTYQILSAIGGYIPEAPRDGQAYVRKDGEW<br>VLLSTFLGGHSIQTGNQYQPEPCNQSIITYENNTWVNQT<br>YINISNTNFLAEQAVTSVTLAGNSSLCPISGWAIYSKDNG<br>IRIGSKGDVFVIREPFISCSHLECRTFFLTQGALLNDKHSN<br>GTVKDRSPYRTLMSCPVGEAPSPYNSRFESVAWSASAC<br>HDGISWLTIGISGPDNGAVAVLKYNGIITDTIKSWRNNIL<br>RTQESECACVNGSCFTVMTDGPSNGQASYKIFKIEKGKV<br>VKSVEMNAPNYHYEECSCYPDAGDIMCVCRDNWHGSN<br>RPWVSFNQNLEYQIGYICFGI**F**GDNPRPNDGTGSCSPMP<br>SNGAYGVKGFSKKYGNGVWIGRTKSTSSRSGFEMIWDP<br>NGWTETDSSFSVKQDIVEITDWSGYSGSFVQHPELTGLD<br>CMRPCFWVELIRGRPKENTIWTSGSSISFCGVNSDTVGW<br>SWPDGAELPFTIDK |

While various embodiments have been described above, it should be understood that such disclosures have been presented by way of example only and are not limiting. Thus, the breadth and scope of the subject compositions and methods should not be limited by any of the above-described exemplary embodiments but should be defined only in accordance with the following claims and their equivalents.

The above description is for the purpose of teaching the person of ordinary skill in the art how to practice the present application, and it is not intended to detail all those obvious modifications and variations of it which will become apparent to the skilled worker upon reading the description. It is intended, however, that all such obvious modifications and variations be included within the scope of the present application, which is defined by the following claims. The claims are intended to cover the components and steps in any sequence which is effective to meet the objectives there intended, unless the context specifically indicates the contrary.

What is claimed is:

1. A method for reducing viral load resulting from infection with an influenza virus in a subject in need thereof, comprising:

administering to the subject in need thereof an effective amount of a pharmaceutical composition comprising:

1) a hybrid protein comprising:

a) a first domain comprising an ectodomain of an influenza hemagglutinin (HA) protein; and b) a second domain comprising an ectodomain of an influenza neuraminidase (NA) protein, wherein the second domain is located at the C-terminal of the first domain; and 2) a pharmaceutically acceptable carrier.

2. The method of claim 1, wherein the influenza virus infection is influenza A or influenza B.

3. The method of claim 2, wherein the influenza A virus is selected from the group consisting of H1N1, H1N3, H3N2, H3N8, H5N1, H5N6, and H7N9.

4. The method of claim 1, wherein the HA comprises a mutation that reduces aggregation and non-specific binding to sialic acid.

5. The method of claim 1, wherein a cleavage site of HA is replaced with a linker sequence.

6. The method of claim 1, wherein the hybrid protein comprises SEQ ID NO: 13.

7. The method of claim 1, wherein the hybrid protein comprises the sequence selected from the group consisting of SEQ ID NOS: 24-27.

8. A method for increasing immunity to an influenza virus infection in a subject in need thereof, comprising:

administering to the subject in need thereof an effective amount of a pharmaceutical composition comprising:

1) a hybrid protein comprising:

a) a first domain comprising an ectodomain of an influenza hemagglutinin (HA) protein; and b) a second domain comprising an ectodomain of an influenza neuraminidase (NA) protein, wherein the second domain is located at the C-terminal of the first domain; and 2) a pharmaceutically acceptable carrier.

9. The method of claim 8, wherein the influenza virus infection is influenza A or influenza B.

10. The method of claim 9, wherein the influenza A virus is selected from the group consisting of H1N1, H1N3, H3N2, H3N8, H5N1, H5N6, and H7N9.

11. The method of claim 8, wherein the HA comprises a mutation that reduces aggregation and non-specific binding to sialic acid.

12. The method of claim 8, wherein a cleavage site of HA is replaced with a linker sequence.

13. The method of claim 8, wherein the hybrid protein comprises SEQ ID NO: 13.

14. The method of claim 8, wherein the hybrid protein comprises the sequence selected from the group consisting of SEQ ID NOS: 24-27.

15. A method for reducing viral load resulting from influenza virus infection in a subject in need thereof, comprising:

administering to the subject in need thereof an effective amount of a pharmaceutical composition comprising a hybrid protein comprising the sequence selected from the group consisting of SEQ ID NOS: 13, 24, 25, 26, and 27; and a pharmaceutically acceptable carrier.

16. A method for increasing immunity to influenza virus infection in a subject in need thereof, comprising:

administering to the subject in need thereof an effective amount of a pharmaceutical composition comprising a hybrid protein comprising the sequence selected from the group consisting of SEQ ID NOS: 13, 24, 25, 26, and 27; and a pharmaceutically acceptable carrier.

17. The method of claim 1, wherein the hybrid protein comprises a linker sequence and a foldon sequence between the HA ectodomain and the NA ectodomain.

18. The method of claim 8, wherein the hybrid protein comprises a linker sequence and a foldon sequence between the HA ectodomain and the NA ectodomain.

19. The method of claim 1, wherein the hybrid protein further comprises a linker between the HA ectodomain and the NA ectodomain.

20. The method of claim 8, wherein the hybrid protein further comprises a linker between the HA ectodomain and the NA ectodomain.

21. The method of claim 1, wherein the composition is a vaccine.

22. The method of claim 8, wherein the composition is a vaccine.

23. The method of claim 1, wherein the administering comprises administering a first priming dose of the composition followed by at least one booster dose of the composition.

24. The method of claim 8, wherein the administering comprises administering a first priming dose of the composition followed by at least one booster dose of the composition.

* * * * *